United States Patent
Alberti et al.

(10) Patent No.: US 7,166,597 B2
(45) Date of Patent: *Jan. 23, 2007

(54) FUSED PYRAZOLE DERIVATIVES BEING PROTEIN KINASE INHIBITORS

(75) Inventors: Michael John Alberti, Research Triangle Park, NC (US); Ian Robert Baldwin, Stevenage (GB); Mui Cheung, Research Triangle Park, NC (US); Stuart Cockerill, Stevenage (GB); Stephen Flack, Stevenage (GB); Philip Anthony Harris, Stevenage (GB); David Kendall Jung, Research Triangle Park, NC (US); Gregory Peckham, Research Triangle Park, NC (US); Michael Robert Peel, Research Triangle Park, NC (US); Jennifer Gabriel Badiang, Research Triangle Park, NC (US); Kirk Stevens, Research Triangle Park, NC (US); James Marvin Veal, Research Triangle Park, NC (US)

(73) Assignee: Glaxo Group Limited, Greenford (GB)

( * ) Notice: Subject to any disclaimer, the term of this patent is extended or adjusted under 35 U.S.C. 154(b) by 289 days.

This patent is subject to a terminal disclaimer.

(21) Appl. No.: 10/362,146

(22) PCT Filed: Aug. 22, 2001

(86) PCT No.: PCT/GB01/03783

§ 371 (c)(1),
(2), (4) Date: Jul. 7, 2003

(87) PCT Pub. No.: WO02/16359

PCT Pub. Date: Feb. 28, 2002

(65) Prior Publication Data

US 2004/0053942 A1    Mar. 18, 2004

(30) Foreign Application Priority Data

Aug. 22, 2000 (GB) ............................ 0020556.7
Aug. 22, 2000 (GB) ............................ 0020576.5

(51) Int. Cl.
    C07D 471/04 (2006.01)
    A61K 31/437 (2006.01)
    C07F 5/02 (2006.01)

(52) U.S. Cl. ................ 514/235.8; 514/252.18; 514/274; 514/275; 540/601; 544/122; 544/315; 544/316; 544/331

(58) Field of Classification Search ............... 544/122, 544/315, 316, 331; 540/601; 514/217.06, 514/235.8, 275, 252.18, 274

See application file for complete search history.

(56) References Cited

U.S. PATENT DOCUMENTS

| | | |
|---|---|---|
| 4,200,750 A | 4/1980 | Warner et al. |
| 4,576,952 A | 3/1986 | Hurst et al. |
| 4,621,089 A | 11/1986 | Ward et al. |
| 4,670,432 A | 6/1987 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,236,934 A | 8/1993 | VanAtten |
| 5,246,943 A | 9/1993 | Blankley et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,521,213 A | 5/1996 | Prasit et al. |
| 5,534,518 A | 7/1996 | Henrie et al. |
| 5,552,422 A | 9/1996 | Gauthier et al. |
| 5,658,903 A | 8/1997 | Adams et al. |
| 5,700,816 A | 12/1997 | Isakson et al. |
| 5,858,995 A | 1/1999 | Kawai et al. |
| 5,932,576 A | 8/1999 | Anantanarayan et al. |

(Continued)

FOREIGN PATENT DOCUMENTS

| | | |
|---|---|---|
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |

(Continued)

OTHER PUBLICATIONS

Laszio et al., Pyrroles and other heterocycles as inhibitors of p38 kinase, Bioorganic & Medicinal Chemistry Letters, 8(19), pp. 2689-2694 (1998).*

(Continued)

Primary Examiner—Deepak Rao
(74) Attorney, Agent, or Firm—Lorie Ann Morgan

(57) ABSTRACT

Compounds of Formula (I): salts or solvates or physiologically functional derivatives thereof, wherein Z is CH or N, and $R^1$, $R^2$, and $R^4$ are various substituent groups, are protein kinase inhibitors 13 Claims, No Drawings

U.S. PATENT DOCUMENTS

| | | | |
|---|---|---|---|
| 5,945,418 A | 8/1999 | Bemis et al. | |
| 5,977,103 A | 11/1999 | Adams et al. | |
| 5,990,148 A | 11/1999 | Isakson et al. | |
| 6,087,496 A | 7/2000 | Anantanarayan et al. | |
| 6,130,235 A | 10/2000 | Mavunkel et al. | |
| 6,136,839 A | 10/2000 | Isakson et al. | |
| 6,147,080 A | 11/2000 | Bemis et al. | |
| 6,174,887 B1 | 1/2001 | Haruta et al. | |
| 6,207,675 B1 | 3/2001 | Carry et al. | |
| 6,251,914 B1 | 6/2001 | Adams et al. | |
| 6,277,989 B1 | 8/2001 | Chakravarty et al. | |
| 6,436,925 B1 | 8/2002 | Lubisch et al. | |
| 6,451,794 B1 | 9/2002 | Beswick et al. | |
| 6,498,166 B1 | 12/2002 | Campbell et al. | |
| 6,509,361 B1 | 1/2003 | Weier et al. | |
| 6,509,363 B2 | 1/2003 | Salituro et al. | |
| 6,579,872 B1 | 6/2003 | Brown et al. | |
| 6,638,980 B1 | 10/2003 | Su et al. | |
| 6,756,498 B2 | 6/2004 | Fitzgerald et al. | |
| 6,774,127 B2 | 8/2004 | Adams et al. | |
| 6,855,719 B1 | 2/2005 | Thomas et al. | |
| 6,919,352 B2 | 7/2005 | Chamberlain et al. | |
| 6,962,914 B2 * | 11/2005 | Gudmundsson et al. | 514/233.2 |
| 2001/0011135 A1 | 8/2001 | Reidl et al. | |
| 2004/0038858 A1 | 2/2004 | Dorsch et al. | |
| 2004/0176446 A1 | 9/2004 | Alonso-Alija et al. | |
| 2004/0242868 A1 | 12/2004 | Angell et al. | |
| 2004/0249161 A1 | 12/2004 | Angell et al. | |
| 2004/0266839 A1 | 12/2004 | Angell et al. | |
| 2004/0267012 A1 | 12/2004 | Angell et al. | |
| 2005/0020540 A1 | 1/2005 | Angell et al. | |
| 2005/0020590 A1 | 1/2005 | Lang et al. | |
| 2005/0038014 A1 | 2/2005 | Angell et al. | |
| 2005/0065195 A1 | 3/2005 | Angell et al. | |
| 2005/0090491 A1 | 4/2005 | Angell et al. | |

FOREIGN PATENT DOCUMENTS

| | | |
|---|---|---|
| EP | 0 533 266 | 9/1992 |
| EP | 0 533 268 | 9/1992 |
| EP | 0 346 841 | 6/2003 |
| EP | 0 430 033 | 4/2004 |
| FR | 2 757 059 | 6/1998 |
| GB | 2 276 161 | 3/1993 |
| GB | 2 276 162 | 3/1993 |
| GB | 2 273 930 | 12/1993 |
| GB | 2 295 387 | 5/1996 |
| WO | EP 0 364 204 A1 | 10/1989 |
| WO | WO 91/00092 | 1/1991 |
| WO | WO 91/19497 | 12/1991 |
| WO | WO 94/15920 | 7/1994 |
| WO | WO 95/00501 | 1/1995 |
| WO | WO 95/06636 | 3/1995 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | WO 95/29907 | 11/1995 |
| WO | WO 95/30675 | 11/1995 |
| WO | 96/06840 | 3/1996 |
| WO | WO 96/21667 | 7/1996 |
| WO | 96/31509 | 10/1996 |
| WO | WO 96/31508 | 10/1996 |
| WO | WO 96/41625 | 12/1996 |
| WO | WO 96/41626 | 12/1996 |
| WO | WO 96/41645 | 12/1996 |
| WO | WO 97/03034 | 1/1997 |
| WO | 98/56377 | 12/1998 |
| WO | WO 98 56377 | 12/1998 |
| WO | 99/12930 | 3/1999 |
| WO | WO 99/32463 | 7/1999 |
| WO | 99/58523 | 11/1999 |
| WO | WO 99/59585 | 11/1999 |
| WO | WO 99/64419 | 12/1999 |
| WO | WO 00/12074 | 3/2000 |
| WO | WO 00/12497 | 3/2000 |
| WO | 00/26216 | 5/2000 |
| WO | 00/52008 | 9/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/00615 | 1/2001 |
| WO | 01/14375 | 3/2001 |
| WO | WO 01/27089 | 4/2001 |
| WO | WO 01/34605 | 5/2001 |
| WO | WO 01/70695 | 9/2001 |
| WO | WO 01/83479 | 11/2001 |
| WO | WO 01/87875 | 11/2001 |
| WO | WO 02/16359 | 2/2002 |
| WO | WO 02/18382 | 3/2002 |
| WO | WO 02/40486 | 5/2002 |
| WO | WO 02/48147 | 6/2002 |
| WO | WO 02/48148 | 6/2002 |
| WO | WO 02/66481 | 8/2002 |
| WO | WO 03/000682 | 1/2003 |
| WO | WO 03/032970 | 4/2003 |
| WO | WO 03/068747 | 8/2003 |
| WO | WO 03/093248 | 11/2003 |
| WO | WO 04/010995 | 2/2004 |
| WO | WO 04/089874 | 10/2004 |
| WO | WO 04/089875 | 10/2004 |
| WO | WO 04/089876 | 10/2004 |
| WO | WO 05/014550 | 2/2005 |
| WO | WO 05/061465 | 7/2005 |

OTHER PUBLICATIONS

Layzer, Degenerative Diseases of the Nervous System, Cecil Textbook of Medicine, 20th Edition, vol. 2, pp. 2050-2057, 1996.*

Simone, Oncology: Introduction, Cecil Textbook of Medicine, 20th Edition, vol. 1, pp. 1004-1010, 1996.*

Damasio, Alzheimer's Disease and Related Dementias, Cecil Textbook of Medicine, 20th Edition, vol. 2, Jun. 1992, 1996.*

Boehm et al., "1-Substituted 4-Aryl-5pyridinylimidazoles: A New Class of Cytokine Suppressive Drugs with Low 5-Lipoxygenase and Cyclooxygenase Inhibitory Potency," *Journal of Medicinal Chemistry, American Chemical Society, Washington, US*, vol. 39, 20 (Sep. 27, 1996), pp. 3929-3937.

Hanson, G.J., "Inhibitors of p38 kinase," *Expert Opinion on Therapeutic Patents, Ashley Publications, GB*, vol. 7, No. 7, pp. 729-733, 1997.

Boehm et al., *Expert Opinion of Therapeutic Patents*, vol. 10 (1) pp. 25-37 (2000).

Ceccarelli et al., *European Journal of Medicinal Chemistry*, vol. 33 (12) pp. 943-955 (1998).

Gabriele et al., *European Journal of Organic Chemistry*, vol. 2001 (24) pp. 4607-4613 (2001).

Han et al., *Biohemica et Biophysica Acta—Molecular Cell Research* vol. 1265 (2-3) pp. 224-227 (1995).

Henry et al., *Drugs of the Future*, vol. 24 (12) pp. 1345-1354 (1999).

Jiang et al, *Journal of Biological Chemistry*, vol. 271 (30) pp. 17920-17926 (1996).

Li et al., *Biochemical and Biophysical Research Communications*, vol. 228 (2) pp. 334-340 (1996).

Liebeskind et al., *Organic Letters*, vol. 4 (6) pp. 979-981 (2002).

Moreland et al., *Annals of Internal Medicine*, vol. 130 (6) pp. 478-486 (1999).

Murali Dhar et al., *Bioorganic and Medicinal Chemistry Letters*, vol. 12 (21) pp. 3125-3128 (2002).

Rankin et al., *British Journal of Rheumatology*, vol. 34 pp. 334-342 (1995).

Salituro et al., *Current Medicinal Chemistry*, vol. 6 pp. 807-823 (1999).

Wang et al., *Journal of Biological Chemistry*, vol. 272 (38) pp. 23668-23674 (1997).

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Bosseray et al., Pub Med Abstract (Pathol Biol (Paris) 50(8):483-92) Oct. 2002.

Carter, J. et al. "Recently Reported Inhibitors of Cyclooxygenase-2." Exp. Opin. Ther. Patents (1998), 8(1), pp. 21-29.

Douglas, Jr. Introduction to Viral Diseases, Cecil Textbook of Medicine, 20th Edition, vol. 2, pp. 1739-1747, 1996.

Razonable et al. Pub Med Abstract (Herpes. 10(3):60-5) Dec. 2003.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Talley, John J., 5 Selective Inhibitors of Cyclooxygenase-2 (COX-2) *Progress in Medicinal Chemistry*, vol. 36, (1999): pp. 201-234.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Vane, J. et al. "Towards a Better Aspirin." Nature, vol. 367, Jan. 20, 1994, pp. 215-216.

\* cited by examiner

FUSED PYRAZOLE DERIVATIVES BEING PROTEIN KINASE INHIBITORS

This application is filed pursuant to 35 U.S.C. § 371 as a United States National Phase Application of International Application No. PCT/GB01/03783 filed Aug. 22, 2001, which claims priority from 0020556.7 and 0020576.5 filed Aug. 22, 2000.

The present invention relates to novel pyrazole derivatives, methods for their preparation, and their use to treat certain diseases or conditions. In particular, the present invention relates to novel protein kinase inhibitors.

Protein kinases play a critical role in the control of cell growth and differentiation, and are key mediators of cellular signals leading to the production of growth factors and cytokines. See, for example, Schiessinger and Ullrich, *Neuron* 1992, 9, 383. A partial, non-limiting list of such kinases includes abl, ATK, bcr-abl, Bik, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, fit-1, Fps, Frk, Fyn, GSK, Hck, IGF-1R, INS-R, Jak, JNK, KDR, Lck, Lyn, MEK, p38, PDGFR, PIK, PKC, PYK2, tie1 tie2, TRK, UL97, VEGF-R1, VEGF-R2, Yes and Zap70.

Protein kinases have been implicated as targets in central nervous system disorders such as Alzheimer's (Mandelkow, E. M. et al. *FEBS Lett.* 1992, 314, 315; Sengupta, A. et al. *Mol. Cell. Biochem.* 1997, 167, 99), pain sensation (Yashpal, K. *J. Neurosci.* 1995, 15, 3263–72), inflammatory disorders such as arthritis (Badger, *J. Pharm. Exp. Ther.* 1996, 279, 1453), psoriasis (Dvir, et al, *J. Cell Biol.* 1991, 113, 857), bone diseases such as osteoporosis (Tanaka et al, *Nature* 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al. *Cancer Res.* 1996, 56, 3540; Jackson et al. *J. Pharm. Exp. Ther.* 1998, 284, 687), restenosis (Buchdunger et al. *Proc. Nat. Acad. Sci USA* 1991, 92, 2258), autoimmune diseases and transplant rejection (Bolen and Brugge, *Ann. Rev. Immunol.* 1997, 15, 371), infectious diseases such as fungal infections (Lum, R. T. PCT Int. Appl., WO 9805335 A1980212), chronic heart failure (Liu, I and Zhao, S. P. *Int. J. Cardiology* 1999, 69, 77–82) and chronic obstructive pulmonary disease (Nguyen, L. T. et al. *Clinical Nutr.* 1999, 18, 255–257; Solar, N. et al. *Eur. Respir. J.* 1999, 14, 1015–1022).

The p38 kinase is involved in the production of several inflammatory factors and cytokines, including, for example, TNFα, IL-1, IL-6, IL-8, Cox-2 and matrix metalloproteinases. Inhibition of p38 kinase results in the inhibition of production of these inflammatory mediators by cells treated with inflammatory stimuli. See, for example, Lee, *Nature* 1994, 372, 739, and Gallagher, *Bioorganic & Medicinal Chemistry* 1997, 5, 49. This suggests that inhibition of p38 kinase should offer a method for the treatment of certain cytokine mediated diseases (Dinarello, C. A. *J. Biol. Regul. Homeostatic Agents* 1997, 11, 91).

The JNK kinases exist in three subtypes (JNK1, JNK2 and JNK3) and ten isoforms. They are activated in response to extracellular stimuli such as cytokines (e.g. Fas, IL1 and TNF) and inflammatory mediators, and by noxious stimuli such as UV, changes in calcium homeostasis and osmotic pressure, and by withdrawal of trophic factor. Their activation results in the activation of the AP1 transcription factor complex; the genes transcribed depend on the other components of the complex, and on the specific JNK activated. In general, the JNK kinases are known to mediate apoptotic and inflammatory responses. JNK3 is a key mediator in the apoptotic cell-death of neuronal cells and it appears to be involved selectively in apoptosis in the brain rather than peripherally. JNKs 1 and 2 are more widely distributed and although their normal function is not precisely known, they are generally more closely linked to mediation of inflammation. This suggests that inhibition of JNK kinases should also offer a method for the treatment of certain cytokine mediated diseases.

WO 01/14375 published after the priority date of the present application discloses various imidazo[1,2-A]pyridine and pyrazolo[2,3-A]pyridine derivatives which possess cell-cycle inhibitory activity.

The present invention provides novel compounds, compositions and methods for treating diseases and conditions mediated by p38 kinase and for treating diseases and conditions mediated by cytokines which are produced by the activity of p38 kinase. Thus the present invention provides novel compounds, compositions and methods for treating, for example, inflammatory diseases and conditions, and autoimmune diseases and reactions.

The present invention also provides novel compounds, compositions and methods for treating diseases and conditions mediated by JNK kinases and for treating diseases and conditions mediated by cytokines which are produced by the activity of JNK kinases. Thus the present invention provides novel compounds, compositions and methods for treating, for example, inflammatory diseases and conditions, and autoimmune diseases and reactions.

As used herein the terms "p38" or "p38 kinase" include all isoforms thereof, including the alpha, beta, beta2, gamma and delta isoforms.

As used herein the terms "JNK" or "JNK kinase" include the three subtypes JNK1, JNK2 and JNK3 and all isoforms thereof.

In one aspect, the present invention provides a compound of Formula (I):

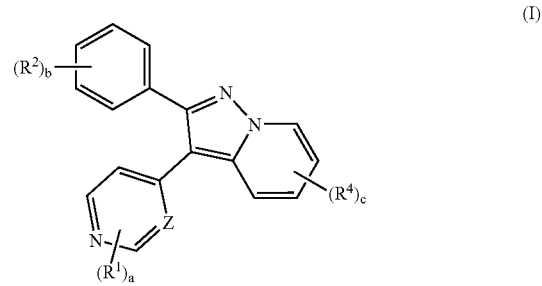

or a salt or solvate thereof or a physiologically functional derivative thereof:

wherein

Z is CH or N;

a is 1 or 2;

b is 1, 2 or 3;

c is 1, 2 or 3;

each $R^1$ is independently selected from groups of the formula $$-(X)_d-(CH_2)_e-R^5$$

wherein d is 0 or 1;

e is 0 to 6;

X is O, $NR^6$ or $S(O)_f$ where f is 0, 1 or 2;

$R^5$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, $NR^7R^8$, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$, $C(=NR^7)NR^7R^8$, $NR^7(C=NR^7)NR^7R^8$, $NHC(O)R^7$ or $N(C_{1-3}alkyl)C(O)R^7$;

each $R^2$ is independently selected from hydrogen, cyano, halogen, trihalomethyl, $OC_{1-6}$alkyl, $C_{1-6}$alkyl, $C_{2-6}$alkenyl, $C_{2-6}$alkynyl, $S(O)_g C_{1-6}$alkyl where g is 0, 1 or 2, $NC_{1-6}$alkyl($C_{1-6}$alkyl), hydroxyl or nitro;

each $R^4$ is independently selected from groups of the formula

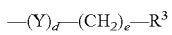

wherein d is 0 or 1;

e is 0 to 6;

Y is O or $S(O)_f$ where f is 0, 1 or 2;

$R^3$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, phthalamido, $C^6H_4NR^7R^8$ $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO^2NR^7R^8$ or $C(=NR^7)NR^7R^8$;

$R^6$ is H, $C_{1-6}$alkyl, $C_{2-6}$alkenyl, aryl, heteroaryl, $C_{3-12}$cycloalkyl, or heterocyclyl;

$R^7$ and $R^8$ are each independently H, $C_{1-8}$alkyl, $C_{2-6}$alkenyl, $SO_2C_{1-6}$alkyl, $(CH_2)_m-C_{3-12}$cycloalkyl, $(CH_2)_m$-aryl, $(CH_2)_m$-heterocyclyl, $(CH_2)_m$-heteroaryl, wherein m is 0, 1 or 2, or may, together with the nitrogen atom to which they are bound, form a heterocyclyl group; and wherein any of said alkyl, alkenyl and alkynyl groups may be optionally substituted with up to three members selected from halogen, hydroxyl, oxo, cyano, $NR^7R^8$, $C_{1-6}$alkyl, $OC_{1-6}$alkyl, $S(O)C_{1-6}$alkyl, $S(O)_2C_{1-6}$alkyl and $SO_2NR^7R^8$; and wherein any of said cycloalkyl, heterocyclyl, aryl, and heteroaryl groups may be optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_{1-6}$alkyl, carbamoyl optionally substituted by $C_{1-6}$alkyl, $NR^7R^8$, carboxy and aminosulfonyl optionally substituted by $C_{1-6}$alkyl;

with the proviso that $(R^2)_b$, $(R^1)_a$ and $(R^4)_c$ cannot all represent solely hydrogen substitution;

and with the proviso that when $(R^2)_b$ represents solely hydrogen or methyl substitution, $(R^4)_c$ cannot represent solely hydrogen substitution;

and with the proviso that $R^4$ may not be located on the 7-position of the pyrazolopyridine ring system as numbered below:

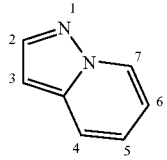

In a preferred embodiment, a salt or solvate of a compound of formula (I) will be a pharmaceutically acceptable salt or solvate thereof.

In another aspect, the present invention provides a pharmaceutical composition comprising a compound of formula (I) or a salt or solvate thereof, or a physiologically functional derivative thereof, in admixture with one or more pharmaceutically acceptable carriers, diluents or excipients.

In another aspect, the present invention provides a compound of formula (I) or a salt or solvate thereof, or a physiologically functional derivative thereof, for use in therapy.

The present invention provides compounds which inhibit or reduce p38 kinase activity or which inhibit or reduce cytokine production resulting from the activity of p38 kinase. Thus, in another aspect, the present invention provides for the use of a compound of formula (I) or a salt or solvate thereof, or a physiologically functional derivative thereof, for the preparation of a medicament for the treatment of a condition or disease state mediated by p38 kinase activity or mediated by cytokines produced by the activity of p38 kinase.

The present invention provides compounds which inhibit or reduce JNK kinase activity or which inhibit or reduce cytokine production resulting from the activity of JNK kinases. Thus, in another aspect, the present invention provides for the use of a compound of formula (I) or a salt or solvate thereof, or a physiologically functional derivative thereof, for the preparation of a medicament for the treatment of a condition or disease state mediated by JNK kinase activity or mediated by cytokines produced by the activity of JNK kinase.

The present invention also provides compounds which inhibit or reduce both p38 and JNK kinase activity or which inhibit or reduce cytokine production resulting from the activity of both p38 and JNK kinase. Thus, in another aspect, the present invention provides for the use of a compound of formula (I) or a salt or solvate thereof, or a physiologically functional derivative thereof, for the preparation of a medicament for the simultaneous treatment of two or more conditions or disease states independently mediated by p38 and JNK kinase activity or independently mediated by cytokines produced by the activity of p38 and JNK kinase.

In another aspect, the present invention provides a method for treating a condition or disease mediated by p38 kinase activity or mediated by cytokines produced by the activity of p38 kinase using a compound of formula (I) or a salt or solvate thereof, or a physiologically functional derivative thereof.

In another aspect, the present invention provides a method for treating a condition or disease mediated by JNK kinase activity or mediated by cytokines produced by the activity of JNK kinase using a compound of formula (I) or a salt or solvate thereof, or a physiologically functional derivative thereof.

In another aspect, the present invention provides a method for treating two or more conditions or diseases independently mediated by p38 and JNK kinase activity or independently mediated by cytokines produced by the activity of p38 and JNK kinase using a compound of formula (I) or a salt or solvate thereof, or a physiologically functional derivative thereof.

As used herein, the term "physiologically functional derivative" refers to any pharmaceutically acceptable derivative of a compound of the present invention, for example, an ester or an amide, which upon administration to a mammal, such as a human, is capable of providing (directly or indirectly) such a compound or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles And Practice, which is incorporated herein by reference.

As used herein, the terms "alkyl" and "alkylene" refer to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, and isopropyl. Examples of "alkylene" as used herein include, but are not limited to, methylene, ethylene, propylene and butylene. The said alkyl groups may be optionally substituted with up to three members selected from halogen, hydroxyl, oxo, cyano, $NR^7R^8$, $C_{1-6}$alkyl, $OC_{1-6}$alkyl, $S(O)C_{1-6}$alkyl, $S(O)_2C_{1-6}$alkyl and $SO_2NR^7R^8$. A preferred substituent for said alkyl groups is $C_{1-4}$alkyl, more preferably n-butyl. Thus a preferred substituted alkyl group is n-octyl.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl and propenyl. The said alkenyl groups may be optionally substituted with up to three members selected from halogen, hydroxyl, oxo, cyano, $NR^7R^8$, $C_{1-6}$alkyl, $OC_{1-6}$alkyl, $S(O)C_{1-6}$alkyl, $S(O)_2C_{1-6}$alkyl and $SO_2NR^7R^8$.

As used herein, the term "alkynyl" refers to straight or branched hydrocarbon chains containing the specified number of carbon atoms and containing at least one triple bond. For example, $C_{2-6}$alkynyl means a straight or branched alkynyl containing at least 2, and at most 6, carbon atoms and containing at least one triple bond. Examples of "alkynyl" as used herein include, but are not limited to, ethynyl and propynyl. The said alkynyl groups may be optionally substituted with up to three members selected from halogen, hydroxyl, oxo, cyano, $NR^7R^8$, $C_{1-6}$alkyl, $OC_{1-6}$alkyl, $S(O)C_{1-6}$alkyl, $S(O)_2C_{1-6}$alkyl and $SO_2NR^7R^8$.

As used herein, the term "cycloalkyl" refers to a non-aromatic hydrocarbon ring having from three to twelve carbon atoms. The said ring may optionally contain up to three carbon-carbon double bonds. "Cycloalkyl" includes by way of example cyclopropyl, cyclobutyl, cyclopentyl, cyclohexyl, cycloheptyl and cyclooctyl. Preferred cycloalkyls are cyclopentyl and cyclohexyl. The said ring may be optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_{1-6}$alkyl, carbamoyl optionally substituted by $C_{1-6}$alkyl, $NR^7R^8$, carboxy, aminosulfonyl optionally substituted by $C_{1-6}$alkyl. A preferred substituent for said cycloalkyl groups is $C_{1-4}$alkyl, more preferably methyl. Thus a preferred substituted cycloalkylalkyl group is methylcyclopentyl, more preferably 3-methylcyclopentyl. As used herein, the terms "heterocycle", "heterocyclyl" and "heterocyclic" refer to a monocyclic five to seven membered non-aromatic hydrocarbon ring or to a fused bicyclic non-aromatic hydrocarbon ring system comprising two of such monocyclic five to seven membered non-aromatic hydrocarbon rings. The ring or rings containing at least one heteroatom selected from 0, S, or N where N-oxides, sulfur oxides and sulfur dioxides are permissible heteroatom substitutions. The said ring system may optionally contain up to three carbon-carbon, or carbon-nitrogen, double bonds. The said ring system may optionally be fused to one or more benzene rings. Examples of heterocycles include, but are not limited to, tetrahydrofuran, dihydropyran, tetrahydropyran, pyran, oxetane, thietane, 1,4-dioxane, 1,3-dioxane, 1,3-dioxalane, homopiperidine, piperidine, piperidine fused to a benzene ring, piperazine, tetrahydropyrimidine, pyrrolidine, imidazoline, morpholine, thiomorpholine, thioxane, thiazolidine, oxazolidine, tetrahydrothiopyran, tetrahydrothiophene, and the like. Preferred heterocycles include morpholine, pyrrolidine, imidazolidine, homopiperidine, piperidine, piperidine fused to a benzene ring, piperazine, tetrahydropyran and tetrahydrothiopyran. The said ring system may be optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_{1-6}$alkyl, carbamoyl optionally substituted by $C_{1-6}$alkyl, $NR^7R^8$, carboxy, aminosulfonyl optionally substituted by $C_{1-6}$alkyl. Preferred substituents for said heterocyclyl groups are oxo and $C_{1-6}$alkyl, more preferably methyl, n-propyl and isopropyl. Thus preferred substituted heterocyclyl groups are imidazolidine-2,5-dione, 2-methylpiperidine, N-methylpiperazine, N-propylpiperazine and N-isopropylpiperazine.

As used herein, the term "aryl" refers to an optionally substituted phenyl or naphthyl ring. Said rings may be optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_{1-6}$alkyl, carbamoyl optionally substituted by $C_{1-6}$alkyl, $NR^7R^8$, carboxy, aminosulfonyl optionally substituted by $C_{1-6}$alkyl.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, or oxygen heteroatoms, where N-oxides and sulfur oxides and dioxides are permissible heteroatom substitutions. Examples of "heteroaryl" used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. Preferred heteroaryl groups include furan, pyrrole, imidazole, pyridine, pyrimidine, and thiophene. The rings are optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_1$alkyl, carbamoyl optionally substituted by $C_{1-6}$alkyl, $NR^7R^8$, carboxy, aminosulfonyl optionally substituted by $C_{1-6}$alkyl.

As used herein, the term "alkoxy" refers to the group R$_a$O—, where R$_a$ is alkyl as defined above.

As used herein, the term "alkylsulfenyl" refers to the group R$_a$S—, where R$_a$ is alkyl as defined above.

As used herein, the term "alkylsulfinyl" refers to the group R$_a$S(O)—, where R$_a$ is alkyl as defined above.

As used herein, the term "alkylsulfonyl" refers to the group R$_a$SO$_2$—, where R$_a$ is alkyl as defined above.

As used herein, the terms "halogen" or "halo" refer to the elements fluorine, chlorine, bromine and iodine. Preferred halogens are fluorine, chlorine and bromine. A particularly preferred halogen is fluorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above-defined alkyl, alkenyl, alkynyl or cycloalkyl substituents with one or more of any of O, S, SO, SO$_2$, N, or N-alkyl, including, for example, —CH$_2$—O—CH$_2$—, —CH$_2$—SO$_2$—CH$_2$—, —CH$_2$—NH—CH$_2$— and so forth.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

In one embodiment, Z is CH. This provides compounds of formula (II) below:

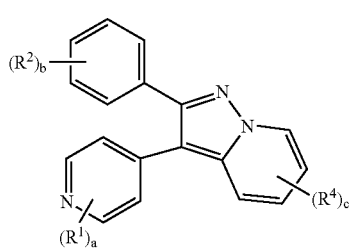

(II)

In the embodiments represented by formula (II) when a is 1, the most preferred location for R$^1$ is on one of the carbon atoms closest to the pyridyl nitrogen, i.e. in the 2-position. This provides compounds of formula (III) below:

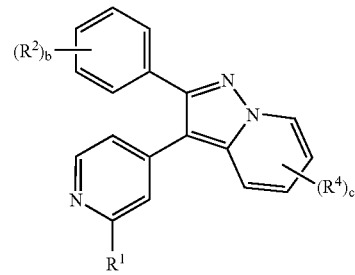

(III)

In the embodiments represented by formula (II) when a is 2, the most preferred locations for the R$^1$ groups are on the two carbon atoms closest to the pyridyl nitrogen, i.e. in the 2- and 6-positions.

In another embodiment, Z is N. This provides compounds of formula (IV) below:

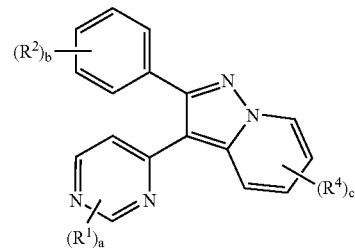

(IV)

In the embodiments represented by formula (IV) when a is 1, a preferred location for R$^1$ is on the carbon atom between the pyrimidyl nitrogens, i.e. in the 2-position. This provides compounds of formula (V) below:

(V)

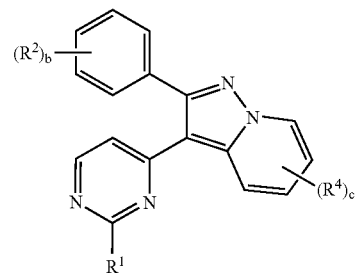

In the embodiments represented by formula (IV) when a is 1, another preferred location for R$^1$ is illustrated by compounds of formula (VI) below:

(VI)

In a preferred embodiment, when a is 2, at least one of the R$^1$ groups is F.

Preferably a is 1.

In an embodiment, $R^1$ is selected from hydrogen or a halogen, preferably fluorine.

In another embodiment, $R^1$ is selected from groups of the formula —O—$(CH_2)_e$—$R^5$ wherein e is 0 to 6, preferably 0 or 1; and $R^5$ is $C_{1-6}$alkyl (preferably methyl or n-butyl), aryl (preferably phenyl), or trihalomethyl (preferably trifluoromethyl). Thus preferred embodiments of $R^1$ include OMe, O"Bu, OPh and $OCH_2CF_3$.

In another embodiment, $R^1$ is selected from groups of the formula —$S(O)_f$—$R^5$ wherein f is 0, 1 or 2; and $R^5$ is $C_{1-6}$alkyl (preferably methyl). Thus preferred embodiments of $R^1$ include SMe, SOMe and $S(O)_2Me$.

In another embodiment, $R^1$ is selected from groups of the formula

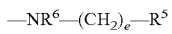

wherein e is 0 to 6; and $R^5$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, $NR^7R^8$, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$, $C(=NR^7)NR^7R^8$, $NR^7(C=NR^7)NR^7R^8$, $NHC(O)R^7$ or $N(C_{1-3}alkyl)C(O)R^7$;

$R^6$ is H, $C_{1-6}$alkyl, $C_{2-6}$alkenyl, aryl, heteroaryl, $C_{3-12}$cycloalkyl, or heterocyclyl, $R^7$ and $R^8$ are each independently H, $C_{1-8}$alkyl, $C_{2-6}$alkenyl, $SO_2C_{1-6}$alkyl, $(CH_2)_m$—$C_{3-12}$cycloalkyl, $(CH_2)_m$-aryl, $(CH_2)_m$-heterocyclyl, $(CH_2)_m$-heteroaryl, wherein m=0, 1 or 2, or may, together with the nitrogen atom to which they are bound, form a heterocyclyl group.

In a preferred embodiment, $R^1$ is selected from groups of the formula

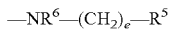

wherein e is 0 to 6; and $R^5$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, $NR^7R^8$, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$, $C(=NR^7)NR^7R^8$, $NR^7(C=NR^7)NR^7R^8$, $NHC(O)R^7$ or $N(C_{1-3}alkyl)C(O)R^7$;

$R^6$ is H or $C_{1-6}$alkyl (preferably methyl);

$R^7$ and $R^8$ are each independently H, $C_{1-8}$alkyl, $C_{2-6}$alkenyl, $SO_2C_{1-6}$alkyl, $(CH_2)_m$—$C_{3-12}$cycloalkyl, $(CH_2)_m$-aryl, $(CH_2)_m$-heterocyclyl, $(CH_2)_m$-heteroaryl, wherein m=0, 1 or 2, or may, together with the nitrogen atom to which they are bound, form a heterocyclyl group.

In a preferred embodiment, $R^1$ is selected from groups of the formula

—N(Me)-$(CH_2)_e$—$R^5$ wherein e is 0 to 6 (preferably 0); and $R^5$ is $C_{1-6}$alkyl (preferably methyl). Thus a preferred embodiment of $R^1$ is $N(Me)_2$.

In a preferred embodiment, $R^1$ is selected from groups of the formula

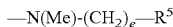

wherein e is 0 to 6; and $R^5$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, $NR^7R^8$, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$, $C(=NR^7)NR^7R^8$, $NR^7(C=NR^7)NR^7 R^8$, $NHC(O)R^7$ or $N(C_{1-3}alkyl)C(O)R^7$;

$R^7$ and $R^8$ are each independently H, $C_{1-8}$alkyl, $C_{2-6}$alkenyl, $SO_2C$, alkyl, $(CH_2)_m$—$C_{3-12}$cycloalkyl, $(CH_2)_m$-aryl, $(CH_2)_m$-heterocyclyl, $(CH_2)_m$-heteroaryl, wherein m=0, 1 or 2, or may, together with the nitrogen atom to which they are bound, form a heterocyclyl group.

In a preferred embodiment, $R^1$ is selected from groups of the formula —NH—$R^5$ wherein $R^5$ is hydrogen, $C_{1-6}$alkyl (preferably propyl, iso-propyl, n-butyl, n-pentyl or n-hexyl), $C_{2-6}$alkenyl (preferably propenyl), $C_{3-12}$cycloalkyl (preferably cyclopropyl, cyclopentyl or cyclohexyl), aryl (preferably phenyl) or substituted aryl (preferably 4-fluorophenyl).

In a preferred embodiment, $R^1$ is selected from groups of the formula

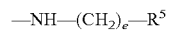

wherein e is 1 to 6 (preferably 1, 2, 3 or 4, more preferably 1, 2 or 3); and $R^5$ is heterocyclyl (preferably piperidine, homopiperidine, piperazine, morpholine, pyrolidine or imidazolidine), aryl (preferably phenyl), substituted aryl (preferably 4-chlorophenyl or 4-methoxyphenyl), heteroaryl (preferably pyridine or imidazole), hydroxyl, trihalomethyl (preferably trifluoromethyl). Thus preferred embodiments of $R^1$ include $NHCH_2Ph$, $NHCH_2$(4-chlorophenol), $NHCH_2$(4-methoxyphenol), $NH(CH_2)_2OH$, $NH(CH_2)_3OH$,

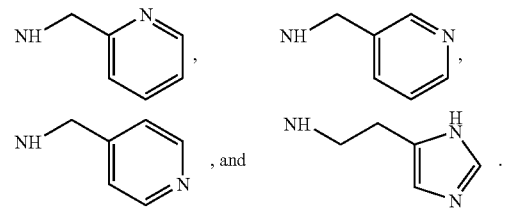

A particularly preferred embodiment of $R^1$ is $NH(CH_2)_3OH$.

In a preferred embodiment, $R^1$ is selected from groups of the formula

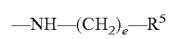

wherein e is 1 to 6 (preferably 1, 2, 3 or 4); and $R^5$ is $NR^7R^8$, $C_6H_4NR^7R^8$, $C_6H_4(CH_2)NR^7R^8$, $C(O)NR^7R^8$, $OC(O)NR^7R^8$, $SO_2R^7$, $SO_2NR^7R^8$, $NHC(O)R^7$ or $N(C_{1-3}alkyl)C(O)R^7$;

$R^7$ and $R^8$ are each independently H, $C_{1-8}$alkyl, $C_{2-6}$alkenyl, $SO_2C_{1-6}$alkyl, $(CH_2)_m$—$C_{3-12}$cycloalkyl, $(CH_2)_m$-aryl, $(CH_2)_m$-heterocyclyl, $(CH_2)_m$-heteroaryl, wherein m=0, 1 or 2, or may, together with the nitrogen atom to which they are bound, form a heterocyclyl group.

In a preferred embodiment, $R^1$ is selected from groups of the formula

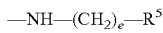

wherein e is 2, 3 or 4 and $R^5$ is $NR^7R_5$ and wherein $R^7$ and $R^8$ are each independently selected from H, $C_{1-4}$alkyl, $S(Q)_2C_{1-4}$alkyl, $(CH_2)_m$—$C_{3-8}$cycloalkyl, $(CH_2)_m$-aryl, $(CH_2)_m$-heterocyclyl, and $(CH_2)_m$-heteroaryl, wherein m=0, 1 or 2.

In a further preferred embodiment, $R^1$ is selected from groups of the formula

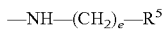

wherein e is 2, 3 or 4, preferably 3, and $R^5$ is $NR^7R^8$ wherein $R^7$ and $R^8$ are each independently selected from H and $C_{1-4}$alkyl. More preferably $R^7$ and $R^8$ are each independently selected from H, methyl, ethyl, n-propyl, iso-propyl, and butyl. Most preferably $R^5$ is represented by a group selected from any one of the following: amino, methylamino, dimethylamino, ethylamino, diethylamino, n-propylamino, di(n-propyl)amino, iso-propylamino, di(iso-propyl)amino and butylamino. In a further embodiment, any of said $C_{1-4}$alkyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl. A preferred substituent for said alkyl groups is $C_{1-4}$alkyl, more preferably n-butyl. Thus $R^5$ is preferably represented by the group n-octylamino.

In a further preferred embodiment, $R^1$ is selected from groups of the formula

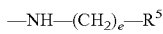

wherein e is 2, 3 or 4, preferably 3, and $R^5$ is $NR^7R^8$ wherein either $R^7$ or $R^8$ is represented by the group $(CH_2)_m$—$C_{3-8}$cycloalkyl wherein m is 0, 1 or 2, preferably 0 or 1, more preferably 0. More preferably, either $R^7$ or $R^8$ represent cyclopentyl or cyclohexyl. Most preferably $R^5$ is represented by a group selected from any one of the following: NH-cyclopentyl, NH—$CH_2$-cyclopentyl and NH-cyclohexyl. In a further embodiment, any of said $C_{3-8}$cycloalkyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl. A preferred substituent for said alkyl groups is $C_{1-4}$alkyl, more preferably methyl. Thus $R^5$ is preferably represented by the group NH-(3-methyl-cyclopentyl).

In a further preferred embodiment, $R^1$ is selected from groups of the formula

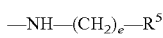

wherein e is 2, 3 or 4, preferably 3, and $R^5$ is $NR^7R^8$ wherein either $R^7$ or $R^8$ is represented by the group $(CH_2)_m$-aryl wherein m is 0, 1 or 2, preferably 0 or 1. More preferably, $R^7$ or $R^8$ represent phenyl or benzyl. Most preferably $R^5$ is represented by a group selected from any one of the following: N(Me)-phenyl and N(Me)-benzyl. In a further embodiment, any of said aryl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl.

In a further preferred embodiment, $R^1$ is selected from groups of the formula

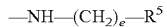

wherein

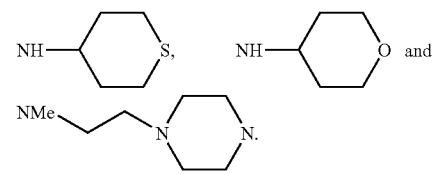

e is 2, 3 or 4, preferably 3, and $R^5$ is $NR^7R^8$ wherein either $R^7$ or $R^8$ is represented by the group $(CH_2)_m$-heterocyclyl wherein m is 0, 1 or 2, preferably 0 or 2. More preferably $R^7$ or $R^8$ represent piperidine, piperazine, morpholine, tetrahydropyran or tetrahydrothiopyran. Most preferably $R^5$ is represented by a group selected from any one of the following:

In a further embodiment, any of said heterocyclyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl.

In a further preferred embodiment, $R^1$ is selected from groups of the formula

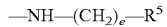

wherein e is 2, 3 or 4, preferably 3, and $R^5$ is $NR^7R^8$ wherein either $R^7$ or $R^8$ are represented by the group $(CH_2)_m$-heteroaryl wherein m is 0, 1 or 2, preferably 1. More preferably $R^7$ or $R^8$ represent furan, pyrrole, imidazole or pyridine. Most preferably $R^5$ is represented by the group:

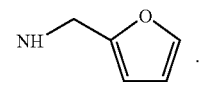

In a further embodiment, any of said heteroaryl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl.

In a further preferred embodiment, $R^1$ is selected from groups of the formula

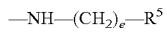

wherein e is 2, 3 or 4, preferably 3, and $R^5$ is $NR^7R^8$ wherein either $R^7$ or $R^8$ are represented by the group $S(O)_2C_{1-4}$alkyl. More preferably $R^7$ or $R^8$ represent $S(O)_2Me$. In a further embodiment, any of said $C_{1-4}$alkyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl.

In a preferred embodiment, $R^1$ is selected from groups of the formula

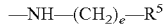

wherein e is 2, 3 or 4, preferably 2 or 3, more preferably 3, and $R^5$ is $NR^7R^8$ wherein both $R^7$ and $R^8$ are taken together with the N atom to which they are bonded to form a heterocyclyl group optionally fused to a benzene ring. Preferably, said heterocyclyl group is selected from piperidine, homopiperidine, piperazine, morpholine, pyrolidine and imidazolidine each of which may be optionally fused to a benzene ring. Most preferably $R^5$ is represented by a group selected from any one of the following:

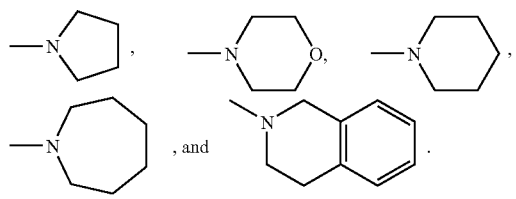

In a further embodiment, any of said heterocyclyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^7R^8$ wherein $R^7$ and $R^8$ are each independently selected from H and $C_{1-4}$alkyl. Preferred substituents for said alkyl groups are oxo and $C_{1-4}$alkyl, more preferably methyl, ethyl, propyl or iso-propyl. Thus $R^5$ is preferably represented by a group selected from any one of the following:

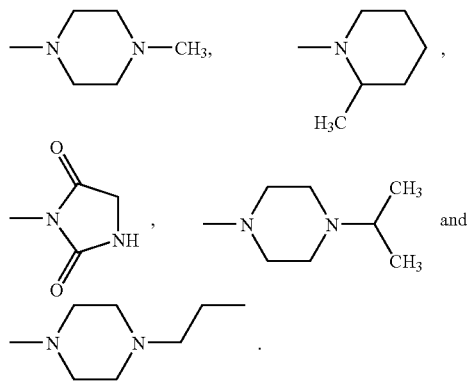

In a preferred embodiment b is 1 or 2.

In a more preferred embodiment each $R^2$ is independently selected from hydrogen, cyano, halogen, trihalomethyl or $OC_{1-6}$alkyl.

In a more preferred embodiment the $R^2$ substituent(s) are in the meta- and/or para-position(s) relative to the bond to the pyrazolopyridine ring system. In a preferred embodiment, each $R^2$ is selected from chloro, fluoro and trifluoromethyl groups. In a more preferred embodiment, $(R^2)_b$ is represented by one or two substituents selected from F or Cl. In a further preferred embodiment, $(R^2)_b$ is represented by a $CF_3$ substituent. In a most preferred embodiment, $(R^2)_b$ and the phenyl ring to which such group(s) is/are bonded is selected from 3-chloro-4-fluorophenyl, 3-chlorophenyl, 4-fluorophenyl and 4-trifluoromethylphenyl. In an especially preferred embodiment, $(R^2)_b$ and the phenyl ring to which such group(s) is/are bonded is 4-fluorophenyl.

In a preferred embodiment c is 1.

In a preferred embodiment $R^4$ is hydrogen.

In a preferred embodiment where c is 1 and $R^4$ is not hydrogen, $R^4$ is bonded to the 5-position or the 6-position as those positions are shown below.

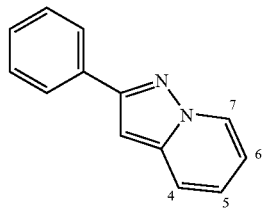

In another preferred embodiment, $R^4$ is selected from $C_{1-6}$alkyl (preferably methyl) bonded to the 4-, 5- or 6-positions, halogen (preferably bromo, chloro or fluoro, more preferably fluoro) bonded to the 4-, 5- or 6-positions (preferably the 6-position), CN bonded to the 6-position, or trihalomethyl (preferably trifluoromethyl) bonded to the 6-position. Most preferably $R^4$ is fluoro bonded to the 6-position.

In another preferred embodiment $R^4$ is selected from groups of the formula

—$CH_2$—R

wherein $R^3$ is selected from OH, phthalamido or $OC(O)R^7$ wherein $R^7$ is aryl (preferably phenyl) or heteroaryl (preferably pyridine or thiophene) optionally substituted with halogen (preferably bromine or chlorine), amino, $C_{1-6}$alkylsulfonyl (preferably methylsulfonyl), aminosulfonyl, $C_{1-6}$alkyl (preferably methyl) or $OC_{1-6}$alkyl (preferably methoxy). Thus preferred $R^4$ groups include the following:

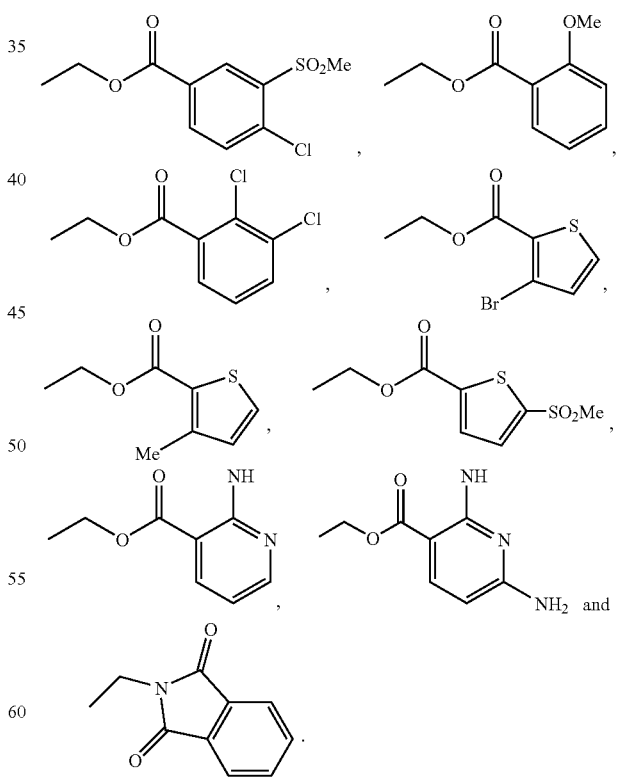

In another preferred embodiment, $R^4$ is selected from groups of the formula

—O—$(CH_2)_e$—$R^3$

wherein e is 0 or 1, and $R^3$ is selected from hydrogen, $C_{1-6}$alkyl (preferably methyl or n-butyl), aryl (preferably phenyl), trihalomethyl (preferably trifluoromethyl) or $C(O)R^7$ wherein $R^7$ is selected from $(CH_2)_m$-heteroaryl wherein m is 0 (preferably pyridyl) or substituted $(CH_2)_m$-aryl wherein m is 0 (preferably methylphenyl). Thus preferred $R^4$ groups include OH, OMe, O'Bu, $OCH_2Ph$, $OCH_2CF_3$, OC(O)(2-methylphenyl) and OC(O)(4-pyridyl); each of which is preferably substituted in the 5-position or the 6-position.

In another preferred embodiment, $R^4$ is selected from groups of the formula $C(O)NR^7R^8$ wherein $R^7$ and $R^8$ are each independently H, $C_{1-8}$alkyl, $C_{2-6}$alkenyl, $SO_2C_{1-6}$alkyl, $(CH_2)_m$—$C_{3-12}$cycloalkyl, $(CH_2)_m$-aryl, $(CH_2)_m$-heterocyclyl, $(CH_2)_m$-heterocyclyl substituted by $C_{1-6}$alkyl (preferably methyl), $(CH_2)_m$-heteroaryl, wherein m=0, 1, 2 or 3, or may, together with the nitrogen atom to which they are bound, form a heterocyclyl group. Thus preferred $R^4$ groups include $CONH_2$ and

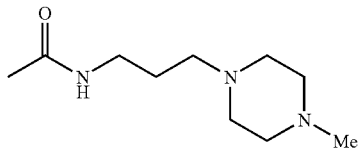

In another preferred embodiment, $R^4$ is selected from groups of the formula

wherein e is 0 to 6;

$R^3$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, phthalamido, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$ or $C(=NR^7)NR^7R^8$;

$R^7$ and $R^8$ are each independently H, $C_{1-8}$alkyl, $C_{2-6}$alkenyl, $SO_2C_{1-6}$alkyl, $(CH_2)_m$—$C_{3-12}$cycloalkyl, $(CH_2)_m$-aryl, $(CH_2)_m$-heterocyclyl, $(CH_2)_m$-heteroaryl, wherein m=0, 1 or 2, or may, together with the nitrogen atom to which they are bound, form a heterocyclyl group.

A specific group pf compounds of the invention are those of formula (Ia):

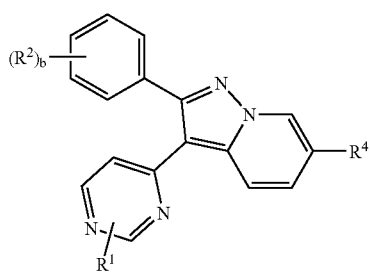

(Ia)

or a salt or solvate thereof or a physiologically functional derivative thereof:

wherein $R^1$ is a group of formula —NH—$(CH_2)_e$—$R^5$ wherein either:

(i) e=2, 3 or 4; and $R^5$ is $NR^7R^8$ wherein $R^7$ and $R^8$ are each independently selected from H, $C_{1-4}$alkyl, $S(O)_2C_{1-4}$alkyl, $(CH_2)_m$—$C_{3-8}$cycloalkyl, $(CH_2)_m$-aryl, $(CH_2)_m$-heterocyclyl, and $(CH_2)_m$-heteroaryl, wherein m=0, 1 or 2; or (ii) e=2, 3 or 4; and $R^5$ is $NR^7R^8$ wherein both $R^7$ and $R^8$ are taken together with the N atom to which they are bonded to form a heterocyclyl group; or (iii) e=1, 2 or 3; and $R^5$ is a nitrogen-containing heteroaryl or heterocyclyl group which is bonded to the alkylene portion of $R^1$ by an atom other than nitrogen;

wherein any of said alkyl, cycloalkyl, aryl, heterocyclyl and heteroaryl groups may be optionally further substituted by one or two groups selected from oxo, hydroxy, cyano, $S(O)C_{1-4}$alkyl, $S(O)_2C_{1-4}$alkyl, $OC_{1-4}$alkyl, $C_{1-4}$alkyl and $NR^9R^{10}$ wherein $R^9$ and $R^{10}$ are independently selected from H and $C_{1-4}$alkyl;

each $R^2$ is independently selected from hydrogen, CN, $OC_{1-4}$alkyl, halogen or trihalomethyl;

a is 1;

c is 1; and $R^4$ is selected from CN, halogen or trihalomethyl.

In a preferred embodiment of formula (Ia) $R^1$ is bonded to the 2-position of the pyrimidine ring as those positions are shown below:

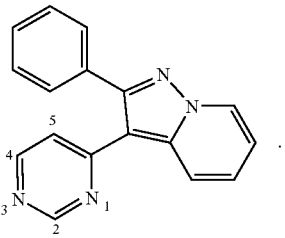

In another preferred embodiment of formula (Ia) $R^1$ is bonded to the 4-position of the pyrimidine ring as those positions are shown above.

In a preferred embodiment of formula (Ia), $R^1$ is a group of formula —NH—$(CH_2)_e$—$R^5$ wherein e is 2, 3 or 4 and $R^5$ is $NR^7R^8$ and wherein $R^7$ and $R^8$ are each independently selected from H, $C_{1-4}$alkyl, $S(O)_2C_{1-4}$alkyl, $(CH_2)_m$—$C_{3-8}$cycloalkyl, $(CH_2)_m$-aryl, $(CH_2)_m$-heterocyclyl, and $(CH_2)_m$-heteroaryl, wherein m is 0, 1 or 2.

In a further preferred embodiment of formula (Ia), $R^1$ is a group of formula —NH—$(CH_2)_e$—$R^5$ wherein e is 2, 3 or 4, preferably 3, and $R^5$ is $NR^7R^8$ wherein $R^7$ and $R^8$ are each independently selected from H and $C_4$alkyl. More preferably $R^7$ and $R^8$ are each independently selected from H, methyl, ethyl, n-propyl, isopropyl, and butyl. Most preferably $R^5$ is represented by a group selected from any one of the following: amino, methylamino, dimethylamino, ethylamino, diethylamino, n-propylamino, di(n-propyl)amino, iso-propylamino, di(isopropyl)amino and butylamino. In a further embodiment, any of said $C_{1-4}$alkyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^9R^{10}$ wherein $R^9$ and $R^{10}$ are each independently selected from H and $C_{1-4}$alkyl. A preferred substituent for said alkyl groups is $C_{1-4}$alkyl, more preferably n-butyl. Thus $R^5$ is preferably represented by the group n-octylamino.

In a further preferred embodiment of formula (Ia), $R^1$ is a group of formula —NH—$(CH_2)_e$—$R^5$ wherein e is 2, 3 or 4, preferably 3, and $R^5$ is $NR^7R^8$ wherein either $R^7$ or $R^8$ is represented by the group (CH$_2$)$_m$—C$_{3-8}$cycloalkyl wherein m is 0, 1 or 2, preferably 0 or 1, more preferably 0. More preferably, either R$^7$ or R$^8$ represent cyclopentyl or cyclohexyl. Most preferably R$^5$ is represented by a group selected from any one of the following: NH-cyclopentyl, NH—CH$_2$-cyclopentyl and NH-cyclohexyl. In a further embodiment, any of said C$_{3-8}$cycloalkyl groups may be optionally substituted by one or two groups selected from, oxo, hydroxy, cyano, S(O)C$_{1-4}$alkyl, S(O)$_2$C$_{1-4}$alkyl, OC$_{1-4}$alkyl, C$_{1-4}$alkyl and NR$^9$R$^{10}$ wherein R$^9$ and R$^{10}$ are each independently selected from H and C$_{1-4}$alkyl. A preferred substituent for said alkyl groups is C$_{1-4}$alkyl, more preferably methyl. Thus R$^5$ is preferably represented by the group NH-(3-methylcyclopentyl).

In a further preferred embodiment of formula (Ia), R$^1$ is a group of formula NH—(CH$_2$)$_e$—R$^5$ wherein e is 2, 3 or 4, preferably 3, and R$^5$ is NR$^7$R$^8$ wherein either R$^7$ or R$^8$ is represented by the group (CH$_2$)$_m$-aryl wherein m is 0, 1 or 2, preferably 0 or 1. More preferably, R$^7$ or R$^8$ represent phenyl or benzyl. Most preferably R$^5$ is represented by a group selected from any one of the following: N(Me)-phenyl and N(Me)-benzyl. In a further embodiment, any of said aryl groups may be optionally substituted by one or two groups selected from, oxo, hydroxy, cyano, S(O)C$_{1-4}$alkyl, S(O)$_2$C$_{1-4}$alkyl, OC$_{1-4}$alkyl, C$_{1-4}$alkyl and NR$^9$R$^{10}$ wherein R$^9$ and R$^{10}$ are each independently selected from H and C$_{1-4}$alkyl.

In a further preferred embodiment of formula (Ia), R$^1$ is a group of formula —NH—(CH$_2$)$_e$—R$^5$ wherein e is 2, 3 or 4, preferably 3, and R$^5$ is NR$^7$R$^8$ wherein either R$^7$ or R$^8$ is represented by the group (CH$_2$)$_m$-heterocyclyl wherein m is 0, 1 or 2, preferably 0 or 2. More preferably R$^7$ or R$^8$ represent piperidine, piperazine, morpholine, tetrahydropyran or tetrahydrothiopyran. Most preferably R$^5$ is represented by a group selected from any one of the following:

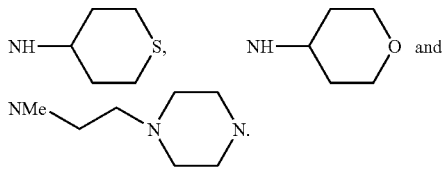

In a further embodiment, any of said heterocyclyl groups may be optionally substituted by one or two groups selected from, oxo, hydroxy, cyano, S(O)C$_{1-4}$alkyl, S(O)$_2$C$_{1-4}$alkyl, OC$_{1-4}$alkyl, C$_{1-4}$alkyl and NR$^9$R$^{10}$ wherein R$^9$ and R$^{10}$ are each independently selected from H and C$_{1-4}$alkyl.

In a further preferred embodiment of formula (Ia), R$^1$ is a group of formula —NH—(CH$_2$)$_e$—R$^5$ wherein e is 2, 3 or 4, preferably 3, and R$^5$ is NR$^7$R$^8$ wherein either R$^7$ or R$^8$ are represented by the group (CH$_2$)$_m$-heteroaryl wherein m is 0, 1 or 2, preferably 1. More preferably R$^7$ or R$^8$ represent furan, pyrrole, imidazole or pyridine. Most preferably R$^5$ is represented by the group:

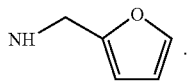

In a further embodiment of formula (Ia), any of said heteroaryl groups may be optionally substituted by one or two groups selected from, oxo, hydroxy, cyano, S(O)C$_{1-4}$alkyl, S(O)$_2$C$_{1-4}$alkyl, OC$_{1-4}$alkyl, C$_{1-4}$alkyl and NR$^9$R$^{10}$ wherein R$^9$ and R$^{10}$ are each independently selected from H and C$_{1-4}$alkyl.

In a further preferred embodiment of formula (Ia), R$^1$ is a group of formula —NH—(CH$_2$)$_e$—R$^5$ wherein e is 2, 3 or 4, preferably 3, and R$^5$ is NR$^7$R$^8$ wherein either R$^7$ or R$^8$ are represented by the group S(O)$_2$C$_{1-4}$alkyl. More preferably R$^7$ or R$^8$ represent S(O)$_2$Me. In a further embodiment, any of said C$_{1-4}$alkyl groups may be optionally substituted by one or two groups selected from, oxo, hydroxy, cyano, S(O)C$_{1-4}$ alkyl, S(O)$_2$C$_{1-4}$alkyl, OC$_{1-4}$alkyl, C$_{1-4}$alkyl and NR$^9$R$^{10}$ wherein R$^9$ and R$^{10}$ are each independently selected from H and C$_{1-4}$alkyl.

In a preferred embodiment of formula (Ia), R$^1$ is a group of formula —NH—(CH$_2$)$_e$—R$^5$ wherein e is 2, 3 or 4, preferably 2 or 3, more preferably 3, and R$^5$ is NR$^7$R$^8$ wherein both R$^7$ and R$^8$ are taken together with the N atom to which they are bonded to form a heterocyclyl group optionally fused to a benzene ring. Preferably, said heterocyclyl group is selected from piperidine, homopiperidine, piperazine, morpholine, pyrolidine and imidazolidine each of which may be optionally fused to a benzene ring. Most preferably R$^5$ is represented by a group selected from any one of the following:

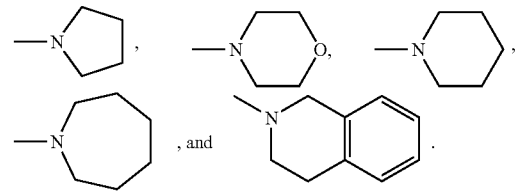

In a further embodiment of formula (Ia), any of said heterocyclyl groups may be optionally substituted by one or two groups selected from, oxo, hydroxy, cyano, S(O)C$_{1-4}$ alkyl, S(O)$_2$C$_{1-4}$alkyl, OC$_{1-4}$alkyl, C$_{1-4}$alkyl and NR$^9$R$^{10}$ wherein R$^9$ and R$^{10}$ are each independently selected from H and C$_{1-4}$alkyl. Preferred substituents for said alkyl groups are oxo and C$_{1-4}$alkyl, more preferably methyl, ethyl, propyl or iso-propyl. Thus R$^5$ is preferably represented by a group selected from any one of the following:

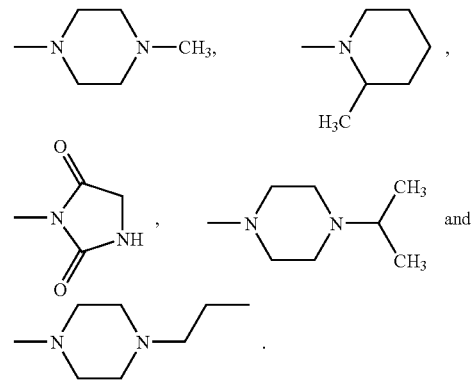

In a preferred embodiment of formula (Ia), R$^1$ is a group of formula —NH—(CH$_2$)$_n$—R$^5$ wherein n is 1, 2 or 3, preferably 1 or 2, and R$^5$ is a nitrogen-containing heteroaryl or heterocyclyl group which is bonded to the alkylene portion of R$^1$ by an atom other than nitrogen. Preferably R$^5$ is a heterocyclyl group selected from piperidine, homopiperidine, piperazine, morpholine, pyrolidine and imidazolidine or $R^5$ is a heteroaryl group selected from pyridine and imidazole. Most preferably $R^1$ is represented by a group selected from:

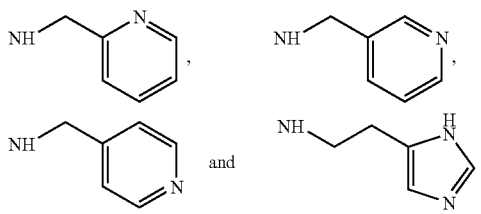

In a further embodiment of formula (Ia), any of said heteroaryl or heterocyclyl groups may be optionally substituted by one or two groups selected from, oxo, hydroxy, cyano, $S(O)C_{1-4}$alkyl, $S(O)_2C_{1-4}$alkyl, $OC_{1-4}$alkyl, $C_{1-4}$alkyl and $NR^9R^{10}$ wherein $R^9$ and $R^{10}$ are each independently selected from H and $C_{1-4}$alkyl.

In a preferred embodiment of formula (Ia) x is 1 or 2. In a more preferred embodiment the $R^2$ substituent(s) are in the meta- and/or para-position(s) relative to the bond to the pyrazolopyridine ring system. In a preferred embodiment, each $R^2$ is selected from chloro, fluoro and trifluoromethyl groups. In a more preferred embodiment, $(R^2)_b$ is represented by one or two substituents selected from F or Cl. In a further preferred embodiment, $(R^2)_b$ is represented by a $CF_3$ substituent. In a most preferred embodiment, $(R^2)_b$ and the phenyl ring to which such group(s) is/are bonded is selected from 3-chloro-4-fluorophenyl, 3-chlorophenyl, 4-fluorophenyl and 4-trifluoromethylphenyl. In an especially preferred embodiment, $(R^2)_b$ and the phenyl ring to which such group(s) is/are bonded is 4-fluorophenyl.

In a preferred embodiment of formula (Ia), $R^4$ is $CF_3$.

A specific group of compounds of formula (I) are those with the additional proviso that when Z is N and R' is in the 2-position of the pyrimidine ring it is not optionally substituted NH-phenyl.

Salts of the compounds of the present invention are also encompassed within the scope of the invention and may, for example, comprise acid addition salts resulting from reaction of an acid with a nitrogen atom present in a compound of formula (I).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

Examples of compounds of the invention wherein Z is CH include the following (Table 1):

TABLE 1

| Example # | Compound name |
|---|---|
| 1 | 2-(4-Fluorophenyl)-3-(4-pyridinyl)pyrazolo[1,5-a]pyridine |
| 2 | 2-(4-Fluorophenyl)-6-methyl-3-(4-pyridinyl)pyrazolo[1,5-a]pyridine |
| 3 | 2-(4-Fluorophenyl)-5-methyl-3-(4-pyridinyl)pyrazolo[1,5-a]pyridine |
| 4 | 2-(4-Fluorophenyl)-4-methyl-3-(4-pyridinyl)pyrazolo[1,5-a]pyridine |
| 5 | 2-(4-Fluorophenyl)-5-methoxy-3-(4-pyridinyl)pyrazolo[1,5-a]pyridine |
| 6 | 2-(4-Fluorophenyl)-5-hydroxymethyl-3-(4-pyridinyl)pyrazolo[1,5-a]-pyridine |
| 7 | 2-(4-Fluorophenyl)-4-hydroxymethyl-3-(4-pyridinyl)pyrazolo[1,5-a]-pyridine |
| 8 | 6-Fluoro-2-(4-fluorophenyl)-3-(4-pyridinyl)pyrazolo[1,5-a]pyridine |
| 9 | 4-Fluoro-2-(4-fluorophenyl)-3-(4-pyridinyl)pyrazolo[1,5-a]pyridine |
| 10 | [2-(4-Fluorophenyl)-3-(4-pyridinyl)pyrazolo[1,5-a]pyridin-5-yl]methyl 2-methylbenzoate |
| 11 | [2-(4-Fluorophenyl)-3-(4-pyridinyl)pyrazolo[1,5-a]pyridin-5-yl]methyl isonicotinate |
| 12 | [2-(4-Fluorophenyl)-3-(4-pyridinyl)pyrazolo[1,5-a]pyridin-5-yl]methyl nicotinate |
| 13 | [2-(4-Fluorophenyl)-3-(4-pyridinyl)pyrazolo[1,5-a]pyridin-5-yl]methyl 3-bromo-2-thiophenecarboxylate |
| 14 | [2-(4-Fluorophenyl)-3-(4-pyridinyl)pyrazolo[1,5-a]pyridin-5-yl]methyl 6-aminonicotinate |
| 15 | [2-(4-Fluorophenyl)-3-(4-pyridinyl)pyrazolo[1,5-a]pyridin-5-yl]methyl 5-(methylsulfonyl)-2-thiophenecarboxylate |
| 16 | [2-(4-Fluorophenyl)-3-(4-pyridinyl)pyrazolo[1,5-a]pyridin-5-yl]methyl 2-aminonicotinate |
| 17 | [2-(4-Fluorophenyl)-3-(4-pyridinyl)pyrazolo[1,5-a]pyridin-5-yl]methyl 3-(aminosulfonyl)-4-chlorobenzoate |
| 18 | [2-(4-Fluorophenyl)-3-(4-pyridinyl)pyrazolo[1,5-a]pyridin-5-yl]methyl 3-methyl-2-thiophenecarboxylate |

TABLE 1-continued

| Example # | Compound name |
|---|---|
| 19 | [2-(4-Fluorophenyl)-3-(4-pyridinyl)pyrazolo[1,5-a]pyridin-5-yl]methyl 2-methoxybenzoate |
| 20 | [2-(4-Fluorophenyl)-3-(4-pyridinyl)pyrazolo[1,5-a]pyridin-5-yl]methyl 2,3-dichlorobenzoate |
| 21 | 2-[2-(4-Fluorophenyl)-3-(4-pyridinyl)pyrazolo[1,5-a]pyridin-5-yl]-methyl-1H-isoindole-1,3(2H)-dione |
| 22 | [2-(4-Fluorophenyl)-3-(4-pyridinyl)pyrazolo[1,5-a]pyridin-5-yl]-methanamine |
| 23 | 2-(4-Fluorophenyl)-3-(4-pyridinyl)-6-(trifluoromethyl)pyrazolo[1,5-a]-pyridine |
| 24 | 2-(4-Fluorophenyl)-3-(4-pyridinyl)pyrazolo[1,5-a]pyridin-5-ol |
| 25 | 5-(n-Butoxy)-2-(4-fluorophenyl)-3-(4-pyridinyl)pyrazolo[1,5-a]-pyridine |
| 26 | 5-(Benzyloxy)-2-(4-fluorophenyl)-3-(4-pyridinyl)pyrazolo[1,5-a]pyridine |
| 27 | 2-(4-Fluorophenyl)-3-(2-fluoro-4-pyridinyl)pyrazolo[1,5-a]pyridine |
| 28 | 4-[2-(4-Fluorophenyl)pyrazolo[1,5-a]pyridin-3-yl]-N-[2-(1H-imidazol-5-yl)ethyl]-2-pyridinamine |
| 29 | N-Butyl-4-[2-(4-fluorophenyl)pyrazolo[1,5-a]pyridin-3-yl]-2-pyridinamine |
| 30 | 3-(4-[2-(4-Fluorophenyl)pyrazolo[1,5-a]pyridin-3-yl]-2-pyridinylamino)-1-propanol |
| 31 | N-(4-chlorobenzyl)-4-[2-(4-fluorophenyl)pyrazolo[1,5-a]pyridin-3-yl]-2-pyridinamine |
| 32 | $N^1$-4-[2-(4-Fluorophenyl)pyrazolo[1,5-a]pyridin-3-yl]-2-pyridinyl-1,3-propanediamine |
| 33 | 3-(2-Butoxy-4-pyridinyl)-2-(4-fluorophenyl)pyrazolo[1,5-a]pyridine |
| 34 | 4-[2-(4-Fluorophenyl)pyrazolo[1,5-a]pyridin-3-yl]-N-hexyl-2-pyridinamine |
| 35 | 4-[2-(4-Fluorophenyl)pyrazolo[1,5-a]pyridin-3-yl]-N-(4-methoxybenzyl)-2-pyridinamine |
| 36 | 4-[2-(4-Fluorophenyl)pyrazolo[1,5-a]pyridin-3-yl]-N-pentyl-2-pyridinamine |
| 37 | 4-[2-(4-Fluorophenyl)pyrazolo[1,5-a]pyridin-3-yl]-N-(3-pyridinylmethyl)-2-pyridinamine |
| 38 | 4-[2-(4-Fluorophenyl)pyrazolo[1,5-a]pyridin-3-yl]-N-propyl-2-pyridinamine |
| 39 | 4-[2-(4-Fluorophenyl)pyrazolo[1,5-a]pyridin-3-yl]-N-phenyl-2-pyridinamine |
| 40 | $N^1$-4-[2-(4-Fluorophenyl)pyrazolo[1,5-a]pyridin-3-yl]-2-pyridinyl-1,4-butanediamine |
| 41 | 2-(4-[2-(4-Fluorophenyl)pyrazolo[1,5-a]pyridin-3-yl]-2-pyridinylamino)-1-ethanol |
| 42 | N-Benzyl-4-[2-(4-fluorophenyl)pyrazolo[1,5-a]pyridin-3-yl]-2-pyridinamine |
| 43 | 4-[2-(4-Fluorophenyl)pyrazolo[1,5-a]pyridin-3-yl]-N,N-dimethyl-2-pyridinamine |
| 44 | 3-(2,6-Difluoro-4-pyridinyl)-2-(4-fluorophenyl)pyrazolo[1,5-a]pyridine |
| 45 | N-Benzyl-6-fluoro-4-[2-(4-fluorophenyl)pyrazolo[1,5-a]pyridin-3-yl]-2-pyridinamine |
| 46 | 2-(4-Fluorophenyl)-3-(2-fluoro-4-pyridinyl)-6-trifluoromethylpyrazolo[1,5-a]pyridine |
| 47 | 4-[2-(4-Fluorophenyl)-6-trifluoromethylpyrazolo[1,5-a]pyridin-3-yl]-N-isopropyl-2-pyridinamine |
| 48 | N-Cyclopropyl-4-[2-(4-fluorophenyl)-6-trifluoromethylpyrazolo[1,5-a]pyridin-3-yl]-2-pyridinamine |
| 49 | 3-(4-[2-(4-Fluorophenyl)-6-trifluoromethylpyrazolo[1,5-a]pyridin-3-yl]-2-pyridinylamino)-1-propanol |
| 50 | 6-Bromo-2-(4-fluorophenyl)-3-(2-fluoro-4-pyridinyl)pyrazolo[1,5-a]-pyridine |
| 51 | N-(3-Aminopropyl)-4-[6-bromo-2-(4-fluorophenyl)pyrazolo[1,5-a]pyridin-3-yl]-2-pyridinamine |
| 52 | 6-Cyano-2-(4-fluorophenyl)-3-(4-pyridinyl)pyrazolo[1,5-a]pyridine |
| 53 | 2-(4-Fluorophenyl)-3-(4-pyridinyl)pyrazolo[1,5-a]pyridine-6-carboxamide |
| 54 | 6-Cyano-2-(4-fluorophenyl)-3-(2-fluoro-4-pyridinyl)pyrazolo[1,5-a]pyridine |
| 55 | 6-Cyano-4-[2-(4-fluorophenyl)-pyrazolo[1,5-a]pyridin-3-yl]-N-cyclopropyl-2-pyridinamine |

Examples of compounds of the invention wherein Z is N include the following (Table 2):

TABLE 2

| Example # | Compound name |
| --- | --- |
| 56 | 2-(4-Fluorophenyl)-3-(4-pyrimidinyl)-pyrazolo[1,5-a]pyridine |
| 57 | 2-(4-Fluorophenyl)-3-(4-(2-methylthio)pyrimidinyl)-pyrazolo[1,5-a]pyridine |
| 58 | 2-(4-Fluorophenyl)-3-(4-(2-methylsulfinyl)pyrimidinyl)-pyrazolo[1,5-a]pyridine |
| 59 | 2-(4-Fluorophenyl)-3-(4-(2-methylsulfonyl)pyrimidinyl)-pyrazolo[1,5-a]pyridine |
| 60 | N-Butyl-4-[2-(4-fluorophenyl)pyrazolo[1,5-a]pyridin-3-yl]-2-pyrimidinamine |
| 61 | N-Cyclopropyl-4-[2-(4-fluorophenyl)pyrazolo[1,5-a]pyridin-3-yl]-2-pyrimidinamine |
| 62 | N-Benzyl-4-[2-(4-fluorophenyl)pyrazolo[1,5-a]pyridin-3-yl]-2-pyrimidinamine |
| 63 | 4-[2-(4-Fluorophenyl)pyrazolo[1,5-a]pyridin-3-yl]-N-(2-propyl)-2-pyrimidinamine |
| 64 | 4-[2-(4-Fluorophenyl)pyrazolo[1,5-a]pyridin-3-yl]-2-pyrimidinamine |
| 65 | 4-[2-(4-Fluorophenyl)-6-trifluoromethylpyrazolo[1,5-a]pyridin-3-yl]-2-pyrimidinamine |
| 66 | N-Butyl-4-[2-(4-fluorophenyl)-6-trifluoromethylpyrazolo[1,5-a]pyridin-3-yl]-2-pyrimidinamine |
| 67 | N-Benzyl-4-[2-(4-fluorophenyl)-6-trifluoromethylpyrazolo[1,5-a]pyridin-3-yl]-2-pyrimidinamine |
| 68 | N-Cyclopropyl-4-[2-(4-fluorophenyl)-6-trifluoromethylpyrazolo[1,5-a]pyridin-3-yl]-2-pyrimidinamine |
| 69 | 4-[2-(4-Fluorophenyl)-6-trifluoromethylpyrazolo[1,5-a]pyridin-3-yl]-N-(2-propyl)-2-pyrimidinamine |
| 70 | 4-[2-(4-Fluorophenyl)-6-trifluoromethylpyrazolo[1,5-a]pyridin-3-yl]-N-(2-propenyl)-2-pyrimidinamine |
| 71 | 4-[2-(4-Fluorophenyl)-6-trifluoromethylpyrazolo[1,5-a]pyridin-3-yl]-N-(2,2,2-trifluoroethyl)-2-pyrimidinamine |
| 72 | 3-(4-[2-(4-Fluorophenyl)-6-trifluoromethylpyrazolo[1,5-a]pyridin-3-yl]-2-pyrimidinylamino)-1-propanol |
| 73 | N-Cyclopropyl-4-[6-cyano-2-(4-fluorophenyl)pyrazolo[1,5-a]pyridin-3-yl]-2-pyrimidinamine |
| 74 | N-Cyclopropyl-4-[6-chloro-2-(4-fluorophenyl)pyrazolo[1,5-a]pyridin-3-yl]-2-pyrimidinamine |
| 75 | 2-(4-Fluorophenyl)-3-(4-(2-cyclopropylamino)pyrimidinyl)-6-pyrazolo[1,5-a]pyridinylcarboxamide |
| 76 | 2-(4-Fluorophenyl)-3-(4-(2-(3-hydroxypropyl)amino)pyrimidinyl)-6-pyrazolo[1,5-a]pyridinylcarboxamide |
| 77 | 2-(4-Fluorophenyl)-3-(4-(2-methylthio)pyrimidinyl)-6-trifluoromethylpyrazolo-[1,5-a]pyridine |
| 78 | 2-(4-Fluorophenyl)-3-(4-(2-methylsulfonyl)pyrimidinyl)-6-trifluoromethylpyrazolo-[1,5-a]pyridine |
| 79 | 2-(4-Fluorophenyl)-3-(4-(2-(3-(4-methylpiperazino)propyl)amino)pyrimidinyl)-6-pyrazolo-[1,5-a]pyridinylcarboxamide |
| 80 | 4-[2-(4-Fluorophenyl)pyrazolo[1,5-a]pyridin-3-yl]-N-[2-(1H-imidazol-5-yl)ethyl]-2-pyrimidinamine |
| 81 | 4-[2-(4-Fluorophenyl)pyrazolo[1,5-a]pyridin-3-yl]-N-(3-pyridinyl-methyl)-2-pyrimidinamine |
| 82 | 4-[2-(4-Fluorophenyl)pyrazolo[1,5-a]pyridin-3-yl]-N-(2-pyridinylmethyl)-2-pyrimidinamine |
| 83 | 4-[2-(4-Fluorophenyl)pyrazolo[1,5-a]pyridin-3-yl]-N-(4-pyridinyl-methyl)-2-pyrimidinamine |
| 84 | 2-(4-Fluorophenyl)-3-(2-phenoxypyrimidin-4-yl)-6-(trifluoromethyl)pyrazolo[1,5-a]pyridine |
| 85 | 3-({4-[2-(4-Fluorophenyl)-6-(trifluoromethyl)pyrazolo[1,5-a]pyridin-3-yl]pyrimidin-2-yl}oxy)-N,N-dimethylaniline |
| 86 | 3-[2-(2,5-Dimethylphenoxy)pyrimidin-4-yl]-2-(4-fluorophenyl)-6-(trifluoromethyl)pyrazolo[1,5-a]pyridine |

Examples of compounds of formula (Ia) include the following (Table 3) as well as salts or solvates thereof, particularly pharmaceutically acceptable salts or solvates thereof, or physiologically functional derivatives thereof:

TABLE 3

| Example # | Compound name |
| --- | --- |
| 87 | N-[3-(dimethylamino)propyl]-N-[4-{2-(4-fluorophenyl)-6-(trifluoromethyl)pyrazolo[1,5-a]pyridin-3-yl}pyrimidin-2-yl]amine |

TABLE 3-continued

| Example # | Compound name |
|---|---|
| 88 | N-[3-(dimethylamino)propyl]-N-[4-{6-(trifluoromethyl)-2-[4-(trifluoromethyl)phenyl]pyrazolo[1,5-a]pyridin-3-yl}pyrimidin-2-yl]amine |
| 89 | N-[4-{2-[3-chloro-4-fluorophenyl)-6-(trifluoromethyl)pyrazolo[1,5-a]pyridin-3-yl}pyrimidin-2-yl]-N-[3-(dimethylamino)propyl]amine |
| 90 | N-{4-[2-(3-chlorophenyl)-6-(trifluoromethyl)pyrazolo[1,5-a]pyridin-3-yl]pyrimidin-2-yl}-N-[3-(dimethylamino)propyl]amine |
| 91 | N-{4-[2-(4-fluorophenyl)-6-(trifluoromethyl)pyrazolo[1,5-a]pyridin-3-yl]pyrimidin-2-yl}-N-[2-(dimethylamino)ethyl]amine |
| 92 | N-[4-(diethylamino)butyl]-N-(4-{6-(trifluoromethyl)-2-[4-(trifluoromethyl)phenyl]pyrazolo[1,5-a]pyridin-3-yl}pyrimidin-2-yl)amine |
| 93 | N-{4-[2-(3-chloro-4-fluorophenyl)-6-(trifluoromethyl)pyrazolo[1,5-a]pyridin-3-yl]pyrimidin-2-yl}-N-[4-(diethylamino)butyl]amine |
| 94 | N-{4-[2-(3-chlorophenyl)-6-(trifluoromethyl)pyrazolo[1,5-a]pyridin-3-yl]pyrimidin-2-yl}-N-[4-(diethylamino)butyl]amine |
| 95 | N-[2-(diethylamino)ethyl]-N-(4-{6-(trifluoromethyl)-2-[4-(trifluoromethyl)phenyl]pyrazolo[1,5-a]pyridin-3-yl}pyrimidin-2-yl)amine |
| 96 | N-{4-[2-(3-chlorophenyl)-6-(trifluoromethyl)pyrazolo[1,5-a]pyridin-3-yl]pyrimidin-2-yl}-N-[2-(diethylamino)ethyl]amine |
| 97 | N-[2-(dipropylamino)ethyl]-N-(4-{6-(trifluoromethyl)-2-[4-(trifluoromethyl)phenyl]pyrazolo[1,5-a]pyridin-3-yl}pyrimidin-2-yl)amine |
| 98 | N-{4-[2-(3-chloro-4-fluorophenyl)-6-(trifluoromethyl)pyrazolo[1,5-a]pyridin-3-yl]pyrimidin-2-yl}-N-[2-(dipropylamino)ethyl]amine |
| 99 | N-{4-[2-(3-chlorophenyl)-6-(trifluoromethyl)pyrazolo[1,5-a]pyridin-3-yl]pyrimidin-2-yl}-N-[2-(dipropylamino)ethyl]amine |
| 100 | N-{4-[2-(3-chloro-4-fluorophenyl)-6-(trifluoromethyl)pyrazolo[1,5-a]pyridin-3-yl]pyrimidin-2-yl}-N-[2-(diisopropylamino)ethyl]amine |
| 101 | N-{4-[2-(3-chlorophenyl)-6-(trifluoromethyl)pyrazolo[1,5-a]pyridin-3-yl]pyrimidin-2-yl}-N-[2-(diisopropylamino)ethyl]amine |
| 102 | N-{4-[2-(4-fluorophenyl)-6-(trifluoromethyl)pyrazolo[1,5-a]pyridin-3-yl]pyrimidin-2-yl}-N-(2-pyrrolidin-1-ylethyl)amine |
| 103 | N-(2-pyrrolidin-1-ylethyl)-N-(4-{6-(trifluoromethyl)-2-[4-(trifluoromethyl)phenyl]pyrazolo[1,5-a]pyridin-3-yl}pyrimidin-2-yl)amine |
| 104 | N-{4-[2-(3-chloro-4-fluorophenyl)-6-(trifluoromethyl)pyrazolo[1,5-a]pyridin-3-yl]pyrimidin-2-yl}-N-(2-pyrrolidin-1-ylethyl)amine |
| 105 | N-{4-[2-(3-chlorophenyl)-6-(trifluoromethyl)pyrazolo[1,5-a]pyridin-3-yl]pyrimidin-2-yl}-N-(2-pyrrolidin-1-ylethyl)amine |
| 106 | N-{4-[2-(3-chlorophenyl)-6-(trifluoromethyl)pyrazolo[1,5-a]pyridin-3-yl]pyrimidin-2-yl}-N-(4-pyrrolidin-1-ylbutyl)amine |
| 107 | N-{4-[2-(4-fluorophenyl)-6-(trifluoromethyl)pyrazolo[1,5-a]pyridin-3-yl]pyrimidin-2-yl}-N-(2-piperidin-1-ylethyl)amine |
| 108 | N-(2-piperidin-1-ylethyl)-N-(4-{6-(trifluoromethyl)-2-[4-(trifluoromethyl)phenyl]pyrazolo[1,5-a]pyridin-3-yl}pyrimidin-2-yl)amine |
| 109 | N-{4-[2-(3-chloro-4-fluorophenyl)-6-(trifluoromethyl)pyrazolo[1,5-a]pyridin-3-yl]pyrimidin-2-yl}-N-(2-piperidin-1-ylethyl)amine |
| 110 | N-{4-[2-(3-chlorophenyl)-6-(trifluoromethyl)pyrazolo[1,5-a]pyridin-3-yl]pyrimidin-2-yl}-N-(2-piperidin-1-ylethyl)amin |
| 111 | N-{4-[2-(4-fluorophenyl)-6-(trifluoromethyl)pyrazolo[1,5-a]pyridin-3-yl]pyrimidin-2-yl}-N-(2-piperidin-1-ylpropyl)amine |
| 112 | N-(3-piperidin-1-ylpropyl)-N-(4-{6-(trifluoromethyl)-2-[4-(trifluoromethyl)phenyl]pyrazolo[1,5-a]pyridin-3-yl}pyrimidin-2-yl)amine |
| 113 | N-{4-[2-(3-chloro-4-fluorophenyl)-6-(trifluoromethyl)pyrazolo[1,5-a]pyridin-3-yl]pyrimidin-2-yl}-N-(3-piperidin-1-ylpropyl)amine |
| 114 | N-{4-[2-(3-chlorophenyl)-6-(trifluoromethyl)pyrazolo[1,5-a]pyridin-3-yl]pyrimidin-2-yl}-N-(3-piperidin-1-ylpropyl)amine |
| 115 | N-(2-azepan-1-ylethyl)-N-(4-{6-(trifluoromethyl)-2-[4-(trifluoromethyl)phenyl]pyrazolo[1,5-a]pyridin-3-yl}pyrimidin-2-yl)amine |
| 116 | N-(2-azepan-1-ylethyl)-N-{4-[2-(3-chloro-4-fluorophenyl)-6-(trifluoromethyl)pyrazolo[1,5-a]pyridin-3-yl]pyrimidin-2-yl}amine |
| 117 | N-(2-azepan-1-ylethyl)-N-{4-[2-(3-chlorophenyl)-6-(trifluoromethyl)pyrazolo[1,5-a]pyridin-3-yl]pyrimidin-2-yl}amine |
| 118 | N-{4-[2-(4-fluorophenyl)-6-(trifluoromethyl)pyrazolo[1,5-a]pyridin-3-yl]pyrimidin-2-yl}-N-(2-morpholin-4-ylethyl)amine |
| 119 | N-(2-morpholin-4-ylethyl)-N-(4-{6-(trifluoromethyl)-2-[4-(trifluoromethyl)phenyl]pyrazolo[1,5-a]pyridin-3-yl}pyrimidin-2-yl)amine |
| 120 | N-{4-[2-(3-chloro-4-fluorophenyl)-6-(trifluoromethyl)pyrazolo[1,5-a]pyridin-3-yl]pyrimidin-2-yl}-N-(2-morpholin-4-ylethyl)amine |
| 121 | N-(3-morpholin-4-ylpropyl)-N-(4-{6-(trifluoromethyl)-2-[4-(trifluoromethyl)phenyl]pyrazolo[1,5-a]pyridin-3-yl}pyrimidin-2-yl)amine |
| 122 | N-{4-[2-(3-chloro-4-fluorophenyl)-6-(trifluoromethyl)pyrazolo[1,5-a]pyridin-3-yl]pyrimidin-2-yl}-N-(3-morpholin-4-ylpropyl)amine |
| 123 | N-{4-[2-(3-chlorophenyl)-6-(trifluoromethyl)pyrazolo[1,5-a]pyridin-3-yl]pyrimidin-2-yl}-N-(3-morpholin-4-ylpropyl)amine |
| 124 | N-{4-[2-(4-fluorophenyl)-6-(trifluoromethyl)pyrazolo[1,5-a]pyridin-3-yl]pyrimidin-2-yl}-N-[3-(4-methylpiperazin-1-yl)propyl]amine |
| 125 | N-{4-[2-(3-chloro-4-fluorophenyl)-6-(trifluoromethyl)pyrazolo[1,5-a]-pyridin-3-yl]pyrimidin-2-yl}-N-[3-(4-methylpiperazin-1-yl)propyl]amine |

TABLE 3-continued

| Example # | Compound name |
|---|---|
| 126 | N-{4-[2-(4-fluorophenyl)-6-(trifluoromethyl)pyrazolo[1,5-a]pyridin-3-yl]pyrimidin-2-yl}-N-[2-(4-methylpiperazin-1-yl)ethyl]amine |
| 127 | N-[2-(4-propylpiperazin-1-yl)ethyl]-N-(4-{6-(trifluoromethyl)-2-[4-trifluoromethyl)phenyl]pyrazolo[1,5-a]pyridin-3-yl}pyrimidin-2-yl)amine |
| 128 | N-{4-[2-(3-chloro-4-fluorophenyl)-6-(trifluoromethyl)pyrazolo[1,5-a]pyridin-3-yl]pyrimidin-2-yl}-N-[2-(4-propylpiperazin-1-yl)ethyl]amine |
| 129 | N-{4-[2-(3-chlorophenyl)-6-(trifluoromethyl)pyrazolo[1,5-a]pyridin-3-yl]pyrimidin-2-yl}-N-[2-(4-propylpiperazin-1-yl)ethyl]amine |

Examples of preferred compounds of formula (Ia) include the following (Table 4) as well as salts or solvates thereof, particularly pharmaceutically acceptable salts or solvates thereof, or physiologically functional derivatives thereof:

TABLE 4

| Example # | Compound name |
|---|---|
| 89 | N-[4-{2-[3-chloro-4-fluorophenyl]-6-(trifluoromethyl)pyrazolo[1,5-a]pyridin-3-yl}pyrimidin-2-yl]-N-[3-(dimethylamino)propyl]amine |
| 90 | N-{4-[2-(3-chlorophenyl)-6-(trifluoromethyl)pyrazolo[1,5-a]pyridin-3-yl]pyrimidin-2-yl}-N-[3-(dimethylamino)propyl]amine |
| 93 | N-{4-[2-(3-chloro-4-fluorophenyl)-6-(trifluoromethyl)pyrazolo[1,5-a]pyridin-3-yl]pyrimidin-2-yl}-N-[4-(diethylamino)butyl]amine |
| 94 | N-{4-[2-(3-chlorophenyl)-6-(trifluoromethyl)pyrazolo[1,5-a]pyridin-3-yl]pyrimidin-2-yl}-N-[4-(diethylamino)butyl]amine |
| 96 | N-{4-[2-(3-chlorophenyl)-6-(trifluoromethyl)pyrazolo[1,5-a]pyridin-3-yl]pyrimidin-2-yl}-N-[2-(diethylamino)ethyl]amine |
| 98 | N-{4-[2-(3-chloro-4-fluorophenyl)-6-(trifluoromethyl)pyrazolo[1,5-a]pyridin-3-yl]pyrimidin-2-yl}-N-[2-(dipropylamino)ethyl]amine |
| 100 | N-{4-[2-(3-chloro-4-fluorophenyl)-6-(trifluoromethyl)pyrazolo[1,5-a]pyridin-3-yl]pyrimidin-2-yl}-N-[2-(diisopropylamino)ethyl]amine |
| 106 | N-{4-[2-(3-chlorophenyl)-6-(trifluoromethyl)pyrazolo[1,5-a]pyridin-3-yl]pyrimidin-2-yl}-N-(4-pyrrolidin-1-ylbutyl)amine |
| 113 | N-{4-[2-(3-chloro-4-fluorophenyl)-6-(trifluoromethyl)pyrazolo[1,5-a]pyridin-3-yl]pyrimidin-2-yl}-N-(3-piperidin-1-ylpropyl)amine |
| 117 | N-(2-azepan-1-ylethyl)-N-{4-[2-(3-chlorophenyl)-6-(trifluoromethyl)pyrazolo[1,5-a]pyridin-3-yl]pyrimidin-2-yl}amine |
| 120 | N-{4-[2-(3-chloro-4-fluorophenyl)-6-(trifluoromethyl)pyrazolo[1,5-a]pyridin-3-yl]pyrimidin-2-yl}-N-(2-morpholin-4-ylethyl)amine |
| 122 | N-{4-[2-(3-chlorophenyl)-6-(trifluoromethyl)pyrazolo[1,5-a]pyridin-3-yl]pyrimidin-2-yl}-N-(3-morpholin-4-ylpropyl)amine |
| 123 | N-{4-[2-(3-chlorophenyl)-6-(trifluoromethyl)pyrazolo[1,5-a]pyridin-3-yl]pyrimidin-2-yl}-N-(3-morpholin-4-ylpropyl)amine |
| 124 | N-{4-[2-(4-fluorophenyl)-6-(trifluoromethyl)pyrazolo[1,5-a]pyridin-3-yl]pyrimidin-2-yl}-N-[3-(4-methylpiperazin-1-yl)propyl]amine |
| 125 | N-{4-[2-(3-chloro-4-fluorophenyl)-6-(trifluoromethyl)pyrazolo[1,5-a]pyridin-3-yl]pyrimidin-2-yl}-N-[3-(4-methylpiperazin-1-yl)propyl]amine |
| 128 | N-{4-[2-(3-chloro-4-fluorophenyl)-6-(trifluoromethyl)pyrazolo[1,5-a]pyridin-3-yl]pyrimidin-2-yl}-N-[2-(4-propylpiperazin-1-yl)ethyl]amine |
| 129 | N-{4-[2-(3-chlorophenyl)-6-(trifluoromethyl)pyrazolo[1,5-a]pyridin-3-yl]pyrimidin-2-yl}-N-[2-(4-propylpiperazin-1-yl)ethyl]amine |

Examples of particularly preferred compounds of formula (Ia) include the following (Table 5) as well as salts or solvates thereof, particularly pharmaceutically acceptable salts or solvates thereof, or physiologically functional derivatives thereof:

TABLE 5

| Example # | Compound name |
|---|---|
| 93 | N-{4-[2-(3-chloro-4-fluorophenyl)-6-(trifluoromethyl)pyrazolo[1,5-a]pyridin-3-yl]pyrimidin-2-yl}-N-[4-(diethylamino)butyl]amine |
| 94 | N-{4-[2-(3-chlorophenyl)-6-(trifluoromethyl)pyrazolo[1,5-a]pyridin-3-yl]pyrimidin-2-yl}-N-[4-(diethylamino)butyl]amine |
| 106 | N-{4-[2-(3-chlorophenyl)-6-(trifluoromethyl)pyrazolo[1,5-a]pyridin-3-yl]pyrimidin-2-yl}-N-(4-pyrrolidin-1-ylbutyl)amine |

TABLE 5-continued

| Example # | Compound name |
|---|---|
| 123 | N-{4-[2-(3-chlorophenyl)-6-(trifluoromethyl)pyrazolo[1,5-a]pyridin-3-yl]pyrimidin-2-yl}-N-(3-morpholin-4-ylpropyl)amine |
| 124 | N-{4-[2-(4-fluorophenyl)-6-(trifluoromethyl)pyrazolo[1,5-a]pyridin-3-yl]pyrimidin-2-yl}-N-[3-(4-methylpiperazin-1-yl)propyl]amine |
| 125 | N-{4-[2-(3-chloro-4-fluorophenyl)-6-(trifluoromethyl)pyrazolo[1,5-a]-pyridin-3-yl]pyrimidin-2-yl}-N-[3-(4-methylpiperazin-1-yl)propyl]amine |
| 128 | N-{4-[2-(3-chloro-4-fluorophenyl)-6-(trifluoromethyl)pyrazolo[1,5-a]pyridin-3-yl]pyrimidin-2-yl}-N-[2-(4-propylpiperazin-1-yl)ethyl]amine |
| 129 | N-{4-[2-(3-chlorophenyl)-6-(trifluoromethyl)pyrazolo[1,5-a]pyridin-3-yl]pyrimidin-2-yl}-N-[2-(4-propylpiperazin-1-yl)ethyl]amine |

A particularly prefferred compound of formula (I) is 3-(4-[2-(4-fluorophenyl)-6-trifluoromethylpyrazolo[1,5-a]pyridin-3-yl]-2-pyrimidinylamino)-1-propanol.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing the compounds of Formula (I) comprises the reaction of a compound of Formula (VII)

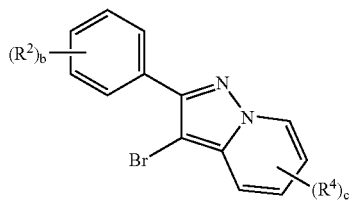

(VII)

with a compound of general Formula (VIII) or (IX)

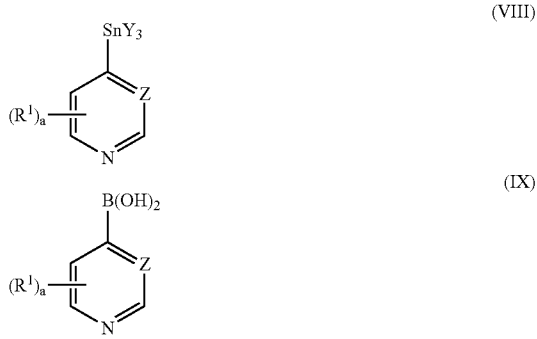

(VIII)

(IX)

wherein Z is CH or N and Y is methyl or butyl.

This general method (A) can be conveniently performed by mixing the two compounds in an inert solvent, in the presence of a palladium catalyst, and optionally heating the mixture to about 100° C. Preferably the reaction is performed using an approximately equimolar mixture of (VII) and (VIII), or an approximately equimolar mixture of (VII) and (IX). The palladium catalyst is preferably present in the proportion of 1–5 mol % compared to (VII). Palladium catalysts which may be used include, but are not limited to, tetrakistriphenylphosphine palladium(O), bis(triphenylphosphine)palladium dichloride. When one of the reactant partners is a compound of general formula (IX), the reaction is more conveniently carried out by adding a base in a proportion equivalent to, or greater than, that of (IX). Preferably the base is a trialkylamine or sodium hydrogen carbonate.

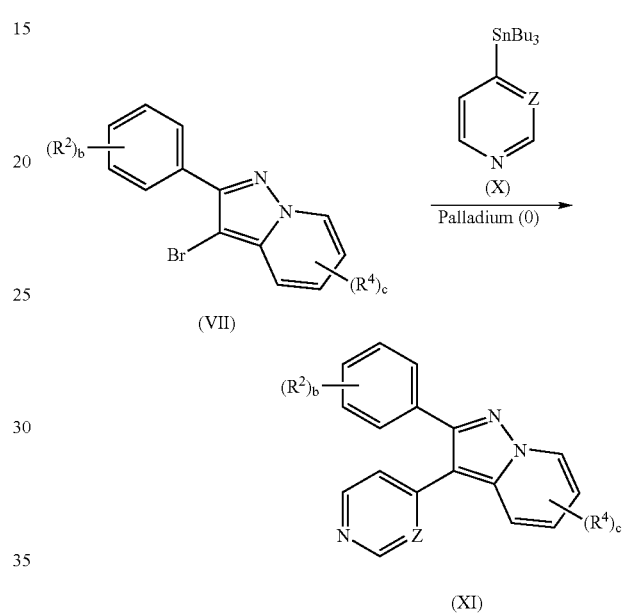

Another general method (B) for the preparation of the compounds of this invention is the reaction of a compound of Formula (VII) with a compound of Formula (X) as summarized below to give compounds of Formula (I) where $R^1$ is hydrogen.

The type of reaction utilized in general method (B) is well documented in the literature and is routinely referred to as a 'Stille' coupling (Stille, Angew. Chem. Int. Ed. Engl. 1986, 25, 508). This reaction is brought about by mixing the two reactants in an inert solvent in the presence of a catalytic quantity of a palladium species and heating the reaction mixture. Conveniently the solvent is, for example, toluene, dioxane, tetrahydrofuran or dimethylformamide and the palladium catalyst is a palladium(0) species, or a convenient precursor thereof, for example, tetrakis(triphenylphosphine) palladium(0) or bis(triphenylphosphine) palladium dichloride. For example, when $R^4$ is hydrogen, the reaction is most conveniently performed by mixing the two reactants, in an approximate equimolar ratio, in toluene, adding an amount of tetrakis(triphenylphosphine)palladium(0) equal to about 5 mol % of that of (VII), and heating the mixture at about 100–120° C. until the reaction is judged complete by the disappearance of either (VII) or (X). Typically this reaction requires between 12 and 48 h to proceed to completion. The product can be conveniently isolated using procedures typical for this Stille coupling procedure.

One skilled in the art will recognize that a similar reaction, illustrated below in general method (C) can be used to prepare compounds of the invention using boron containing reactants such as (XII).

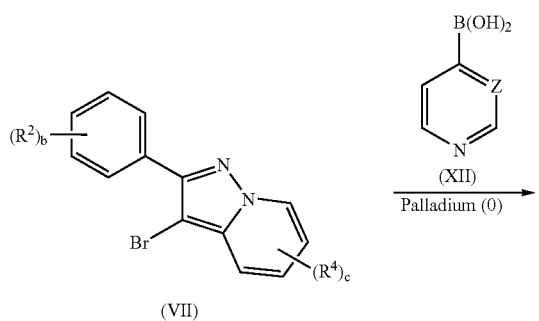

(VII)

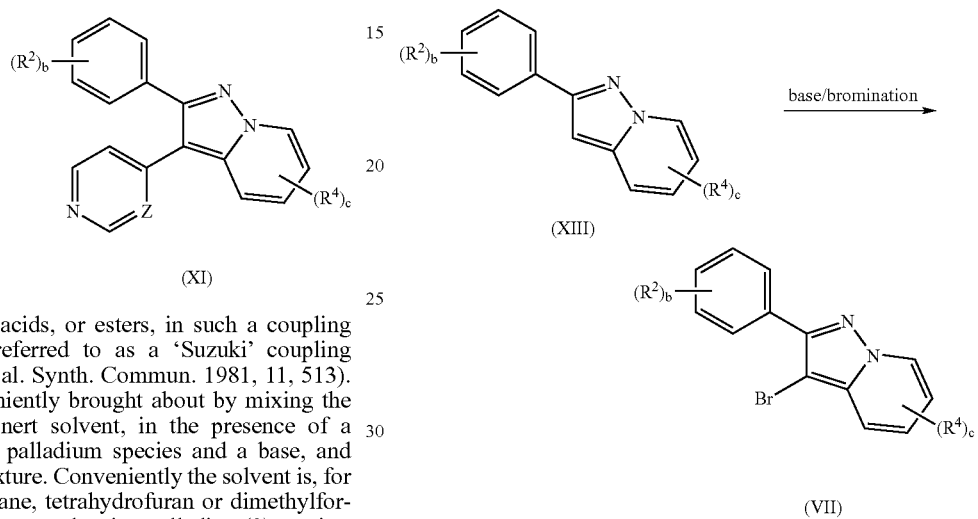

The use of boronic acids, or esters, in such a coupling reaction is typically referred to as a 'Suzuki' coupling reaction (Suzuki, A. et al. Synth. Commun. 1981, 11, 513). Said reaction is conveniently brought about by mixing the two reactants, in an inert solvent, in the presence of a catalytic quantity of a palladium species and a base, and heating the reaction mixture. Conveniently the solvent is, for example, toluene, dioxane, tetrahydrofuran or dimethylformamide and the palladium catalyst is a palladium(0) species, or a convenient precursor thereof, for example, tetrakis (triphenylphosphine) palladium(0) or bis(triphenylphosphine)palladium dichloride, and the base is sodium bicarbonate or a trialkyl amine such as triethyl amine.

Boron containing compounds such as (XII) and tin containing compounds such as (X) are either commercially available or can be prepared using methods known to one skilled in the art (Stille, *Angew. Chem. Int. Ed. Engl.* 1986, 25, 508; Snieckus, V. et al. *J. Org. Chem.* 1995, 60, 292–6).

Compounds of general formula (VII) may be conveniently prepared from compounds of Formula (XII) by a decarboxylation/bromination sequence as shown below.

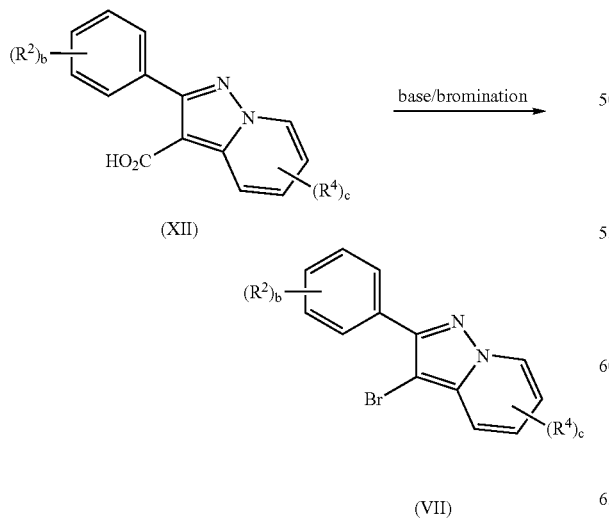

This reaction can be achieved by treatment of a compound of general formula (XII), dissolved in a suitable solvent, with a base followed by a brominating agent and stirring the mixture at, or about, 25° C. until the reaction is judged complete by the disappearance of (XII). Suitable solvents include, but are not limited to, dimethylformamide, dimethylacetamide, dioxane and the like. Conveniently the base is sodium hydrogen carbonate and the brominating agent can be, for example, N-bromosuccinimide. Alternatively, compounds of general formula (VII) can be conveniently prepared by treatment of a compound of general formula (XIII) with a brominating agent as summarized below.

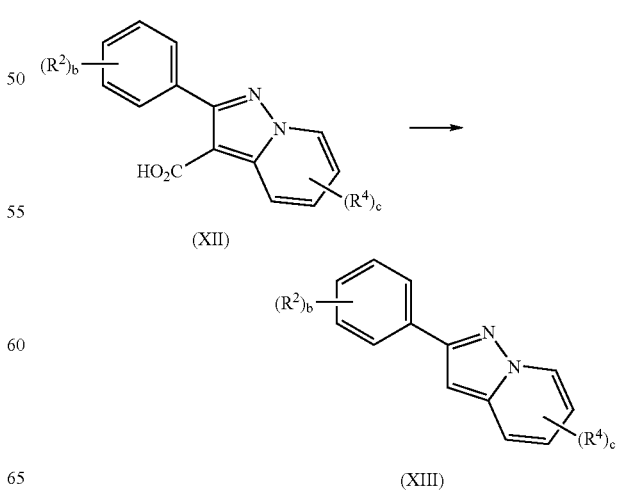

This reaction can be easily carried out by dissolving the compound of general formula (XIII) in an inert solvent and adding to the solution a brominating agent in sufficient quantity to effect complete reaction of (XIII). Preferably the solvent is dimethylformamide, dimethylacetamide, dioxane and the like and brominating agents include, but are not limited to, bromine, N-bromosuccinimide, N-bromoacetamide and the like.

Compounds of general formula (XIII) may be conveniently prepared by the decarboxylation of a compound of general formula (XII) as summarized below.

Said decarboxylation may be carried out by any one of a variety of methods described in the literature for similar decarboxylations. For example: heating a solution of a compound of general formula (XII) in an inert solvent, or conversion to a 'Barton ester' followed by treatment with a radical reductant, for example tributyltin hydride (Crich, D. *Aldrichimica Acta*, 1987, 20, 35).

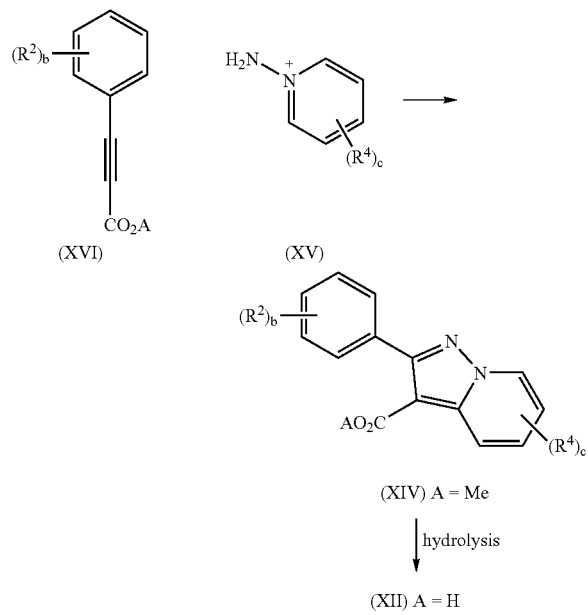

Compounds of general formula (XII) can be prepared most readily by simple hydrolysis of lower alkyl esters of general formula (XIV). Esters such as (XIV) are commonly referred to as pyrazolo[1,5-a]pyridines (Hardy, C. R. *Adv. Het. Chem.* 1984, 36, 343) and may be prepared by a cycloaddition reaction between compounds of general formula (XV) and acetylenes of general formula (XVI), as summarized below.

Cycloaddition reactions such as these are commonly known as [3+2] dipolar cycloaddition reactions. Conveniently the reaction may be carried out by mixing the reactants (XV) and (XVI), in equimolar amounts, in an inert solvent and adding a suitable base. The mixture is then stirred at between 20–100° C. until the reaction is judged complete by the disappearance of one of the reactants. Preferred solvents include but are not limited to acetonitrile, dioxane, tetrahydrofuran, dimethylformamide and the like. Preferred bases include non-nucleophilic amines such as 1,8-diazabicyclo[5.4.0]undec-7-ene, 1,5-diazabicyclo[4.3.0]non-5-ene, 1,4-diazabicyclo[2.2.2]octane and the like.

Esters such as those of Formula (XIV) can be conveniently hydrolyzed to their corresponding carboxylic acids by standard hydrolysis conditions employed to effect similar hydrolysis reactions (Larock, Comprehensive Organic Transformations, 1989, 981). For example, treatment of a solution of a compound of general formula (XIV) in a lower alcohol, for example methanol, with sodium hydroxide followed by heating the mixture for an appropriate time gives the compound of general formula (XII).

Compounds of general formula (XV) are aminated pyridine derivatives and are either commercially available or can be conveniently prepared by reacting a suitable pyridine with an aminating reagent such as O-(mesitylsulfonyl)hydroxylamine, O-(diphenylphosphinyl)hydroxylamine and the like.

Acetylenic esters such as those of general formula (XVI) are either known compounds or can be prepared by methods described in the literature. Preferred methods include the reaction of acetylenes such as those of general formula (XVII) with a suitable base to generate an acetylenic anion and subsequent reaction of the anion with an alkoxycarbonylating agent, as summarized below.

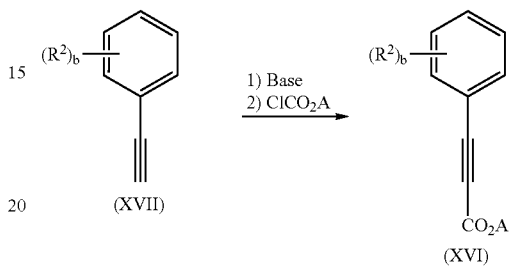

Preferably the acetylene (XVII) is dissolved in an inert solvent, such as tetrahydrofuran, and the solution is cooled to about −75° C. A non-nuclephilic base is added in sufficient quantity to effect deprotonation of the acetylene (XVII). The preferred bases include, but are not limited to, n-butyllithium, lithium diisopropylamide, sodium bis(trimethylsilyl)amide and the like. To the reaction mixture is then added a reagent capable of reacting with an anion to introduce an alkoxycarbonyl group. Preferred reagents include, but are not limited to, methyl chloroformate, ethyl chloroformate, benzyl chloroformate and the like.

Arylalkynes such as (XVII) are either known compounds or can be prepared by literature methods such as those described in, for example, Negishi, E. *J. Org. Chem.* 1997, 62, 8957.

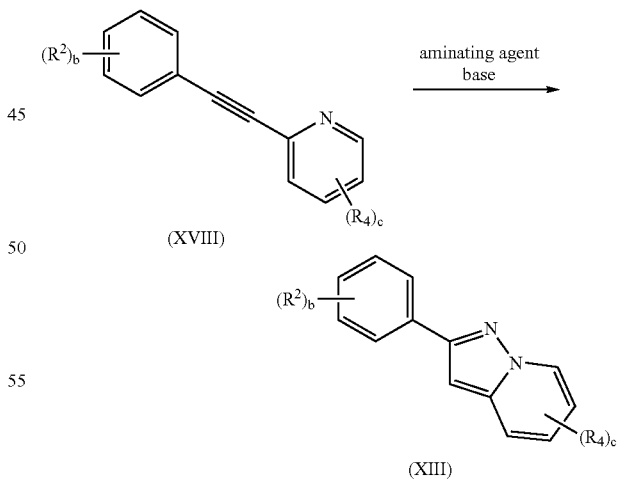

Compounds of general formula (XIII) can also be prepared via a number of other convenient routes. Disubstituted acetylenes as represented by formula (XVIII) can be treated with an aminating agent, optionally in the presence of a base, to give compounds of general formula (XIII). The aminating agent is, preferably, O-(mesitylsulfonyl)hydroxylamine and the base is potassium carbonate.

Disubstituted acetylenes such as (XVIII) are readily prepared by a palladium catalyzed coupling reaction between aryl acetylenes and 2-halopyridines using methods described in the literature (Yamanake et. al, *Chem. Pharm. Bull.* 1988, 1890).

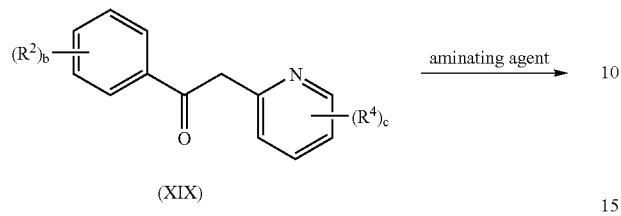

(XIX)

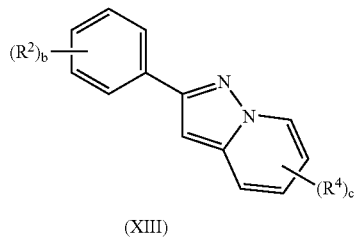

(XIII)

An alternative synthesis of compounds of general formula (XIII) involves treating a ketone of general formula (XIX) with an aminating agent in a suitable solvent and optionally heating the reaction. The aminating agent is, preferably, O-(mesitylsulfonyl)hydroxylamine and preferred solvents include chloroform, dichloromethane and the like.

Ketones such as those of general formula (XIX) can be readily prepared using procedures described in the literature (Cassity, R. P.; Taylor, L. T.; Wolfe, J. F. *J. Org. Chem.* 1978, 2286). A more preferred approach to compounds of general formula (XII) involves the conversion of ketones of general formula (XIX) to oximes such as (XX) followed by treatment of said oximes with an aminating agent. Typically, oximes of general formula (XX) are readily prepared by treating ketones of general formula (XIX) with a source of hydroxylamine, in an appropriate solvent, and optionally in the presence of a base. Preferably the source of hydroxylamine is hydroxylamine hydrochloride and the base is sodium carbonate, potassium carbonate, or an aqueous solution of sodium hydroxide. Preferred solvents include lower alcohols, such as methanol and ethanol, or acetonitrile. The aminating agent is, preferably, O-(mesitylsulfonyl)hydroxylamine and preferred solvents include chloroform, dichloromethane and the like.

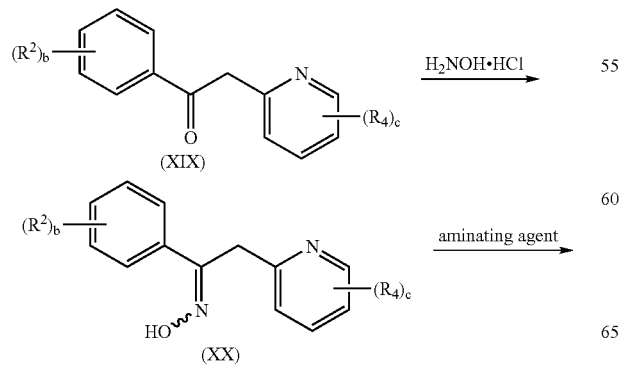

-continued

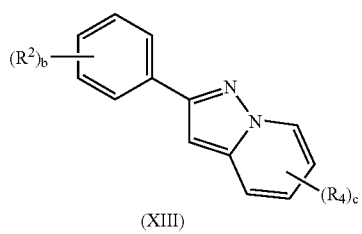

(XIII)

A still more preferred method for the preparation of compounds of general formula (XIII) from oximes of general formula (XX) involves the treatment of the said oximes with an acylating or sulfonylating agent in the presence of a base to generate azirines of general formula (XXI). Azirines such as (XXI) can be rearranged to compounds of general formula (XIII) by heating a solution of said azirine in a suitable solvent at temperatures of about −100–180° C. More preferably the rearrangement is carried out in the presence of $FeCl_2$. In the presence of $FeCl_2$ the rearrangement occurs at lower temperatures and in a higher yield. Typically the azirines (XXI) can be prepared by treatment of oximes of general formula (XX) with acetic anhydride, trifluoroacetic anhydride, methanesulfonyl chloride, toluenesulfonyl chloride and the like in an inert solvent, for example, chloroform, dichloromethane or toluene. Preferred bases include, but are not limited to, triethylamine, diisopropylethylamine, pyridine and the like.

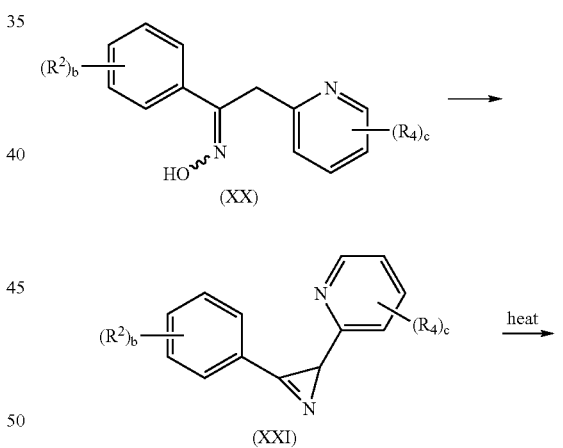

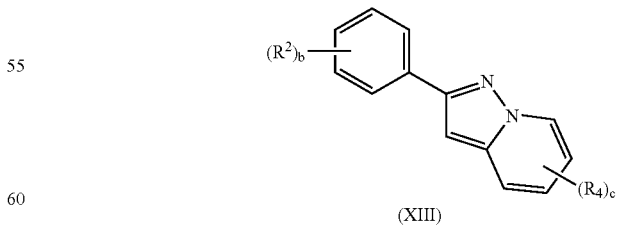

(XIII)

A general method (D) for the preparation of compounds of general formula (V) comprises the reaction of a compound of formula (XXII) with a compound of general formula (XXIII).

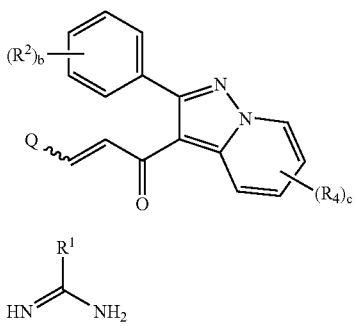

wherein Q is alkyloxy, alkylthio or dialkylamino.

The general method (D) can be readily carried out by mixing a compound of general formula (XXII) with a compound of general formula (XXIII) in a suitable solvent, optionally in the presence of a base, and heating the reaction mixture to about 50–150° C. Typically the solvent is a lower alcohol such as methanol, ethanol, isopropanol and the like, and the base can be, for example, a sodium alkoxide, potassium carbonate or an amine base such as triethylamine.

Compounds of general formula (XXII) may be conveniently prepared by reacting a compound of general formula (XXIV) with a dimethylformamide dialkylacetal, to give compounds of formula (XXII) wherein Q is $Me_2N$, or with a trialkyl orthoformate or a dialkoxymethyl acetate, to give compounds of formula (XXII) wherein Q is an alkoxy group. Conveniently, a dimethylformamide dialkylacetal is dimethylformamide dimethyl acetal or dimethylformamide di-tertbutyl acetal and the reaction carried out by mixing the compound of general formula (XXIV) with the dimethylformamide dialkylacetal and optionally heating the reaction. Preferred trialkyl orthoformates include trimethyl orthoformate and triethyl orthoformate. In a similar manner, diethoxymethyl acetate can be employed to prepare compounds of general formula (XXII) wherein Q is EtO—.

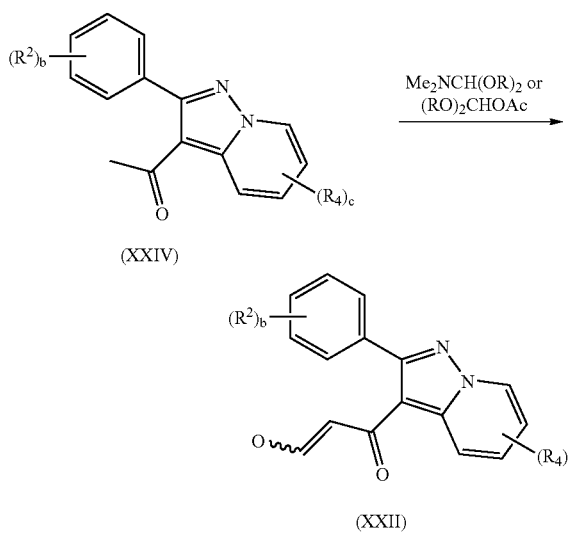

Compounds of general formula (XXIV) can be prepared from compounds of formula (XIII) by an acylation procedure. Typically the acylation is conveniently carried out by treating the compounds of formula (XIII) with an acylating agent optionally in the presence of an acid catalyst. The preferred acylating agent is acetic anhydride and a convenient acid is sulfuric acid.

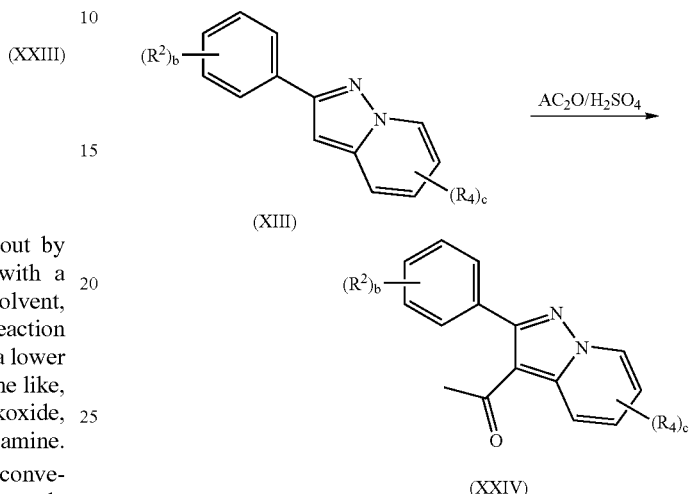

Methods for the synthesis of compounds of formula (XIII) are described above.

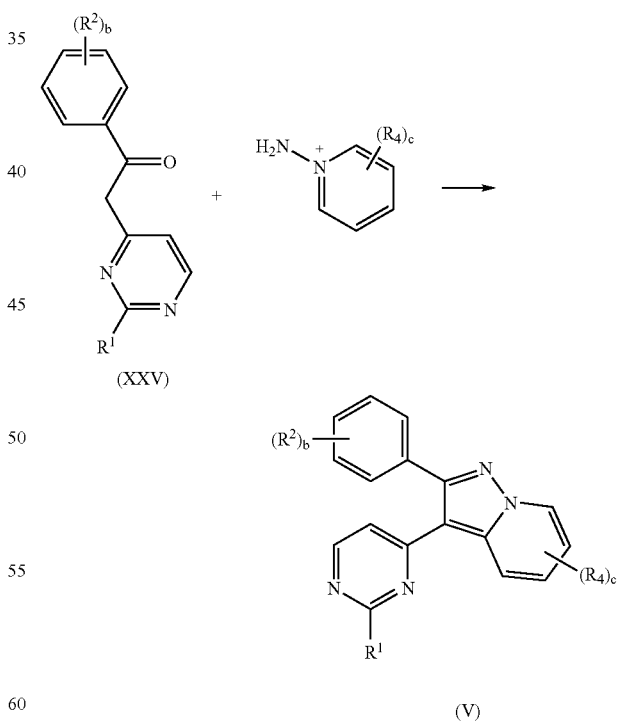

Certain compounds of general formula (V) may be conveniently prepared by a process which involves reacting a ketone of general formula (XXV) with an N-aminopyridine derivative in the presence of an acid or a base. Typically the acid is p-toluenesulfonic acid and the base can be potassium carbonate, sodium hydroxide, caesium carbonate, lithium hydroxide, triethylamine, potassium tert-butoxide.

Compounds of general formula (I) can also be converted to alternate compounds of general formula (I).

Compounds of general formula (I) wherein $R^1$ is a leaving group, for example a halogen such as chloride, or a sulfone such as methanesulfonyl can be converted into compounds of general formula (I) wherein $R^1$ is an ether or an amino group by treatment of said chloro, or methanesulfonyl derivative with alcohols or amines. Thus, a particularly preferred method for synthesising compounds of general formula (V) wherein $R^1$ is $-NH-(CH_2)_e-R^5$ is shown below. A compound of general formula (XXVI) is mixed at room temperature with a neat amine of general formula $H_2N-(CH_2)_e-R_5$. The mixture is then heated with an airgun until a homogenoeous melt is obtained. This usually takes about 0.2 minutes. Upon cooling, water is added and the compound of general formula (I) precipitates out and may be separated by filtration.

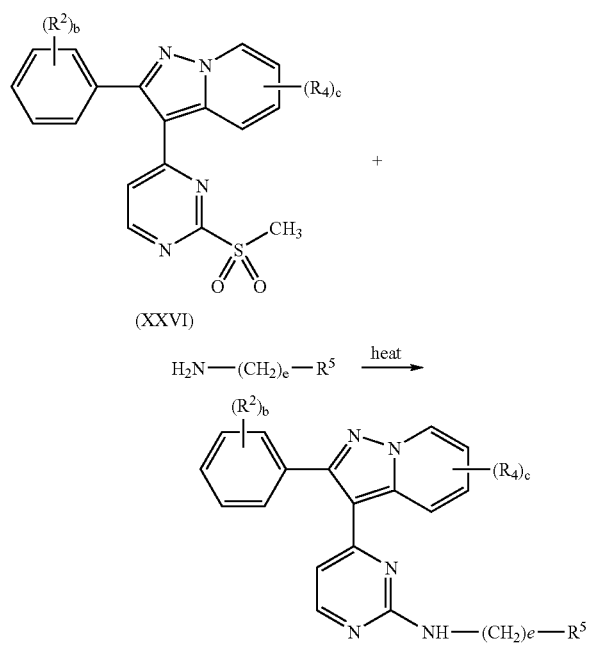

Compounds of general formula (XXVI) may be produced by the reaction of oxone with compounds of general formula (XXVII) as shown below.

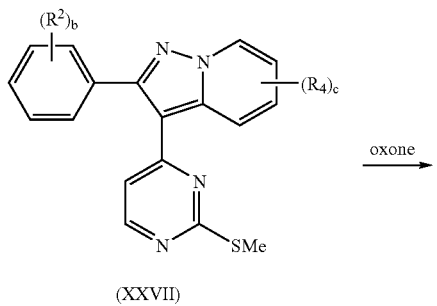

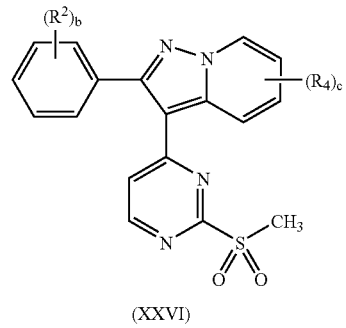

Compounds of general formula (XXVII) may be produced by reaction of a compound of formula (VII) with a compound of formula (VIII) wherein Z is N, $R^1$ is —SMe and Y is butyl. The synthesis of a compound of formula (VIII) wherein Z is N, $R^1$ is —SMe and Y is butyl is described in the literature (Sandosham, J. and Undheim, K. *Tetrahedron* 1994, 50, 275; Majeed, A. J. et al *Tetrahedron* 1989, 45, 993).

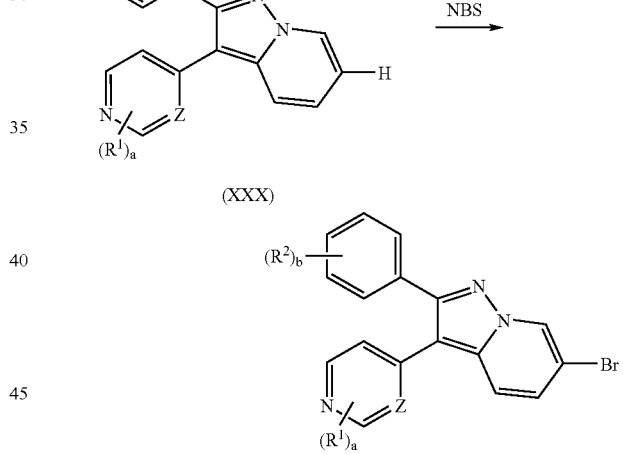

Compounds of general formula (I), wherein $R^4$ is hydrogen can be converted into compounds wherein $R^4$ is bromide or iodide and is attached to position 6. Said conversion is conveniently carried out by addition of a brominating agent such as N-bromosuccinimide, or an iodinating agent such as N-iodosuccinimide, to a solution of a compound of general formula (XXX) in an appropriate solvent. Preferred solvents include dimethylformamide, dichloromethane and the like.

Compounds of general formula (I), wherein $R^4$ is a bromide or iodide and is attached to position 6 can be converted to compounds with different substitutions at position 6 by a variety of methods. For example, treatment of a compound of general formula (XXXI), wherein $R^4$ is bromide or iodide, under conditions well known in the art as Stille coupling reactions or Suzuki coupling reactions leads to compounds wherein $R^4$ is alkyl, alkenyl, alkynyl, aryl, heteroaryl, cyano, carboalkoxy, or alkylamino.

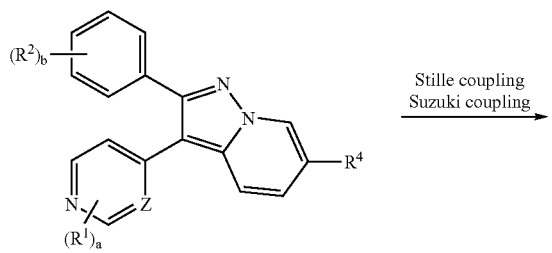

(XXXI)

R⁴ = Br, I

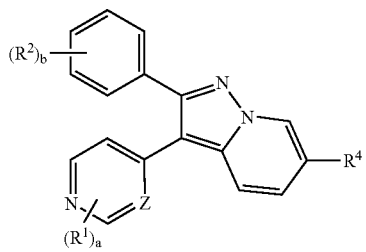

R⁴ = alkyl, alkenyl, alkynyl, aryl, hetaryl, cyano, carboalkoxy, alkylamino

Compounds of general formula (XXXI) wherein $R^4$ is a trifluoromethyl group ($CF_3$) can be converted into compounds wherein $R^4$ is a carboxylic acid derivative. Preferably said transformation is carried out by treatment of a compound of general formula (XXXII) with a suitable base in an alcoholic solvent and optionally heating the reaction to about 80° C. Preferably the base is a sodium or potassium alkoxide such as sodium ethoxide and the like and the preferred solvents include, but are not limited to, methanol, ethanol, propanol, isopropanol and the like. The resulting trialkylorthoesters can be converted to lower alkyl esters by treatment of said orthoesters in a suitable solvent with an acid in the presence of water. Preferred acids include p-toluenesulfonic acid, hydrochloric acid and sulfuric acid and the preferred solvents include lower alcohols and acetone. Lower alkyl esters such as those represented by general formula (XXXIII) can be further converted into different compounds by transformation of the ester group in a manner well known in the art.

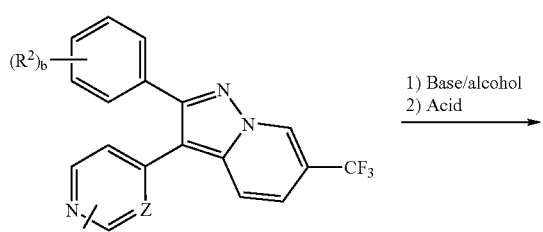

(XXXII)

Stille coupling
Suzuki coupling

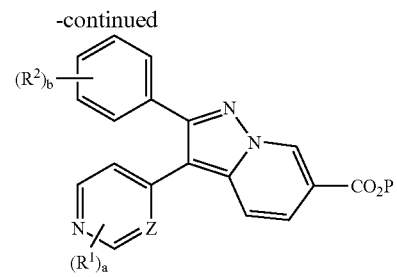

(XXXIII) P = lower alkyl

Compounds of general formula (I), wherein $R^1$, $R^2$ or $R^4$ contains a hydroxyl group can be reacted to give compounds wherein the hydroxyl group is converted to an ester, carbonate or carbamate group using procedures well known in the literature (March J. Advanced Organic Chemistry).

Similarly, compounds of general formula (I), wherein $R^1$, $R^2$ or $R^4$ contains an amino group can be reacted to give compounds wherein the amino group is converted to an amide, carbamate or urea group using procedures known in the literature (March J. Advanced Organic Chemistry).

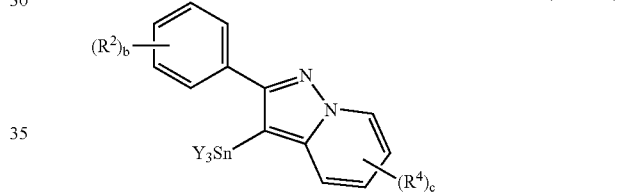

(XXXIV)

Certain compounds of formula (I) wherein at least one $R^2$ group is substituted on an ortho position of the phenyl ring may be prepared by the reaction of a compound of formula (XXXIV) wherein Y is methyl or butyl and wherein at least one $R^2$ group is substituted on an ortho position of the phenyl ring:

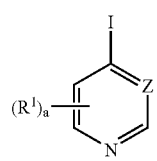

(XXXV)

with a compound of formula (XXXV):

This reaction is essentially the reverse of the coupling reaction described above between compounds of formula (VIII) and (IX). The reaction conditions are analogous to those previously described for the coupling reaction between compounds of formula (VIII) and (IX).

Compound (XXXIV) wherein Y is butyl may be prepared from a compound of formula (VII) using a strong base, butyl lithium and tri-n-butyl stannyl chloride at low temperature (e.g. −78° C.) in an inert solvent such as THF.

1) Base/alcohol
2) Acid

The present invention includes within its scope a process for the preparation of a compound of the invention which process comprises the step of mixing a compound of general formula (XIX)

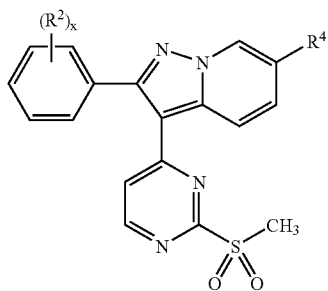

(XIX)

wherein x, $R^2$ and $R^4$ are as defined for formula (I) above, with an amine of general formula $H_2N$—$(CH_2)_n$—$R^5$ wherein $R^5$ is as defined for formula (I) above, and heating to form a homogeneous melt.

The present invention also includes within its scope a compound of general formula (XIX)

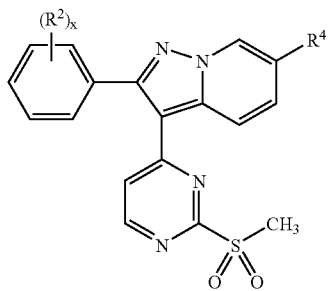

(XIX)

wherein x is 1, 2 or 3; and each $R^2$ is independently selected from hydrogen, CN, $OC_{1-4}$alkyl, halogen or trihalomethyl; and $R^4$ is selected from CN, halogen or trihalomethyl, for use as an intermediate in the synthesis of a compound of formula (I) or a salt or solvate thereof or a physiologically functional derivative thereof.

The present invention also includes within its scope a compound of general formula (XX)

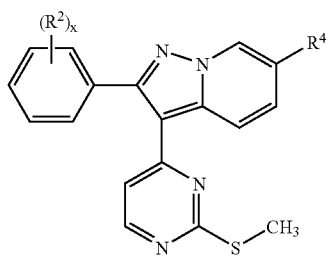

(XX)

wherein x is 1, 2 or 3; and each $R^2$ is independently selected from hydrogen, CN, $OC_{1-4}$alkyl, halogen or trihalomethyl; and $R^4$ is selected from CN, halogen or trihalomethyl, for use as an intermediate in the synthesis of a compound of formula (I) or a salt or solvate thereof or a physiologically functional derivative thereof.

Examples of compounds of general formula (XIX) and (XX) which are included within the scope of the present invention as useful intermediates for the preparation of a compound of formula (I) or a salt or solvate thereof or a physiologically functional derivative thereof include the following:

4-[2-(4-Fluorophenyl)-6-(trifluoromethyl)pyrazolo[1,5-a]pyridin-3-yl]pyrimidin-2-yl methyl sulfide;

Methyl 4-{6-(trifluoromethyl)-2-[4-(trifluoromethyl)phenyl]pyrazolo[1,5-a]pyridin-3-yl}pyrimidin-2-yl sulfide;

4-[2-(3-Chloro-4-fluorophenyl)-6-(trifluoromethyl)pyrazolo[1,5-a]pyridin-3-yl]pyrimidin-2-yl methyl sulfide;

Methyl 4-{6-(trifluoromethyl)-2-[3-chlorophenyl]pyrazolo[1,5-a]pyridin-3-yl}pyrimidin-2-yl sulfide;

4-[2-(4-Fluorophenyl)-6-(trifluoromethyl)pyrazolo[1,5-a]pyridin-3-yl]pyrimidin-2-yl methyl sulfone;

Methyl 4-{6-(trifluoromethyl)-2-[4-(trifluoromethyl)phenyl]pyrazolo[1,5-a]pyridin-3-yl}pyrimidin-2-yl sulfone;

Methyl 4-{6-(trifluoromethyl)-2-[3-chlorophenyl]pyrazolo[1,5-a]pyridin-3-yl}pyrimidin-2-yl sulfone; and Methyl 4-{6-(trifluoromethyl)-2-[3-chlorophenyl]pyrazolo[1,5-a]pyridin-3-yl}pyrimidin-2-yl sulfone.

Whilst it is possible for the compounds, salts, solvates or physiologically functional derivatives of the present invention to be administered as the new chemical, the compounds of Formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of Formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of Formula (I) and their pharmaceutically acceptable derivatives. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or -beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolyllysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly-soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 μg/kg body weight. In most cases they will be administered in one or more doses in an amount not in excess of about 20 mg/kg body weight per day. Preferably, in most cases, dose is from about 100 μg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

Certain compounds of the present invention are also generally inhibitors of JNK kinase and are therefore also inhibitors of cytokine production which is mediated by JNK kinase.

It is known that p38 and/or JNK kinase activity can be elevated (locally or throughout the body), p38 and/or JNK kinase can be incorrectly temporally active or expressed, p38 and/or JNK kinase can be expressed or active in an inappropriate location, p38 and/or JNK kinase can be constitutively expressed, or p38 and/or JNK kinase expression can be erratic; similarly, cytokine production mediated by p38 and/or JNK kinase activity can be occurring at inappropriate times, inappropriate locations, or it can occur at detrimentally high levels.

Accordingly, the present invention provides a method for the treatment of a condition or disease state mediated by p38 and/or JNK kinase activity in a subject which comprises administering to said subject a therapeutically effective amount of a compound of formula (I) or a pharmaceutically acceptable salt or solvate thereof or a physiologically functional derivative thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 and/or JNK kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 and/or JNK kinase or in need of inhibition or regulation of p38 and/or JNK mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I) or a pharmaceutically acceptable salt or solvate thereof or a physiologically functional derivative thereof. A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable salt or solvate thereof or a physiologically functional derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable salt or solvate thereof or a physiologically functional derivative thereof.

A further aspect of the invention provides a method of treatment of a human or animal subject suffering from rheumatoid arthritis, neurodegenerative disease, Alzheimer's disease, Parkinson's disease and epilepsy which comprises administering to said subject a therapeutically effective amount of a compound of formula (I) or a pharmaceutically acceptable salt or solvate thereof or a physiologically functional derivative thereof.

A further aspect of the invention provides a compound of formula (I), or a pharmaceutically acceptable salt or solvate thereof or a physiologically functional derivative thereof, for use in therapy.

A further aspect of the invention provides the use of a compound of formula (I), or a pharmaceutically acceptable salt or solvate thereof or a physiologically functional derivative thereof, for the preparation of a medicament for the treatment of a condition or disease state mediated by p38 and/or JNK kinase activity or mediated by cytokines produced by p38 and/or JNK kinase activity.

A further aspect of the invention provides the use of a compound of formula (I), or a pharmaceutically acceptable salt or solvate thereof or a physiologically functional derivative thereof, for the preparation of a medicament for the treatment of a condition or disease state selected from rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, and cancer including breast cancer, colon cancer, lung cancer or prostatic cancer.

A further aspect of the invention provides the use of a compound of formula (I), or a pharmaceutically acceptable salt or solvate thereof or a physiologically functional derivative thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy, and cancer including breast cancer, colon cancer, lung cancer and prostatic cancer.

A further aspect of the invention provides the use of a compound of formula (I), or a pharmaceutically acceptable salt or solvate thereof or a physiologically functional derivative thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer. A further aspect of the invention provides the use of a compound of formula (I), or a pharmaceutically acceptable salt or solvate thereof or a physiologically functional derivative thereof, for the preparation of a medicament for the treatment of a condition or disease state selected from rheumatoid arthritis, neurodegenerative disease, Alzheimer's disease, Parkinson's disease and epilepsy.

The compounds of formula (I) and their salts, solvates and physiologically functional derivatives may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof or a physiologically functional derivative thereof and at least one other pharmaceutically active agent. The compound(s) of formula (I) or pharmaceutically acceptable salt(s) or solvate(s) thereof or physiologically functional derivative(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof or physiologically functional derivative(s) thereof and the other pharmaceutically active agent(s) and the relative timings of administration will be selected in order to achieve the desired combined therapeutic effect. Examples of other pharmaceutically active agents which may be employed in combination with compounds of formula (I) and their salts, solvates and physiologically functional derivatives for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

EXAMPLES

The following examples are illustrative embodiments of the invention, not limiting the scope of the invention in any way. Reagents are commercially available or are prepared according to procedures in the literature. Example numbers refer to those compounds listed in the tables above. $^1$H NMR spectra were obtained on VARIAN Unity Plus or Bruker DPX NMR spectrophotometers at 300 or 400 MHz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

Example 1

2-(4-Fluorophenyl)-3-(4-pyridyl)-pyrazolo[1,5-a]pyridine

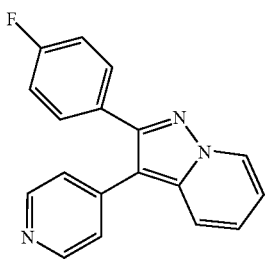

a) 1-(4-Fluorophenyl)-2-trimethylsilylacetylene

4-Fluoroiodobenzene (112 mL, 0.97 mol) and triethylamine (176 mL, 1.26 mol) are dissolved in dry THF (1.2 L) and nitrogen gas was bubbled through the solution for about 20 min. Copper (I) iodide (1.08 g, 5.7 mmol) and bis(triphenyphosphine)palladium dichloride (2.15 g, 3 mmol) are added and then trimethylsilylacetylene (178 mL, 1.3 mol) was added dropwise over about 40 min with the temperature being maintained at about 23° C. A large amount of precipitate forms (presumably Et$_3$NHCl) which necessitates mechanical stirring. Following complete addition of the trimethylsilylacetylene the mixture was allowed to stir at room temperature for about 18 h. The mixture was filtered and the solid washed with cyclohexane. The combined filtrates are concentrated under reduce pressure to give a brown oil. Application of this oil to a pad of silica gel followed by elution with cyclohexane gave a yellow solution. Removal of the solvent gave the title compound as a yellow oil; 182.8 g (95%).

b) Methyl 3-(4-fluorophenyl)propiolate

A solution of 1-(4-fluorophenyl)-2-trimethylsilylacetylene (64 g, 0.33 mol) in dry diethyl ether (400 mL) was cooled to 0° C. under a nitrogen atmosphere. To this solution was added, dropwise over 45 min, a solution of tetrabutylammonium fluoride (1M in THF, 330 mL, 0.33 mol) via a dropping funnel maintaining the internal temperature below 2° C. The mixture was allowed to warm to room temperature over about 1 h. Diethyl ether (300 mL) was added to the mixture and the organic solution was washed with water, saturated brine and then dried (MgSO$_4$). The magnesium sulfate was removed by filtration and the filtrate was cooled to about −78° C. n-Butyl lithium (1.6M in hexanes, 450 mL, 0.72 mol) was added dropwise via a dropping funnel over about 1 h while the temperature was maintained below −66° C. After complete addition the mixture was stirred at 78° C. for about 1 h and then a precooled solution of methyl chloroformate (110 mL, 1.4 mol) in dry diethyl ether (200 mL) was added in a continuous stream as fast as possible. The mixture was allowed to cool to −78° C. and then allowed to warm to room temperature over 1.5 h. The organic reaction mixture was washed with water and saturated brine and then dried (MgSO$_4$). The solvents are remove under reduced pressure and the residue dried under reduced pressure to give the title compound as a brown solid, 36.5 g (61%). $^1$H NMR (CDCl$_3$) δ 7.58 (dd, 2H, J=9, 5.4 Hz), 7.07 (t, 2H, J=8.5 Hz), 3.84 (s, 3H). MS (+ve ion electrospray) 178 (30), (M$^+$).

c) Methyl 2-(4-fluorophenyl)-pyrazolo[1,5-a]pyridine-3-carboxylate

A stirred solution of methyl 3-(4-fluorophenyl)propiolate (8.02 g, 45 mmol) and 1-aminopyridinium iodide (10 g, 45 mmol) in dry acetonitrile (150 mL) was cooled to about 0° C. A solution of 1,8-diazabicycloundec-7-ene (13.7 g, 90 mmol) in dry acetonitrile (50 mL) was added dropwise over 1 h. The mixture was allowed to stir at room temperature for about 18 h. The reaction mixture was cooled in an ice bath for about 30 min and the precipitate was collected by filtration and washed with cold acetonitrile (10 mL). The solid was dried under reduced pressure to give the title compound as a white solid, 8.48 g (70%). $^1$H NMR (CDCl$_3$) δ 8.50 (d, 1H, J=8.4 Hz), 8.18 (d, 1H, J=8.8 Hz), 7.78 (m, 2H), 7.42 (t, 1H, J=8.4 Hz), 7.13 (t, 2H, J=8.8 Hz), 6.97 (td, 1H, J=6.8, 1 Hz). MS (+ve ion electrospray) 271 (100), (MH$^+$).

d) 2-(4-Fluorophenyl)-pyrazolo[1,5-a]pyridine-3-carboxylic Acid

A solution of methyl 2-(4-fluorophenyl)-pyrazolo[1,5-a]pyridine-3-carboxylate (5.0 g, 18.5 mmol) in 2N aqueous sodium hydroxide (50 ml) and methanol (30 mL) was heated at reflux for about 3 h. The mixture was filtered and the filtrate was washed with diethyl ether (20 mL) and then concentrated under reduced pressure to about half the original volume. Concentrated hydrochloric acid was added to adjust the pH to about 2 and the resulting solid was collected by filtration and washed with water and dried under vacuum to give the title compound as a white solid, 4.8 g (ca. 100%). $^1$H NMR (d$_6$-DMSO) δ 12.43 (brs, 1H), 8.84 (d, 1H, J=6.9 Hz), 8.14 (d, 1H, J=9 Hz), 7.82 (m, 2H), 7.57 (t, 1H, J=8.1 Hz), 7.28 (t, 2H, J=9 Hz), 7.15 (td, 1H, J=6.9, 1.2 Hz). MS (+ve ion electrospray) 257 (100), (MH$^+$).

e) 2-(4-Fluorophenyl)-3-bromopyrazolo[1,5-a]pyridine

To a solution of 2-(4-fluorophenyl)-pyrazolo[1,5-a]pyridine-3-carboxylic acid (0.96 g, 3.75 mmol) in dry DMF (10 mL) was added sodium bicarbonate (0.95 g, 11.3 mmol) followed by N-bromosuccinimide (0.667 g, 3.75 mmol) and the mixture was stirred at room temperature under a nitrogen atmosphere for about 90 min. The mixture was poured into water (300 mL) and the resulting solid was collected by filtration and washed with water. The solid was dissolved in 10:1 chloroform:methanol (10 mL) and filtered through a pad (0.5 cm) of silica gel using 10:1 chloroform:methanol as eluent. The filtrate was evaporated to leave the title compound as a tan solid, 0.87 g (80%). $^1$H NMR (d$_6$-DMSO) δ 8.7 (d, 1H, J=6.9 Hz), 8.02 (dd, 2H, J=8.7, 5.7 Hz), 7.61 (d, 1H, J=8.4 Hz), 7.40 (t, 1H, J=6 Hz), 7.38 (t, 2H, J=9 Hz), 7.04 (t, 1H, J=6.9 Hz). MS (+ve ion electrospray) 293 (100), (MH$^+$).

f) 2-(4-Fluorophenyl)-3-(4-pyridyl)-pyrazolo[1,5-a]pyridine

To a solution of 2-(4-fluorophenyl)-3-bromopyrazolo[1,5-a]pyridine (0.2 g, 0.68 mmol) and 4-(tributylstannyl)pyridine (0.38 g, 1 mmol) in dry toluene (10 mL) was added tetrakis(triphenylphosphine)palladium (0) (0.03 g, 0.03 mmol) and the mixture was heated at reflux temperature under a nitrogen atmosphere for about 48 h. The mixture was cooled to room temperature and diluted with diethyl ether (40 mL). The mixture was poured into a 10% aqueous solution of potassium fluoride (20 mL) and the mixture was stirred for 1 h. The biphasic mixture was filtered through a pad (1 cm) of diatomaceous earth and the organic phase was separated. The aqueous phase was extracted with diethyl ether (10 mL) and the combined organic phases are washed with brine, dried (MgSO$_4$), filtered and the solvent evaporated under reduced pressure. The residue was purified using silica gel chromatography with 20% EtOAc in hexanes, followed by 50% EtOAc in hexanes, as eluent to give the title compound as an off white solid, 0.16 g (80%). $^1$H NMR (CDCl$_3$) δ 8.58 (brs, 2H), 8.50 (d, 1H, J=7.2 Hz), 7.63 (d, 1H, 9 Hz), 7.52 (m, 2H), 7.27–7.20 (m, 3H), 7.06 (t, 2H, J=8.7 Hz), 6.86 dt, 1H, J=7, 1 Hz). MS (+ve ion electrospray) 290 (100), (MH$^+$).

Example 2

2-(4-Fluorophenyl)-6-methyl-3-(4-pyridinyl)pyrazolo[1,5-a]pyridine

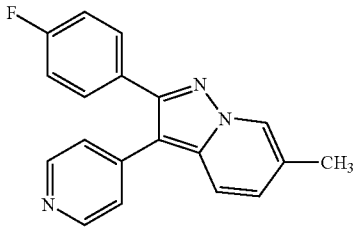

a) 1-amino-3-methylpyridinium 2,4,6-trimethylbenzylsulfonate

To cold (0° C.) trifluoroacetic acid was added N-tert-butoxycarbonyl-O-(mesitylsulfonyl)hydroxylamine in portions over about 15 min. The solution was stirred for about 15 min at room temperature. The solution was poured into ice water and the resulting precipitate was collected by filtration and air-dried for 5 min. The solid was dissolved in chloroform and this solution was dried (MgSO$_4$). The MgSO$_4$ was removed by filtration and the filtrate was added to a solution of 3-methylpyridine in chloroform. The mixture was stirred for 45 min and then filtered To the filtrate was added diethyl ether and the product allowed to predipitate. The solid was collected by filtration, washed with diethyl ether and dried to give the title compound.

b) Methyl 2-(4-fluorophenyl)-6-methyl-pyrazolo[1,5-a]pyridine-3-carboxylate

To a stirred solution of methyl 3-(4-fluorophenyl)propiolate (Example 1 b) and 1-amino-3-methylpyridinium 2,4,6-trimethylbenzenesulfonate in dry acetonitrile was added, dropwise over 10 min, a solution of 1,8-diazabicycloundec-7-ene in dry acetonitrile. The mixture was allowed to stir at room temperature for about 18 h. The solvent was evaporated under reduced pressure and the residue was partitioned between water and ethyl acetate and the organic phase separated. The aqueous was extracted with ethyl acetate and the combined organic extracts are dried (MgSO$_4$), and the solvent removed under vacuum. The residue was purified by chromatography on silica gel using 10:1 hexanes:ethyl acetate as eluent to give the title compound and also methyl 2-(4-fluorophenyl)-4-methyl-pyrazolo[1,5-a]pyridine-3-carboxylate.

c) 2-(4-fluorophenyl)-6-methyl-pyrazolo[1,5-a]pyridine-3-carboxylic Acid

In a similar manner as described in Example 1d, from methyl 2-(4-fluorophenyl)-6-methyl-pyrazolo[1,5-a]pyridine-3-carboxylate was obtained 2-(4-fluorophenyl)-6-methyl-pyrazolo[1,5-a]pyridine-3-carboxylic acid as a white solid. $^1$H NMR (d$_6$-DMSO) δ 8.69 (s, 1H), 8.07 (d, 1H, J=9.1 Hz), 7.84 (dd, 2H, J=14.0 Hz), 7.44 (d, 1H, J=9.1 Hz), 7.28 (t, 2H, J=17.7 Hz), 2.51 (s, 3H). MS (+ve electrospray) 270 (100), (M+).

d) 2-(4-fluorophenyl)-3-bromo-6-methyl-pyrazolo[1,5-a]pyridine

Following the procedure given in Example 1e, from 2-(4-fluorophenyl)-6-methyl-pyrazolo[1,5-a]pyridine-3-carboxylic acid was obtained 2-(4-fluorophenyl)-3-bromo-6-methyl-pyrazolo[1,5-a]pyridine as a white solid. $^1$H NMR (CDCl$_3$) δ 8.27 (s, 1H), 8.05 (m, 2H), 7.47 (d, 1H, J=9.0 Hz), 7.21 (m, 2H), 7.12 (d, 1H, J=9.0 Hz), 2.40 (s, 3H). MS (+ve electrospray) 306 (60), (MH+).

e) 2-(4-Fluorophenyl)-6-methyl-3-(4-pyridinyl)pyrazolo[1,5-a]pyridine

In a similar manner as described in Example if, from 2-(4-fluorophenyl)-3-bromo-6-methyl-pyrazolo[1,5-a]pyridine (0.1 g, 0.33 mmol), and 4-tri-n-butylstannylpyridine (0.17 g, 0.46 mmol) was obtained the title compound as a white solid 0.015 g (14%). This material was dissolved in diethyl ether and treated with HCl in diethyl ether to afford the corresponding hydrochloride salt. $^1$H NMR (d$_6$-DMSO) δ 8.78 (s, 1H), 8.72 (d, 2H, J=6.5 Hz), 7.94 (d, 1H, J=9.2 Hz), 7.78 (d, 2H, J=6.6 Hz), 7.60 (m, 2H), 7.48 (d, 1H, J=9.2 Hz), 7.33 (t, 2H, J=17.6 Hz), 2.40 (s, 3H). MS (+ve electrospray) 304 (100), (MH+).

Example 3

2-(4-Fluorophenyl)-5-methyl-3-(4-pyridinyl)pyrazolo[1,5-a]-pyridine

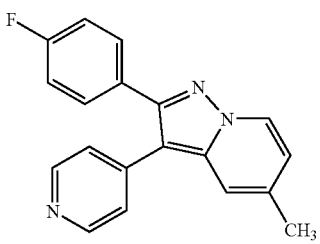

In a similar manner as described in Example 2a, 2b, 1d, 1e and 1f, from 4-methylpyridine was obtained the title compound as a white solid. This material was dissolved in diethyl ether and treated with HCl in diethyl ether to afford the corresponding hydrochloride salt. $^1$H NMR (CDCl$_3$) δ 8.50 (d, 2H, J=6.2 Hz), 8.44 (d, 1H, J=6.9 Hz), 7.67 (d, 2H, J=6.2 Hz), 7.57 (s, 1H), 7.44 (m, 2H), 7.12 (t, 2H, J=17.0 Hz), 6.87 (d, 1H, J=7.1 Hz), 2.49 (s, 3H). MS (+ve electrospray) 340 (10), (MH$^+$).

Example 4

2-(4-Fluorophenyl)-4-methyl-3-(4-pyridinyl)pyrazolo[1,5-a]-pyridine

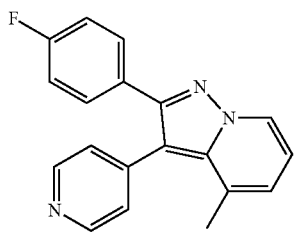

In a similar manner as described in Example 1d, 1e and 1f from methyl 2-(4-fluorophenyl)-4-methyl-pyrazolo[1,5-a]pyridine-3-carboxylate (prepared as a side-product in Example 2b) was obtained the title compound as a white solid. This material was dissolved in diethyl ether and treated with HCl in diethyl ether to afford the corresponding hydrochloride salt. $^1$H NMR (d$_6$-DMSO) δ 8.78 (d, 2H, J=6.0 Hz), 7.70 (d, 1H, J=6.8 Hz), 7.85 (d, 2H, J=6.0 Hz), 7.37 (m, 2H), 7.18 (m, 3H), 7.00 (t, 1H, J=13.9 Hz), 2.12 (s, 3H). MS (+ve electrospray) 340 (100), (MH$^+$).

Example 5

2-(4-Fluorophenyl)-5-methoxy-3-(4-pyridinyl)pyrazolo[1,5-a]pyridine

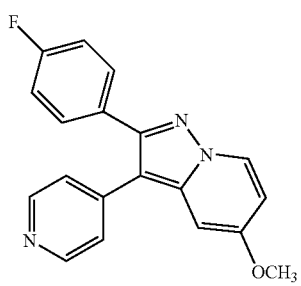

In a similar manner as described in Examples 2a, 2b, 1d, 1e and 1f, from 4-methoxypyridine was obtained the title compound. $^1$H NMR (d$_6$-DMSO) δ 3.84 (s, 3H), 6.69 (dd, 1H, J=2.8, 7.6 Hz), 6.95 (d, 1H, J=2.4 Hz), 7.24 (m, 4H), 7.47 (dd, 2H, J=6.0, 8.8 Hz), 8.51 (d, 2H, J=6.0 Hz), 8.63 (d, 1H, J=6.0 Hz).

Example 6

2-(4-Fluorophenyl)-5-hydroxymethyl-3-(4-pyridinyl)pyrazolo[1,5-a]pyridine

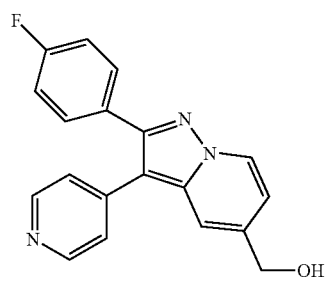

a) 4-(tert-butyldimethylsilyloxymethyl)pyridine

To a stirred solution of tert-butyldimethylsilyl chloride (16.6 g, 0.11 mol) and imidazole (16.3 g, 0.24 mol) in DMF (20 mL) was added 4-pyridinemethanol (10 g, 0.09 mol) and the mixture was stirred for about 1 h. The reaction mixture was poured into diethyl ether (200 mL) and the resulting solution was washed with water (100 mL). The aqueous phase was extracted with diethyl ether and the combined organic phases are washed with water, brine and dried (MgSO$_4$). The solvent was evaporated under reduced pressure to leave 4-(tertbutyidimethylsilyloxymethyl)pyridine, 22.5 g. $^1$H NMR (d$_6$-DMSO) d 8.49 (d, 2H), 7.27 (d, 2H), 4.62 (s, 2H), 0.9 (s, 9H), 0.09 (s, 6H).

b) 2-(4-Fluorophenyl)-5-hydroxymethyl-3-(4-pyridinyl)-pyrazolo[1,5-a]pyridine

Then, in a similar manner as described in Examples 2a, 2b, 1d, 1e and 1f, from 4-(tert-butyldimethylsilyloxymethyl)pyridine was obtained the title compound, $^1$H NMR (d$_6$-DMSO) δ 4.55 (d, 2H, J=5.6 Hz), 5.45 (t, 1H, J=5.6 Hz), 6.94 (d, 1H, J=6.8 Hz), 7.23 (t, 2H, J=8.8 Hz), 7.27 (d, 2H, J=6.0 Hz), 7.51 (dd, 2H, J=5.6, 8.4 Hz), 8.60 (s, 1H), 8.55 (d, 2H, J=5.6 Hz), 8.71 (d, 1H, J=7.2 Hz). MS (AP+) m/z 320 (M$^+$+H).

Example 7

2-(4-Fluorophenyl)-4-hydroxymethyl-3-(4-pyridinyl)-pyrazolo[1,5-a]pyridine

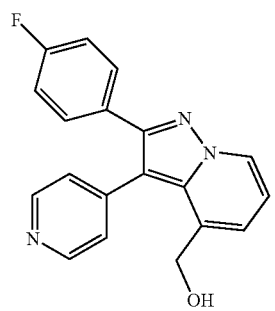

a) 3-(tert-butyldimethylsilyloxymethyl)pyridine

In a similar manner as described in Example 6a, 3-(tert-butyldimethylsilyloxymethyl)pyridine was obtained from 3-pyridinemethanol, (10 g, 0.09 mol), 22 g. $^1$H NMR (d$_6$-DMSO) δ 8.50 (s, 1H), 8.44 (d, 1H), 7.68 (d, 1H), 7.34 (dd, 1 h), 4.71 (s, 1H), 0.87 (s, 9H), 0.06 (s, 6H).

b) 2-(4-Fluorophenyl)-4-hydroxymethyl-3-(4-pyridinyl)-pyrazolo[1,5-a]pyridine

In a similar manner as described in Examples 2a, 2b, 1d, 1e and 1f, from 3-(tert-butyldimethylsilyloxymethyl)pyridine was obtained the title compound, $^1$H NMR (d$_6$-DMSO) δ 4.18 (dd, 2H, J=5.2 Hz), 5.22 (t, 1H, J=5.2 Hz), 6.97 (t, 1H, J=6.8 Hz), 7.13 (t, 2H, J=8.8 Hz), 7.30 (d, 2H, J=7.2 Hz), 7.37 (m, 4H), 8.56 (d, 2H, J=5.6 Hz), 8.64 (d, 1H, J=7.2 Hz).

Example 8

6-Fluoro-2-(4-fluorophenyl)-3-(4-pyridinyl)pyrazolo[1,5-a]pyridine

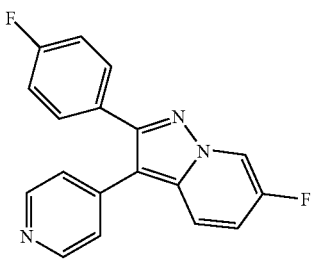

In a similar manner as described in Examples 2a, 2b, 1d, 1e and 1f, from 3-fluoropyridine was obtained the title compound as a white solid which was converted to a hydrochloride salt. $^1$H NMR (d$_6$-DMSO) δ 9.24 (s, 1H), 8.71 (di 2H, J=5.3 Hz), 8.00 (m, 2H), 7.72 (d, 2H, J=5.3 Hz), 7.70 (m, 1H), 7.55 (m, 2H), 7.28 (t, 2H, J=17.6 Hz). MS (+ve electrospray) 308 (40), (MH$^+$).

Example 9

4-Fluoro-2-(4-fluorophenyl)-3-(4-pyridinyl)pyrazolo[1,5-a]pyridine

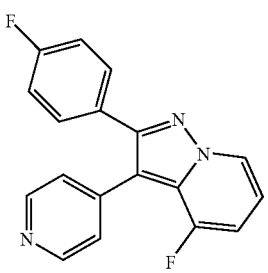

In a similar manner as described in Examples 2a, 2b, 1d, 1e and 1f, from 3-fluoropyridine was obtained the title compound. $^1$H NMR (d$_6$-DMSO) δ 7.05 (m, 1H), 7.27 (m, 3H), 7.36 (m, 2H), 7.36 (m, 2H), 8.59 (d, 2H, J=7.6 Hz), 8.74 (d, 1H, J=9.2 Hz). MS (ES+) m/z 308 (MH$^+$).

Example 10

[2-(4-Fluorophenyl)-3-(4-pyridyl)pyrazolo[1,5-a]pyridin-5-yl]methyl 2-methylbenzoate

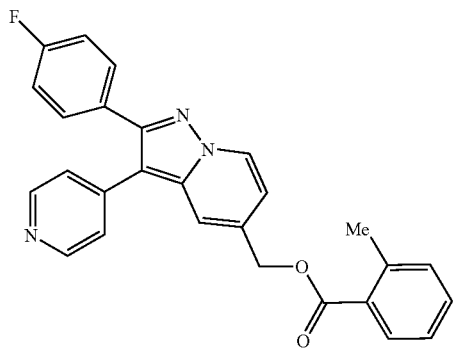

2-(4-Fluorophenyl)-5-hydroxymethyl-3-(4-pyridinyl)pyrazolo[1,5-a]pyridine (Example 6. 50 mg, 0.157 mmol), triphenyl phosphine (82 mg, 0.314 mmol) and 2-methylbenzoic acid (0.314 mmol) are dissolved in dry THF (3 mL). To the stirred solution is added diethyl azodicarboxylate (55 mg, 0.314 mmol) dropwise. The resulting solution is stirred at room temperature until reaction is complete as determined by TLC and then diluted with hexane/ethyl acetate (30 mL of a 1:1 mixture) and washed with water (×3). The organic phase is then shaken with dilute hydrochloric acid. In cases were the hydrochloride salt of the product deposits at this stage it is filtered off, washed with water and then hexane and dried. If no deposit is observed, the acidic phase is separated, washed once with hexane/ethyl acetate (15 mL of a 1:1 mixture) and basified with saturated sodium bicarbonate solution. This is then extracted with dichloromethane (15 mL) five times and the dichloromethane solution dried (MgSO$_4$), filtered and concentrated to give the title compound. $^1$H NMR (d$_6$-DMSO) δ 2.50 (s, 3H), 5.41 (s, 2H), 7.25–7.33 (m, 5H), 7.48 (t, J=7.4 Hz, 1H), 7.56 (dd, J=5.6, 8.5 Hz, 2H), 7.73 (d, J=5.8 Hz, 2H), 7.88 (d, J=7.9 Hz, 1H), 8.06 (s, 1H), 8.71 (d, J=6.2 Hz, 2H), 8.92 (d, J=7.1 Hz, 1H). APESI-MS m/z 438 (M+1)$^+$.

Example 11

[2-(4-Fluorophenyl)-3-(4-pyridinyl)pyrazolo[1,5-a]pyridin-5-yl]methyl Isonicotinate

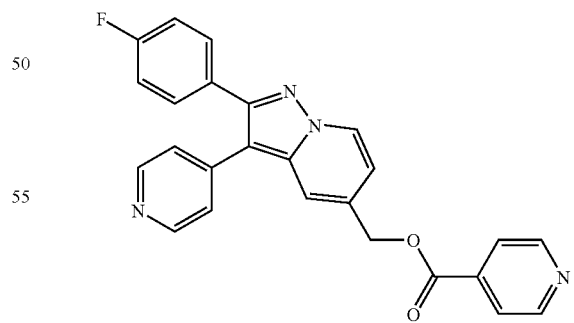

2-(4-Fluorophenyl)-5-hydroxymethyl-3-(4-pyridinyl)pyrazolo[1,5-a]pyridine (Example 6. 30 mg, 0.094 mmol) and 4-pyridinecarboxylic acid (0.12 mmol) are dissolved in dimethylformamide (0.5 mL) and diethyl cyanophosphonate (35 mg, 0.2 mmol, 93% grade), followed by triethylamine (35 mg, 0.35 mmol) are added dropwise. The resulting solution is stirred at room temperature until the reaction is complete as determined by TLC and then diluted with hexane/ethyl acetate (30 mL of a 1:1 mixture) and washed with water (3×). The organic phase is then shaken with dilute hydrochloric acid. In cases were the hydrochloride salt of the product deposits at this stage it is filtered off, washed with water and then hexane and dried. If no deposit is observed, the acidic phase is separated, washed once with hexane/ethyl acetate (15 mL of a 1:1 mixture) and basified with saturated sodium bicarbonate solution. This is then extracted with dichloromethane (15 mL) five times and the dichloromethane solution dried (MgSO$_4$), filtered and concentrated to give the title compound. $^1$H NMR (d$_6$-DMSO) δ 5.43 (s, 2H), 7.15 (d, J=6.9 Hz, 1H), 7.25 (t, J=8.8 Hz, 2H), 7.30 (d, J=5.9 Hz, 2H), 7.50–7.53 (m, 2H), 7.84–7.87 (m, 3H), 8.55 (d, J=5.7 Hz, 2H), 8.79 (d, J=5.9 Hz, 2H), 8.82 (d, J=7.1 Hz, 1H); APESI-MS m/z 425 (M+1)$^+$.

Example 12

[2-(4-Fluorophenyl)-3-(4-pyridinyl)pyrazolo[1,5-a]pyridin-5-yl]methyl Nicotinate

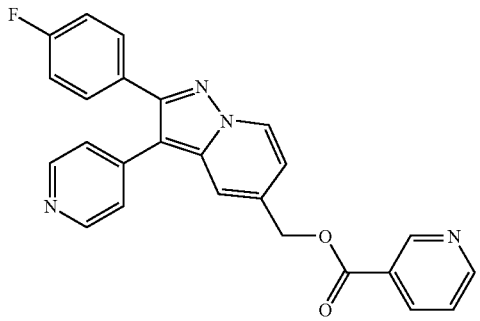

In a similar manner as described for Example 11, using 3-pyridinecarboxylic acid in place of 4-pyridinecarboxylic acid, is obtained the title compound. $^1$H NMR (d$_6$-DMSO) δ 5.43 (s, 2H), 7.16 (d, J=7.1 Hz, 1H), 7.24 (t, J=8.8 Hz, 2H), 7.30 (d, J=5.7 Hz, 2H), 7.50–7.57 (m, 3H), 7.86 (s, 1H), 8.31 (d, J=7.8 Hz, 1H), 8.54 (d, J=5.7 Hz, 2H), 8.80–8.82 (m, 2H), 9.11 (s, 1H); APESI-MS m/z 425 (M+1)$^+$.

Example 13

[2-(4-Fluorophenyl)-3-(4-pyridinyl)pyrazolo[1,5-a]pyridin-5-yl]methyl 3-bromo-2-thiophenecarboxylate

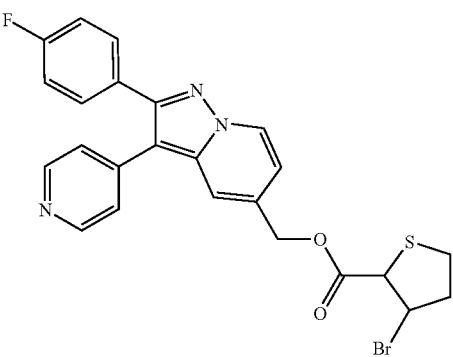

In a similar manner as described for Example 11, using 3-bromothiophene-2-carboxylic acid in place of 4-pyridinecarboxylic acid, is obtained the title compound. $^1$H NMR (d$_6$-DMSO) δ 5.43 (s, 2H), 7.21 (d, J=7.3 Hz, 1H), 7.26–7.31 (m, 3H), 7.56 (t, J=7.1 Hz, 2H), 7.68–7.70 (m, 2H), 8.01 (d, J=5.2 Hz, 1H), 8.04 (s, 1H), 8.70 (d, J=5.9 Hz, 2H), 8.90 (d, J=7.1 Hz, 2H), APESI-MS m/z 508/510 (M+1)$^+$.

Example 14

[2-(4-Fluorophenyl)-3-(4-pyridinyl)pyrazolo[1,5-a]pyridin-5-yl]methyl 6-aminonicotinate

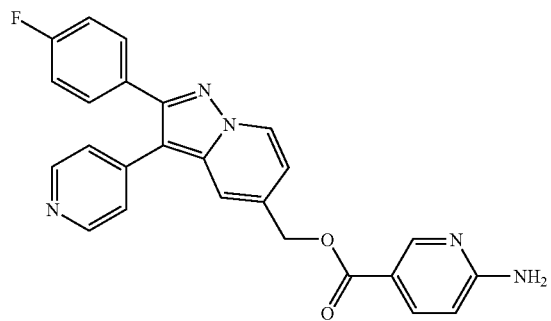

In a similar manner as described for Example 11, using 2-amino-5-pyridinecarboxylic acid in place of 4-pyridinecarboxylic acid, is obtained the title compound. $^1$H NMR (d$_6$-DMSO) δ 5.31 (s, 2H), 6.43 (d, J=8.8 Hz, 1H), 6.87 (bs, 2H), 7.08 (d, J=7.3 Hz, 1H), 7.26 (t, J=8.8 Hz, 2H), 7.29 (d, J=5.8 Hz, 2H), 7.51 (dd, J=5.6, 8.2 Hz, 2H), 7.79 (s, 1H), 7.82 (dd, J=2.2, 8.8 Hz, 1H), 8.54 (m, 3H), 8.79 (d, J=7.1 Hz, 1H).

Example 15

[2-(4-Fluorophenyl)-3-(4-pyridinyl)pyrazolo[1,5-a]pyridin-5-yl]methyl 5-(methylsulfonyl)-2-thiophenecarboxylate

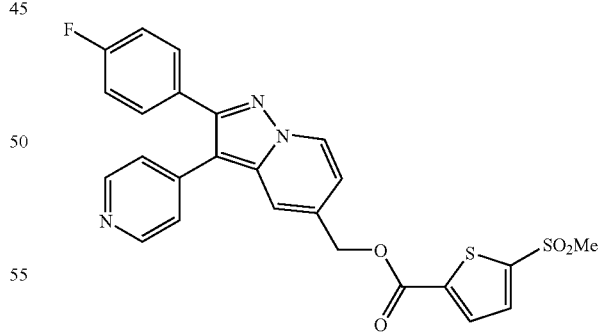

In a similar manner as described for Example 11, using 2-methylsulfonyl-5-thiophenecarboxylic acid in place of 4-pyridinecarboxylic acid, is obtained the title compound. $^1$H NMR (d$_6$-DMSO) δ 3.47 (s, 3H), 5.48 (s, 2H), 7.16 (d, J=7.1 Hz, 1H), 7.30 (t, J=8.8 Hz, 2H), 7.36 (d, J=5.7 Hz, 2H), 7.58 (dd, J=5.7, 8.9 Hz, 2H), 7.91 (d, J=3.6 Hz, 2H), 7.,92 (d, J=4.0 Hz, 1H), 8.61 (d, J=5.9 Hz, 2H), 8.88 (d, J=7.1 Hz, 1H), APESI-MS m/z 508 (M+1)$^+$.

Example 16

[2-(4-Fluorophenyl)-3-(4-pyridinyl)pyrazolo[1,5-a]pyridin-5-yl]methyl 2-aminonicotinate

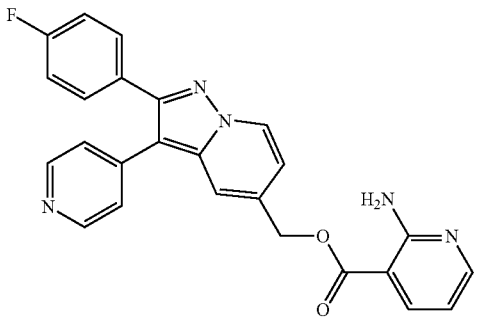

In a similar manner as described for Example 11, using 2-amino-3-pyridinecarboxylic acid in place of 4-pyridinecarboxylic acid, is obtained the title compound. $^1$H NMR (d$_6$-DMSO) δ 5.35 (s, 2H), 6.60 (dd, J=4.6, 7.8 Hz, 1H), 7.10 (d, J=7.2 Hz, 1H), 7.16 (bs, 2H), 7.23 (t, J=8.8 Hz, 2H), 7.29 (d, J=6.0 Hz, 2H), 7.51 (dd, J=5.7, 8.6 Hz, 2H), 7.82 (s, 1H), 8.08 (d, J=7.9 Hz, 1H), 8.20 (m, 1H), 8.54 (d, J=6.0 Hz, 2H), 8.80 (d, J=7.1 Hz, 1H); APESI-MS m/z 440 (M+1)$^+$.

Example 17

[2-(4-Fluorophenyl)-3-(4-pyridinyl)pyrazolo[1,5-a]pyridin-5-yl]methyl 3-(aminosulfonyl)-4-chlorobenzoate

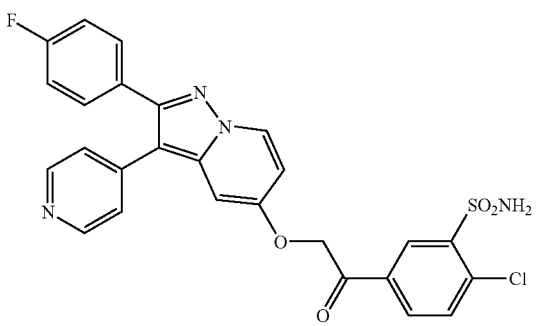

In a similar manner as described for Example 11, using 3-aminosulfonyl-4-chlorobenzoic acid in place of 4-pyridinecarboxylic acid, is obtained the title compound. $^1$H NMR (d$_6$-DMSO) δ 5.46 (s, 2H), 7.11 (d, J=7.4 Hz, 1H), 7.24 (t, J=8.9 Hz, 2H), 7.30 (d, J=6.0 Hz, 2H), 7.52 (dd, J=5.6, 8.5 Hz, 2H), 7.58 (s, 2H), 7.81 (d, J=8.4 Hz, 1H), 7.87 (s, 1H), 7.95 (dd, J=2.1, 8.1 Hz, 1H), 8.25 (d, J=2 Hz, 1H), 8.55 (d, J=5.8 Hz, 2H), 8.83 (d, J=7.2 Hz, 1H); APESI-MS m/z 537/539 (M+1)$^+$.

Example 18

[2-(4-Fluorophenyl)-3-(4-pyridinyl)pyrazolo[1,5-a]pyridin-5-yl]methyl 3-methyl-2-thiophenecarboxylate

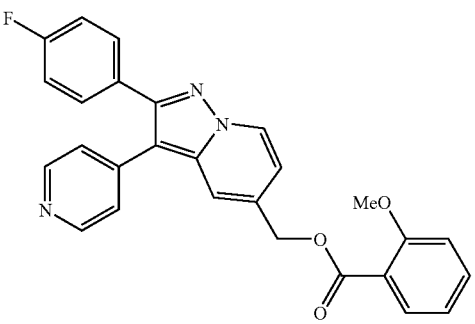

In a similar manner as described for Example 11, using 3-methyl-2-thiophenecarboxylic acid in place of 4-pyridinecarboxylic acid, is obtained the title compound. $^1$H NMR (d$_6$-DMSO) δ 2.47 (s, 3H), 5.37 (s, 2H), 7.07 (d, J=4.9 Hz, 1H), 7.12 (d, J=7.1 Hz, 1H), 7.27 (t, J=8.9 Hz, 2H), 7.49 (d, J=5.1 Hz, 2H), 7.53 (dd, J=5.6, 8.6 Hz, 2H), 7.80 (d, J=5 Hz, 1H), 7.91 (s, 1H), 8.63 (d, J=5.9 Hz, 2H), 8.87 (d, J=7.1 Hz, 1H), APESI-MS m/z 444 (M+1)$^+$.

Example 19

[2-(4-Fluorophenyl)-3-(4-pyridinyl)pyrazolo[1,5-a]pyridin-5-yl]methyl 2-methoxybenzoate

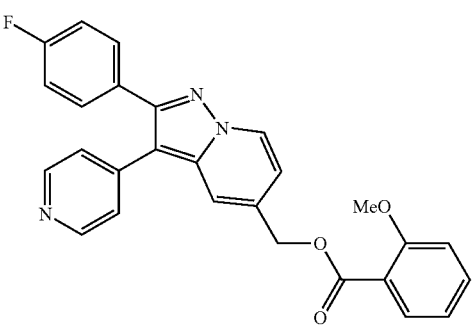

In a similar manner as described for Example 11, using 2-methoxybenzoic acid in place of 4-pyridinecarboxylic acid, is obtained the title compound. $^1$H NMR (d$_6$-DMSO) δ 3.75 (s, 3H), 5.39 (s, 2H), 7.01 (t, J=7.4 Hz, 1H), 7.15 (d, J=8.6 Hz, 1H), 7.20 (d, J=7.0 Hz, 1H), 7.28 (t, J=8.7 Hz, 2H), 7.50–7.60 (m, 3H), 7.62–7.73 (m, 3H), 7.98 (s, 1H), 8.69 (d, J=6.1 Hz, 2H), 8.90 (d, J=6.9 Hz, 1H); APESI-MS m/z 454 (M+1)$^+$.

Example 20

[2-(4-Fluorophenyl)-3-(4-pyridinyl)pyrazolo[1,5-a]pyridin-5-yl]methyl 2,3-dichlorobenzoate

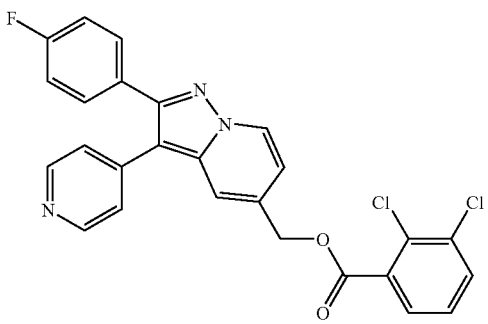

In a similar manner as described for Example 11, using 2,3-dichlorobenzoic acid in place of 4-pyridinecarboxylic acid, is obtained the title compound. $^1$H NMR (d$_6$-DMSO) δ 5.43 (s, 2H), 7.11 (d, J=7.2 Hz, 1H), 7.24 (t, J=8.8 Hz, 2H), 7.30 (d, J=5. Hz, 2H), 7.47–7.53 (m, 3H), 7.78 (d, J=5.4 Hz, 1H), 7.83–7.87 (m, 2H), 8.55 (d, J=5.9 Hz, 2H), 8.81 (d, J=7.1 Hz, 1H); APESI-MS m/z 492/494/496 (M+1)$^+$.

Example 21

2-[2-(4-Fluorophenyl)-3-(4-pyridinyl)pyrazolo[1,5-a]pyridin-5-yl]methyl-1H-isoindole-1,3(2H)-dione

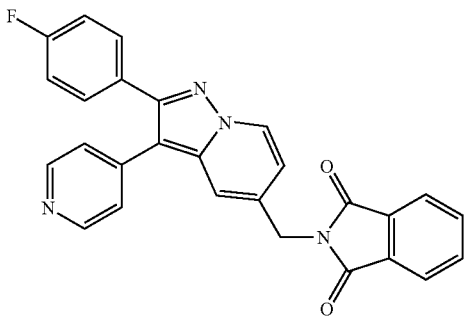

2-(4-Fluorophenyl)-5-hydroxymethyl-3-(4-pyridinyl)pyrazolo[1,5-a]pyridine (Example 6. 68 mg, 0.213 mmol), triphenyl phosphine (168 mg, 0.64 mmol) and phthalimide (63 mg, 0.43 mmol) are dissolved in dry THF (3 mL). The stirred solution is cooled to 0° C. and diethyl azodicarboxylate (105 mg of 85% grade, 0.51 mmol) is added dropwise. The solution is stirred at 0° C. for 2 h during which time a white solid deposits and then stirred for 16 h at room temperature. The solution is then diluted with ether (20 mL) and the deposited solid filtered off. The solid is washed with ether and dried to give the first batch of product (20 mg). The ether solution is then washed with water and then extracted with dilute hydrochloric acid. A portion of the product deposits and is filtered off, washed twice with ether and dried to give the product as the hydrochloride salt (16 mg). The acidic phase is washed with ether and then made alkaline with sodium bicarbonate solution. Extraction with ethyl acetate (50 mL×3) followed by drying (MgSO$_4$) and concentration gives the product as an off-white solid (32 mg). $^1$H NMR (d$_6$-DMSO) δ 4.83 (s, 2H), 6.91 (dd, J=1.8, 7.2 Hz, 1H), 7.22 (t, J=8.9 Hz, 2H), 7.26 (d, J=5.9 Hz, 2H), 7.49 (dd, J=5.6, 8.6 Hz, 2H), 7.71 (s, 1H), 7.81–7.89 (m, 4H), 8.54 (d, J=4.7 Hz, 2H), 8.72 (d, J=7.1 Hz, 1H); APESI-MS m/z 449 (M+1)$^+$

Example 22

[2-(4-Fluorophenyl)-3-(4-pyridinyl)pyrazolo[1,5-a]pyridin-5-yl]methanamine

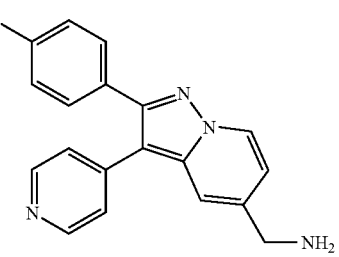

[2-(4-Fluorophenyl)-3-(4-pyridinyl)pyrazolo[1,5-a]pyridin-5-yl]methyl 3-(aminosulfonyl)-4-chlorobenzoate (Example 17 106 mg, 0.23 mmol) is dissolved in ethanol (10 mL) and hydrazine (64 mg, 2 mmol) added. The solution is refluxed for 6 h and allowed to cool. A precipitate of phthalhydrazide is filtered off and the mother liquor concentrated to dryness. The crude solid is taken up in dilute hydrochloric acid (20 mL), and washed twice with ethyl acetate (15 mL) followed by basification with sodium hydroxide solution. The solution is extracted five times with dichloromethane (20 mL), dried (MgSO$_4$) and concentrated to give a solid (43 mg). Purified by preparative TLC, eluting with ethyl acteate plus 2% methanol, to give the title compound, 23 mg. $^1$H NMR (d$_6$-DMSO) δ 3.75 (s, 2H), 6.97 (d, J=7.3 Hz, 1H), 7.22 (t, J=8.9 Hz, 2H), 7.28 (d, J=5.9 Hz, 2H), 7.50 (dd, J=5.7, 8.4 Hz, 2H), 7.64 (s, 1H), 8.53 (d, J=5.7 Hz, 2H), 8.68 (d, J=7.2 Hz, 1H); APESI-MS m/z 319 (M+1)$^+$.

Example 23

2-(4-Fluorophenyl)-3-(4-pyridinyl)-6-(trifluoromethyl)pyrazolo[1,5-a]pyridine

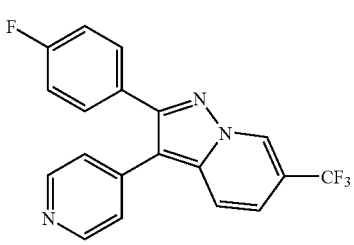

In a similar manner as described in Examples 2a, 2b, 1d, 1e and 1f, from 3-trifluoromethylpyridine was obtained the title compound as a white solid. $^1$H NMR (d$_6$-DMSO) δ 7.27 (t, 2H, J=8.8 Hz), 7.32 (d, 2H, J=6.0 Hz), 7.54 (m, 3H), 7.87 (d, 2H, J=9.6 Hz), 8.58 (d, 2H, J=5.6 Hz), 9.47 (s, 1H). MS (ES+) m/z 358 (M$^+$+H).

Example 24

2-(4-Fluorophenyl)-3-(4-pyridinyl)pyrazolo[1,5-a]pyridin-5-ol

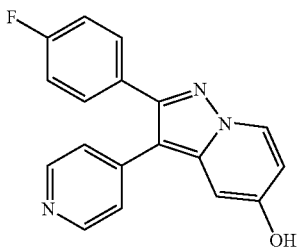

A solution of 2-(4-fluorophenyl)-3-(4-pyridyl)-5-methoxypyrazolo[1,5-a]pyridine (Example 5. 0.05 g, 0.16 mmol) in dry $CH_2Cl_2$ was cooled to about −78° C. under nitrogen. Boron tribromide (0.8 mL of a 1M solution in $CH_2Cl_2$, 0.8 mmol) was added dropwise and the mixture was stirred and warmed to room temperature over about 24 h. Ice was added to the reaction mixture and the resulting slurry was stirred for about 15 min. The $CH_2Cl_2$ was evaporated under vacuum and the resulting aqueous slurry was treated with conc hydrochloric acid (1 mL) and stirred. The aqueous solution was basified by the addition of a saturated solution of $NaHCO_3$, and the resulting solid was collected by filtration and was dried under vacuum to give the title compound.

Example 25

5-(n-Butoxy)-2-(4-fluorophenyl)-3-(4-pyridinyl)pyrazolo[1,5-a]pyridine

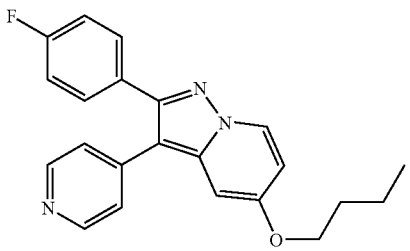

2-(4-Fluorophenyl)-3-(4-pyridinyl)pyrazolo[1,5-a]pyridin-5-ol (Example 24. 0.5 g, 1.63 mmol) was dissolved in dimethylformamide (10 mL) and potassium tert butoxide (2.5 mL of a 1 M solution in THF, 2.5 mmol) was added dropwise to the stirred solution. After 10 minutes iodobutane (2 mmol) was added and the reaction stirred at room temperature. Second additions of iodobutane (0.88 mmol) and 1M potassium tertbutoxide (2.5 mL, 1 mmol) were made after 4 h and reaction stirred further until complete by TLC. Water (100 mL) was added and the resulting aqueous solution was extracted with with dichloromethane (4×100 mL), the combined organic solution was dried ($MgSO_4$), filtered and concentrated to give the crude product. This was purified either by silica gel chromatography to give the title compound (58%). $^1H$ NMR ($d_6$-DMSO) δ 0.93 (t, J=7.3 Hz, 3H), 1.43 (quintet, J=7.3 Hz, 2H), 1.74 (quintet, J=7.3 Hz, 2H), 4.13 (t, J=6.9 Hz, 2H), 6.84 (dd, J=2.4, 7.5 Hz, 1H), 7.21 (d, J=2.4 Hz, 1H), 7.28 (t, J=8.8 Hz, 2H), 7.53 (dd, J=0.5, 8.8 Hz, 2H), 7.73 (d, J=6.4 Hz, 2H), 8.65 (d, J=6.4 Hz, 2H), 8.74 (d, J 7.5 Hz, 1H); APESI-MS m/z 362 (M+1)$^+$.

Example 26

5-(Benzyloxy)-2-(4-fluorophenyl)-3-(4-pyridinyl)pyrazolo[1,5-a]pyridine

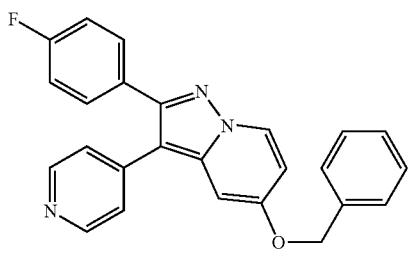

In a similar manner as described in Example 25, using benzyl bromide in place of iodobutane, was obtained the title compound (43%). $^1H$ NMR ($d_6$-DMSO) δ 5.20 (s, 2H), 6.77 (dd, J=2.5, 7.5 Hz, 1H), 7.08 (d, J=2.5 Hz, 1H), 7.19–7.31 (m, 4H), 7.34 (d, J=7.1 Hz, 1H), 7.40 (t, J=7.4 Hz, 2H), 7.45–7.49 (m, 4H), 8.51 (d, J=5.6 Hz, 2H), 8.66 (d, J=7.5 Hz, 1H); APESI-MS m/z 396 (M+1)$^+$

Example 27

2-(4-Fluorophenyl)-3-(2-fluoro-4-pyridinyl)pyrazolo[1,5-a]-pyridine

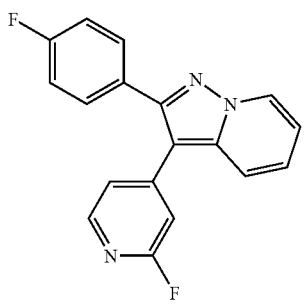

A solution of 3-bromo-2-(4-fluorophenyl)-pyrazolo[1,5-a]pyridine (Example le. 1.30 g, 4.5 mmol), 2-fluoro-4-pyridinylboronic acid (Example 46a. 694 mg, 4.9 mmol) and dichlorobis(triphenylphosphine)palladium (316 mg, 0.45 mmol) in DMF (100 mL) was placed in a pre-heated oil bath at 110° C. To the reaction was added, in a dropwise manner, 2M aqueous sodium carbonate (4.5 mL, 9.0 mmol). The reaction was allowed to stir for 2 h and then cooled to room temperature and filtered through a pad of Celite. The Celite pad was washed with ethyl acetate and the filtrate was concentrated to dryness at 50° C. under vacuum. The residue was partitioned between ethyl acetate and water. The layers were separated and the organic phase was dried ($MgSO_4$). The drying agent was removed by filtration and the filtrate was concentrated and purified by silica gel chromatography to yield the title compound (378 mg, 1.23 mmol, 27%). $^1H$ NMR ($CDCl_3$) δ 8.57 (d, 1H, J=6.9 Hz), 8.22(d, 1H, J=5.4 Hz), 7.7(d, 1H, J=9.0 Hz), 7.75(m, 2H), 7.33(m, 1H), 7.14(m, 3H), 6.95(m, 2H). MS (ES+ve) 308 (100, M+).

Example 28

4-[2-(4-Fluorophenyl)pyrazolo[1,5-a]pyridin-3-yl]-N-[2-(1H-imidazol-5-yl)ethyl]-2-pyridinamine

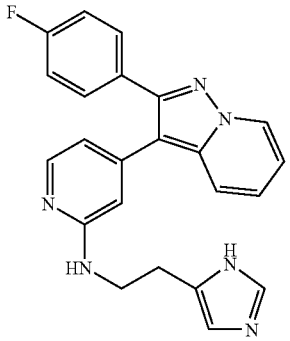

In a sealed-tube was combined 2-(4-fluorophenyl)-3-(2-fluoro-4-pyridinyl)pyrazolo[1,5-a]pyridine (Example 27. 30 mg, 0.10 mmol) and histamine (40 mg, 0.36 mmol), and the reaction was placed in a pre-heated oil bath at 140° C. The reaction was stirred at 140° C. until consumption of starting material was indicated by TLC analysis (50% ethyl acetate in hexanes). The contents of the sealed-tube were transferred to a flask and concentrated to dryness at 50° C. under high vacuum. The residue was purified by silica gel chromatography to yield the title compound, 23 mg (0.06 mmol, 60%). $^1$H NMR ($d_6$-DMSO) δ 11.8 (brs, 1H), 8.73 (d, 1H, J=6.8 Hz), 7.94 (d, 1H, J=5.3 Hz), 7.63 (d, 1H, J=9.3 Hz), 7.57 (dd, 2H, J=5.3, 8.6 Hz), 7.48 (s, 1H), 7.30 (t, 1H, J=7.6 Hz), 7.23 (t, 2H, J=9.0 Hz), 6.97 (t, 1H, J=6.8 Hz), 6.75 (brs, 1H), 6.57 (br t, 1H, J=5.3 Hz), 6.44 (s, 1H), 6.33 (d, 1H, J=5.3 Hz), 3.41 (q, 2H, J=6.6 Hz), 2.7 (t, 2H, J=6.6 Hz). MS (ES+ve): 399.1 (50, M+), 305.3 (90), 169.4 (100).

Example 29

N-Butyl-4-[2-(4-fluorophenyl)pyrazolo[1,5-a]pyridin-3-yl]-2-pyridinamine

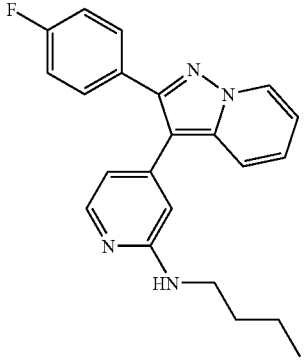

In a similar manner as described in Example 28, using butylamine in place of histamine, was obtained the title compound. $^1$H NMR (CD$_2$Cl$_2$) δ 8.49 (d, 1H, J=7.2 Hz), 8.01 (d, 1H. J=5.2 Hz), 7.62 (m, 3H), 7.21(m, 1H,), 7.07(t, 2H, J=8.8 Hz), 6.85 (m, 2H), 6.54 (dd, 1H, J=4.8, 0.8 Hz), 6.32 (s, 1H), 3.16 (quart, 2H, J=6.4 Hz), 1.53 (quint, 2H, J=7.2 Hz), 1.37 (sext, 2H, J=Hz), 0.92 (t, 3H, J=7.2 Hz). MS (ES+ve) 361 (100, M+).

Example 30

3-(4-[2-(4-Fluorophenyl)pyrazolo[1,5-a]pyridin-3-yl]-2-pyridinylamino)-1-propanol

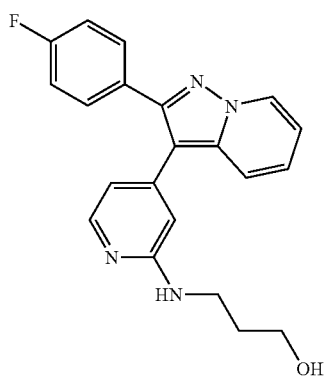

In a similar manner as described in Example 28, using 3-hydroxypropylamine in place of histamine, was obtained the title compound. $^1$H NMR (CD$_2$Cl$_2$) δ 8.55 (d, 1H, J=6.9 Hz), 8.04 (d, 1H, J=5.4 Hz), 7.66 (m, 3H), 7.26 (m, 2H), 7.13 (t, 2H, J=8.7 Hz), 6.90 (t, 1H, J=6.9 Hz), 6.57 (d, 1H, J=5.1 Hz), 6.43 (s, 1H), 4.50 (t, 1H, J=5.7 Hz), 3.66 (t, 2H, J=5.7 Hz), 3.55 (quart, 2H, J=6.0 Hz), 1.76 (quint, 2H, J=5.7 Hz). MS (ES+ve): 363 (100, M+).

Example 31

N-(4-Chlorobenzyl)-4-[2-(4-fluorophenyl)pyrazolo[1,5-a]pyridin-3-yl]-2-pyridinamine

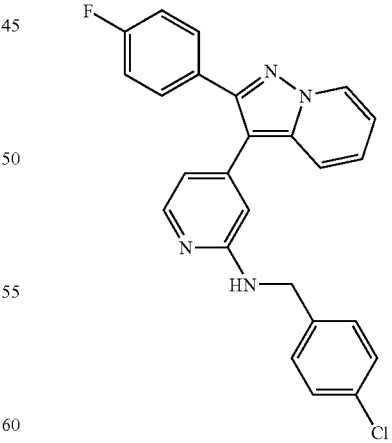

In a similar manner as described in Example 28, using 4-chlorobenzylamine in place of histamine, was obtained the title compound. $^1$H NMR (CD$_2$Cl$_2$) δ 8.53 (d, 1H, J=6.9 Hz), 8.04 (d, 1H, J=5.4 Hz), 7.62 (dd, 2H, J=5.7, 8.7 Hz), 7.35 (m, 3H), 7.23 (t, 2H, J=8.7 Hz), 7.15 (t, 2H, J=8.7 Hz), 6.91

(t, 2H, J=6.9 Hz), 6.62 (d, 1H, J=5.7 Hz), 6.41 (s, 1H), 4.51 (d, 2H, J=5.7 Hz). MS (ES+ve): 428 (40, M+), 430 (30, M+3), 125 (100).

Example 32

N$^{1-4}$-[2-(4-Fluorophenyl)pyrazolo[1,5-a]pyridin-3-yl]-2-pyridinyl-1,3-propanediamine

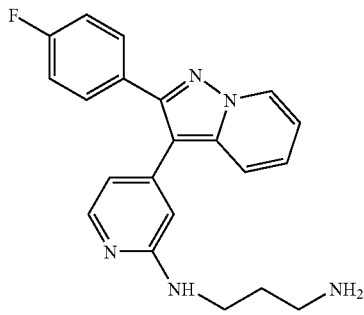

In a similar manner as described in Example 28, using 1,3-diaminopropane in place of histamine, was obtained the title compound. $^1$H NMR (CD$_2$Cl$_2$) δ 8.55 (d, 1H, J=5.4 Hz), 8.08(d, 1H, J=3.9 Hz), 7.69(m, 3H), 7.25 (dd, 1H, J=5.7, 8.7), 7.12(t, 2H, J=6.6 Hz), 6.9(t, 1H, J=6.9 Hz), 6.59(d, 1H, J=5.7 Hz), 6.4(s, 1H), 5.02(m, 1H), 3.33(q, 2H, J=5.1 Hz), 2.82(t, 2H, J=5.4 Hz), 1.72(n, 2H, J=5.4 Hz). MS (ES+ve): 362 (100, M+).

Example 33

3-(2-Butoxy-4-pyridinyl)-2-(4-fluorophenyl)pyrazolo[1,5-a]pyridine

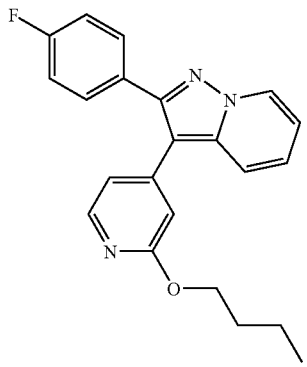

In a similar manner as described in Example 28, using 1-butanol in place of histamine, was obtained the title compound. $^1$H NMR (acetone-d$_6$) δ 8.70 (d, 1H, J=7.2 Hz), 8.16 (d, 1H, J=5.4 Hz), 7.76 (d, 1H, J=9.0 Hz), 7.68. (m, 2H), 7.40 (dd, 1H, J=6.9, 8.7 Hz), 7.23 (m, 2H), 7.06 (dt, 1H, J=6.9, 1.2 Hz), 6.80 (dd, 1H, J=5.4, 1.5 Hz), 6.77 (s, 1H), 4.36(t, 2H, J=6.6 Hz), 1.77(quint, 2H, J=3.9 Hz), 1.5(sext, 2H, J=7.5 Hz), 1.0(t, 3H, J=7.5 Hz). MS (ES+ve): 362 (40, M+), 306 (100).

Example 34

4-[2-(4-Fluorophenyl)pyrazolo[1,5-a]pyridin-3-yl]-N-hexyl-2-pyridinamine

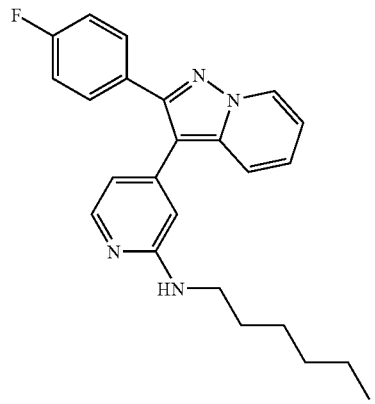

In a similar manner as described in Example 28, using hexylamine in place of histamine, was obtained the title compound. $^1$H NMR (acetone-d$_6$) δ 8.67 (d, 1H, J=7.2 Hz), 8.05 (d, 1H, J=5.4 Hz), 7.72 (m, 3H), 7.33 (dd, 1H, J=7.2, 8.4 Hz), 7.21 (t, 2H, J=9.0 Hz), 7.00 (td, 1H, J=6.9, 0.9 Hz), 6.50 (s, 1H), 6.49 (d, 1H, J=5.1 Hz), 5.85 (t, 1H, J=5.1 Hz), 3.34 (quart, 2H, J=6.0 Hz), 1.61 (quint, 2H, J=6.9 Hz), 1.36 (m, 6H), 0.92 (t, 3H, J=2.4 Hz). MS (ES+ve): 389 (100, M+).

Example 35

4-[2-(4-Fluorophenyl)pyrazolo[1,5-a]pyridin-3-yl]-N-(4-methoxybenzyl)-2-pyridinamine

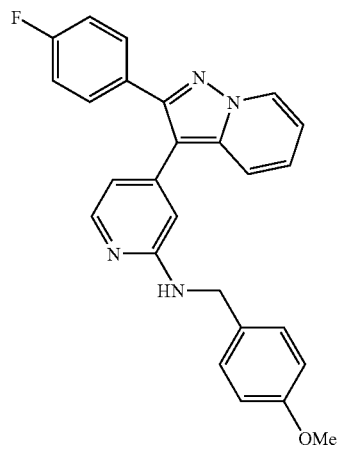

In a similar manner as described in Example 28, using 4-methoxybenzylamine in place of histamine, was obtained the title compound. $^1$H NMR (d$_6$ DMSO) δ 8.79 (d, 1H, J=7.2 Hz), 7.98 (d, 1H, J=5.4 Hz), 7.62 (dd, 2H, J=5.4, 8.4 Hz), 7.53 (d, 1H, J=9.0 Hz), 7.29 (m, 5H), 7.04 (quart, 2H, J=5.7 Hz), 6.92 (d, 2H, J=8.7 Hz), 6.51 (s, 1H), 6.38 (d, 1H, J=5.1 Hz).

Example 36

4-[2-(4-Fluorophenyl)pyrazolo[1,5-a]pyridin-3-yl]-N-pentyl-2-pyridinamine

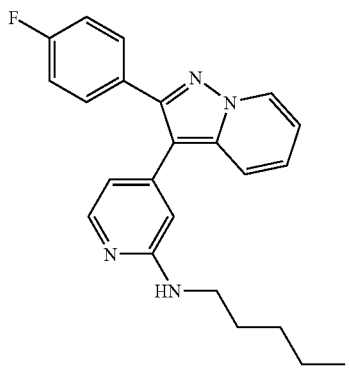

In a similar manner as described in Example 28, using pentylamine in place of histamine, was obtained the title compound. $^1$H NMR (acetone-$d_6$) δ 8.66 (d, 1H, J=6.9 Hz), 8.05 (d, 1H, J=5.1 Hz), 7.73 (m, 3H), 7.65 (t, 2H, J=9.0 Hz), 7.22 (t, 2H, J=2.1 Hz), 7.02 (td, 1H, J=6.9, 1.2 Hz), 6.51 (s, 1H), 6.50 (d, 1H, J=5.4 Hz), 5.82 (m, 1H), 3.34 (quart, 2H, J=6.3 Hz), 1.63 (quint, 2H, J=6.9 Hz), 1.39 (m, 4H), 0.94 (t, 3H, J=6.3 Hz).

Example 37

4-[2-(4-Fluorophenyl)pyrazolo[1,5-a]pyridin-3-yl]-N-(3-pyridinylmethyl)-2-pyridinamine

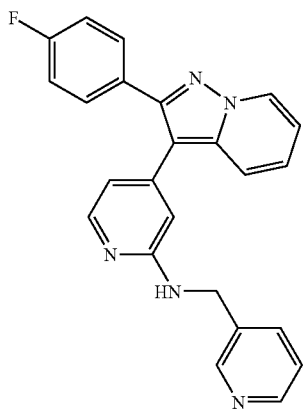

In a similar manner as described in Example 28, using 3-(aminomethyl)pyridine in place of histamine, was obtained the title compound. $^1$H NMR (acetone-$d_6$) δ 8.50 (d, H, J=6.8 Hz), 8.32 (d, H, J=4.0 Hz), 7.90 (d, H, J=5.2 Hz), 7.63 (d, H, J=7.6 Hz), 7.52 (m, H), 7.46 (d, H, J=9.2 Hz), 7.16 (m, H), 7.04 (t, H, J=8.8 Hz), 6.85 (t, H, J=6.4 Hz), 6.45 (s, H), 6.37 (d, H, J=4.4 Hz). MS (ES+ve): 396 (60, M$^+$), 109 (100).

Example 38

4-[2-(4-Fluorophenyl)pyrazolo[1,5-a]pyridin-3-yl]-N-propyl-2-pyridinamine

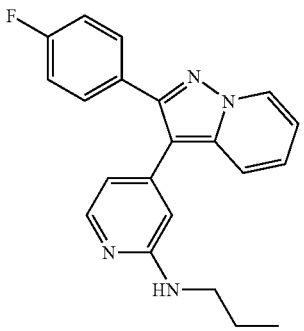

In a similar manner as described in Example 28, using propylamine in place of histamine, was obtained the title compound. $^1$H NMR (acetone-$d_6$) δ 8.67 (d, 1H, J=7.2 Hz), 8.05 (d, 1H, J=5.1 Hz), 7.72 (m, 3H), 7.35 (dd, 1H, J=6.9, 9.0 Hz), 7.22 (t, 2H, J=9.0 Hz), 7.03 (t, 1H, J=6.6 Hz), 6.51 (s, 1H), 6.50 (d, H, J=7.2 Hz), 5.84 (m, 1H), 3.31 (quart, 2H, J=6.6 Hz), 1.63 (sext, 2H, J=7.2 Hz), 0.98 (t, 3H, J=Hz). MS (ES+ve): 347 (100, M$^+$).

Example 39

4-[2-(4-Fluorophenyl)pyrazolo[1,5-a]pyridin-3-yl]-N-phenyl-2-pyridinamine

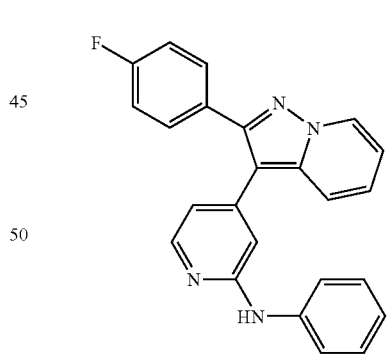

In a similar manner as described in Example 28, using aniline in place of histamine, was obtained the title compound. $^1$H NMR (acetone-$d_6$) δ 8.70 (d, 1H, J=6.9 Hz), 8.32 (s, 1H), 8.24 (d, 1H, J=5.4 Hz), 7.80 (d, 1H, J=9.0 Hz), 7.73 (m, 3H), 7.67 (d, 1H, J=8.1 Hz), 7.40 (dd, 1H, J=6.9, 8.4 Hz), 7.26 (m, 4H), 7.06 (dt, 1H, J=6.9, 1.2 Hz), 6.95 (t, 1H, J=7.5 Hz), 6.90 (s, 1H), 6.79 (dd, 1H, J=5.4, 1.5 Hz). MS(ES+ve): 381 (100, M$^+$).

Example 40

N$^{1-4}$-[2-(4-Fluorophenyl)pyrazolo[1,5-a]pyridin-3-yl]-2-pyridinyl-1,4-butanediamine

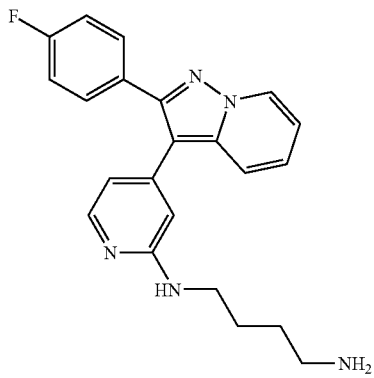

In a similar manner as described in Example 28, using 1,4-diaminobutane in place of histamine, was obtained the title compound. $^1$H NMR (acetone-d$_6$) δ 8.66 (d, 1H, J=6.9 Hz), 8.04 (d, 1H, J=5.1 Hz), 7.72 (m, 3H), 7.34 (dd, 1H, J=6.6, 9.0 Hz), 7.21 (t, 2H, J=8.7 Hz), 7.01 (t, 1H, J=6.9 Hz), 6.53 (s, 1H), 6.49 (d, 1H, J=4.2 Hz), 6.01 (t, 1H, J=5.1 Hz), 3.34 (m, 2H), 2.23 (m, 2H), 2.10 (m, 2H), 1.70 (m, 2H).

Example 41

2-(4-[2-(4-Fluorophenyl)pyrazolo[1,5-a]pyridin-3-yl]-2-pyridinylamino)-1-ethanol

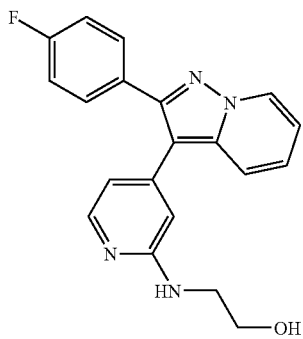

In a similar manner as described in Example 28, using 2-hydroxyethylamine in place of histamine, was obtained the title compound. $^1$H NMR (d$_6$ DMSO) δ 8.79 (d, 1H, J=6.9 Hz), 7.96 (d, 1H, J=5.4 Hz), 7.69 (d, 1H, J=9.0 Hz), 7.62 (m, 2H), 7.36 (dd, 1H, J=8.7, 6.9 Hz), 7.29 (m, 2H), 7.03 (t, 1H, J=6.6 Hz), 6.56 (m, 2H), 6.36 (d, 1H, J=5.1 Hz), 3.53 (t, 2H, J=5.7 Hz), 3.34 (m, 2H). MS (ES+ve): 349 (100, M+). MS (ES+ve): 437 (100, M$^+$).

Example 42

N-Benzyl-4-[2-(4-fluorophenyl)pyrazolo[1,5-a]pyridin-3-yl]-2-pyridinamine

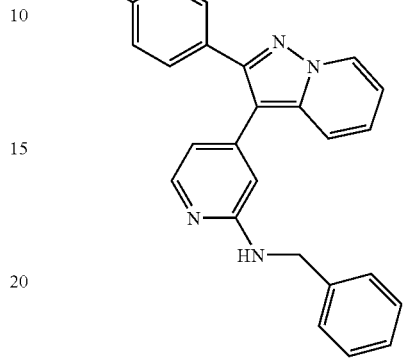

In a similar manner as described in Example 28, using benzylamine in place of histamine, was obtained the title compound. $^1$H NMR (acetone-d$_6$) δ 8.65 (d, 1H, J=6.9 Hz), 8.06 (d, 1H, J=5.1 Hz), 7.70 (m, 2H), 7.54 (d, 1H, J=8.7 Hz), 7.31 (m, 7H), 7.01 (t, 1H, J=6.9 Hz), 6.58 (s, 1H), 6.51 (dd, 1H, J=1.5, 5.1 Hz), 6.38 (m, 1H), 4.62 (m, 2H). MS (ES+ve): 395 (100, M$^+$).

Example 43

4-[2-(4-Fluorophenyl)pyrazolo[1,5-a]pyridin-3-yl]-N,N-dimethyl-2-pyridinamine

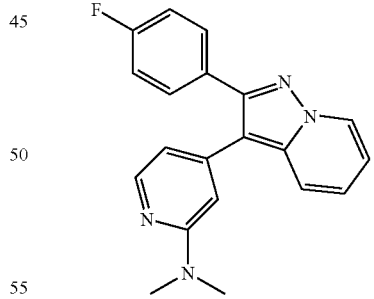

In a similar manner as described in Example 28, using N,N-dimethylamine in place of histamine, was obtained the title compound. $^1$H NMR (CD$_2$Cl$_2$) δ 8.55(d, 1H, J=9.3 Hz), 8.17(d, 1H, J=6.5 Hz), 7.64–7.74(m, 3H), 7.25(dd, 1H, J=8, 11.5 Hz), 7.12 (t, 2H, J=11.5 Hz), 6.90 (t, 1H, J=9.3 Hz), 6.57 (d, 1H, J=6.5 Hz), 6.54(s, 1H), 3.06(s, 6H). MS (ES+ve): 333.2 (100, M$^+$).

Example 44

3-(2,6-Difluoro-4-pyridinyl)-2-(4-fluorophenyl)pyrazolo[1,5-a]pyridine

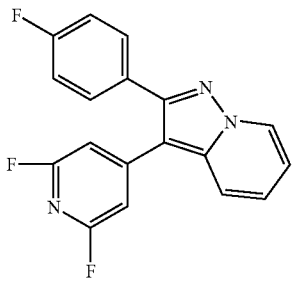

A solution of 3-bromo-2-(4-fluorophenyl)-pyrazolo[1,5-a]pyridine (from Example 1e, 570 mg, 1.96 mmol), 2,6-difluoro-4-pyridyl-boronic acid (340 mg, 2.15 mmol) and dichlorobis(triphenylphosphine)palladium (137 mg, 0.196 mmol) in DMF (10.0 mL) was placed in a pre-heated oil bath at 110° C. To the reaction was added, in a dropwise manner, 2M sodium carbonate (2.00 mL, 4.00 mmol). The reaction was allowed to stir for 45 min before cooling to room temperature and filtering through a Celite 545 pad. The Celite filter was washed with ethyl acetate and the filtrate was concentrated to dryness at 50° C. under vacuum. The residue was dissolved in methylene chloride and dried (MgSO$_4$). The drying agent was removed by filtration and the filtrate was concentrated and purified by silica gel chromatography to yield the title compound (160 mg, 0.492 mmol, 25%). $^1$H NMR (CDCl$_3$) δ 8.53(d, 1H, J=6.8 Hz), 7.67(d, 1H, J=8.8 Hz), 7.53(dd, 2H, J=5.6, 8.0 Hz), 7.31(t, 1H, J=7.6 Hz), 7.11(t, 2H, J=8.4 Hz), 6.93(t, 1H, J=6.8 Hz), 6.75(s, 2H). MS (ES+ve): 326 (90, M$^+$).

Example 45

N-Benzyl-6-fluoro-4-[2-(4-fluorophenyl)pyrazolo[1,5-a]pyridin-3-yl]-2-pyridinamine

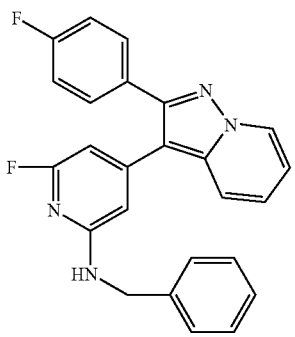

In a sealed-tube was combined 3-(2,6-difluoro-4-pyridinyl)-2-(4-fluorophenyl)pyrazolo[1,5-a]pyridine (Example 44, 35 mg, 0.11 mmol) and benzylamine (3.0 mL, 2.9 g, 27 mmol), and the reaction was placed in a preheated oil bath at 130° C. The reaction was stirred at 130° C. until consumption of starting material was indicated by TLC analysis (50% ethyl acetate in hexanes). The contents of the sealed-tube was transferred to a flask and concentrated to dryness at 50° C. under high vacuum. The residue was purified by silica gel chromatography to yield the title compound, 18 mg (0.04 mmol, 36%). $^1$H NMR (d$_6$-acetone) δ 8.67(d, 1H, J=6.8 Hz), 7.71(dd, 2H, J=5.6, 8.8 Hz), 7.59(d, 1H J=8.8 Hz), 7.30–7.45(m, 6H), 7.24(t, 2H, J=8.8 Hz), 7.05(t, 1H, J=6.8 Hz) 6.73(br t, 1H, J=6.0 Hz), 6.46(s, 1H), 6.09(s, 1H), 4.59(d, 2H, J=6.0 Hz). MS (ES+ve): 413.1 (100, M$^+$).

Example 46

2-(4-Fluorophenyl)-3-(2-fluoro-4-pyridinyl)-6-trifluoromethylpyrazolo[1,5-a]pyridine

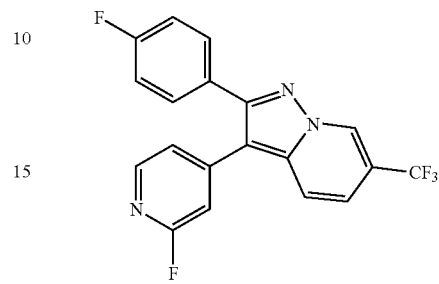

a) 2-Fluoropyridin-4-ylboronic Acid

To a stirred solution of n-butyl lithium (3.2 mL, 2.5M, 8.0 mmol) in dry diethyl ether (20 mL) at −78° C. was added a solution of 2-fluoro-4-iodopyridine (1.5 g, 6.7 mmol) in dry ether (10 mL) and the reaction mixture was stirred at −78° C. for 10 min. Tributyl borate (2.4 mL, 2.01 g, 8.7 mmol) was added and the reaction mixture was allowed to stir to room temperature over 2 h. Water (5 mL) was added followed by 2N aqueous sodium hydroxide solution (10 mL) to dissolve the solids. The organic phase was separated. The aqueous phase was acidified to pH 3 using 6N HCl and the resulting white solid was collected by filtration and dried under vacuum to give the title compound, 0.74 g (78%). 1H NMR (d$_6$ DMSO) δ 8.65 (br s, 2H), 8.21 (d, 1H, J=4.8 Hz), 7.59 (t, 1H, J=4.8 Hz), 7.37 (d, 1H, J=1.8 Hz).

b) 2-(4-Fluorophenyl)-3-(2-fluoro-4-pyridinyl)-6-trifluoromethylpyrazolo[1,5-a]pyridine In a similar manner as described in Example 27, from 2-fluoro-4-pyridylboronic acid and 3-bromo-2-(4-fluorophenyl)-6-trifluoromethylpyrazolo[1,5-a]pyridine (intermediate from Example 23) was obtained the title compound. $^1$H NMR (CDCl$_3$) δ 8.85(s, 1H,), 8.22(d, 1H, J=5.2 Hz), 7.70 (d, 1H, J=9.6 Hz), 7.52(dd, 2H, J=5.2, 8.4 Hz), 7.38(d, 1H, 9.6 Hz), 7.09(t, 2H, J=8.4 Hz), 6.90(s, 1H). MS (ES+ve): 376 (100, M$^+$).

Example 47

4-[2-(4-Fluorophenyl)-6-trifluoromethylpyrazolo[1,5-a]pyridin-3-yl]-N-isopropyl-2-pyridinamine

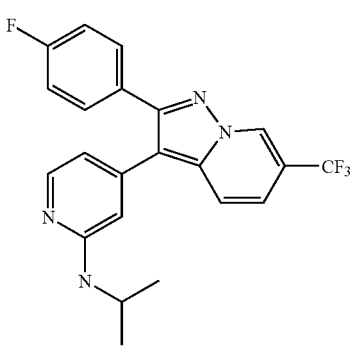

In a similar manner as described in Example 28 using 2-(4-fluorophenyl)-3-(2-fluoro-4-pyridinyl)-6-trifluoromethylpyrazolo[1,5-a]pyridine (Example 46) and isopropylamine was obtained the title compound. ¹H NMR (d₆-acetone) δ 9.12 (s, 1H), 8.04 (d, 1H, J=5.1 Hz), 7.85 (d, 1H, J=9.3 Hz), 7.70 (dd, 2H, J=5.4, 8.7 Hz), 7.50(d, 1H, J=9.3 Hz), 7.21(t, 2H, J=8.7 Hz), 6.49(s, 1H), 6.45(d, 1H, J=5.1 Hz), 5.63(brd, 1H), 4.04(m, 1H), 1.20 (d, 6H, J=4.8 Hz). MS (ES+ve): 415 (100, M⁺).

Example 48

N-Cyclopropyl-4-[2-(4-fluorophenyl)-6-trifluoromethylpyrazolo[1,5-a]pyridin-3-yl]-2-pyridinamine

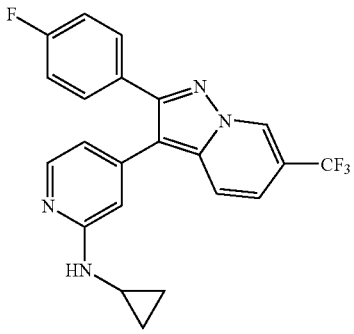

In a similar manner as described in Example 28 using 2-(4-fluorophenyl)-3-(2-fluoro-4-pyridinyl)-6-trifluoromethylpyrazolo[1,5-a]pyridine (Example 46) and cyclopropylamine was obtained the title compound. ¹H NMR (d₆ DMSO) δ 9.13 (s, 1H), 7.72(d, 1H, J=5.1 Hz), 7.55(d, 1H, J=9.3 Hz), 7.27(m, 3H), 6.99(t, 2H, J=9 Hz), 6.54(s, 1H), 6.21(d, 1H, J=5.1 Hz), 6.21(s, 1H), 2.05(m, 1H), 0.23(m, 2H), 0.02(m, 2H). MS (ES+ve): 413 (75%, M⁺).

Example 49

3-(4-[2-(4-Fluorophenyl)-6-trifluoromethylpyrazolo[1,5-a]-pyridin-3-yl]-2-pyridinylamino)-1-propanol

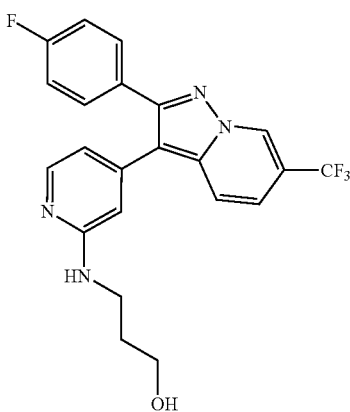

In a similar manner as described in Example 28 using 2-(4-fluorophenyl)-3-(2-fluoro-4-pyridinyl)-6-trifluoromethylpyrazolo[1,5-a]pyridine (Example 46) and 3-hydroxypropylamine was obtained the title compound. ¹H NMR (d₆-DMSO) δ 9.41(s, 1H), 7.95(d, 1H, J=5.2 Hz), 7.78(d, 1H, 9.2 Hz), 7.58(dd, 2H, J=5.6, 8.8 Hz), 7.50(d, 1H, J=9.6 Hz), 7.26(t, 2H, J=8.8 Hz), 6.544(br t, 1H, J=5.6 Hz), 6.42(s, 1H), 6.33(d, 1H, J=5.6 Hz), 6.46(m, 1H), 3.43(m, 2H), 3.22(br q, 2H, J=6.8 Hz), 1.62(quint, 2H, J=6.4 Hz). MS (ES+ve): 431(100, M⁺).

Example 50

6-Bromo-2-(4-fluorophenyl)-3-(2-fluoro-4-pyridinyl)pyrazolo[1,5-a]pyridine

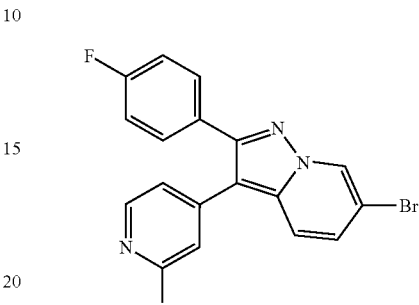

To a solution of 2-(4-fluorophenyl)-3-(2-fluoro-4-pyridinyl)pyrazolo[1,5-a]pyridine (Example 27. 937 mg, 3.05 mmol) in DMF (20 mL) was added N-bromosuccinimide (651 mg, 3.66 mmol). The reaction mixture was heated at 60° C. for about 5 h and then allowed to cool to room temperature. Saturated sodium bicarbonate was added and the mixture was extracted with dichloromethane. The organic extracts were dried (MgSO₄) and the solvents removed under vacuum. The residue was purified by silica gel chromatography to give the title compound. 0.604 g (50%). ¹H NMR (CDCl₃) δ 8.68 (s, 1H), 8.20 (d, 1H, J=5.4 Hz), 7.53 (m, 3H), 7.35 (dd, 1H, J=9.3, 1.2 Hz), 7.10 (m, 3H), 7.00 (s, 1H). MS (ES+ve) 387 (50, M⁺, M+3).

Example 51

N-(3-Aminopropyl)-4-[6-bromo-2-(4-fluorophenyl)pyrazolo[1,5-a]pyridin-3-yl]-2-pyridinamine

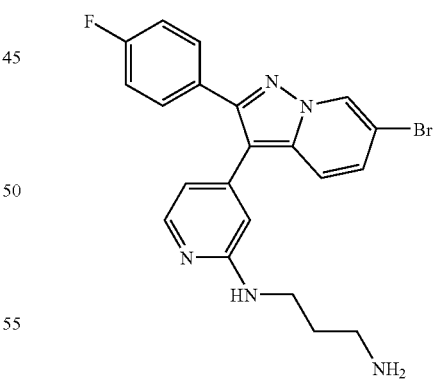

In a similar manner as described in Example 28, using 6-bromo-2-(4-fluorophenyl)-3-(2-fluoro-4-pyridinyl)pyrazolo[1,5-a]pyridine (Example 50) and 1,3-diaminopropane was obtained the title compound. ¹H NMR (d₆-acetone) δ 8.94 (s, 1H), 8.06 (d, 1H, J=4.8 Hz), 7.72 (m, 3H), 7.44 (dd, 1H, J=1.5, 9.6 Hz), 7.23 (m, 3H), 6.51 (s 1H), 6.48 (dd, 1H, J=1.2, 6.3 Hz), 6.08 (m 1H), 3.44 (q, 2H, J=5.7 Hz), 3.31 (t, 2H, J=6.3 Hz), 1.90 (quint, 2H, J=6.8 Hz). MS (ES+ve) 440 (100, M⁺, M+3)

Example 52

6-Cyano-2-(4-fluorophenyl)-3-(4-pyridinyl)pyrazolo[1,5-a]pyridine

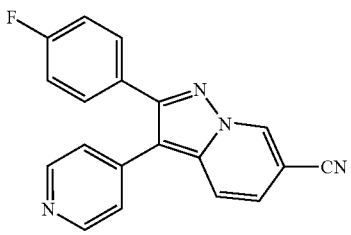

In a similar manner as described in Examples 2a, 2b, 1d, 1e, and 1f, from 3-cyanopyridine was obtained the title compound. $^1$H NMR (CDCl$_3$) δ 8.90 (s, 1H), 8.66 (d, 2H, J=5.9 Hz), 7.66 (d, 1H, J=9.2 Hz), 7.55 (m, 2H), 7.30 (m, 1H), 7.25 (m, 2H), 7.09 (t, 2H, J=8.6 Hz). MS (ES+ve): 315 (5, M+2), 315 (100, M+1).

Example 53

2-(4-Fluorophenyl)-3-(4-pyridinyl)pyrazolo[1,5-a]pyridine-6-carboxamide

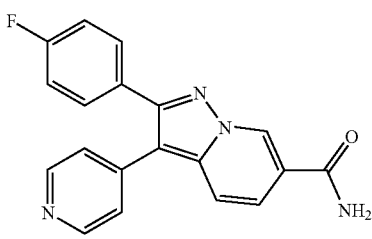

A mixture of 6-cyano-2-(4-fluorophenyl)-3-(4-pyridinyl)pyrazolo[1,5-a]pyridine (Example 52. 100 mg, 0.318 mmol) and concentrated hydrochloric acid (2 mL) were stirred at room temperature overnight. The mixture was diluted with ether, basified with 5N sodium hydroxide solution and extracted thoroughly with ethyl acetate several times. The combined organic layers were dried (MgSO$_4$), filtered and evaporated to dryness. The title compound was isolated in 85% yield (90 mg). $^1$H NMR (d$_6$-DMSO) δ 9.36 (s, 1H), 8.60 (d, 2H, J=5.2 Hz), 8.22 (bs, 1H), 7.81 (bs, 2H), 7.67 (bs, 1H), 7.58 (m, 2H), 7.28–7.37 (m, 4H). MS (ES+ve): 334 (25, M+2), 333 (100, M+1).

Example 54

6-Cyano-2-(4-fluorophenyl)-3-(2-fluoro-4-pyridinyl)pyrazolo[1,5-a]pyridine

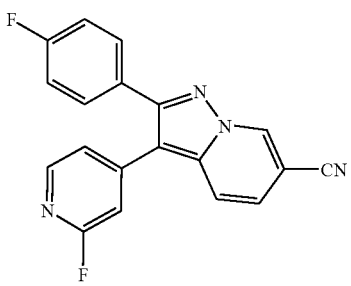

In a similar manner as described in Example 27, from 2-fluoro-4-pyridylboronic acid and 3-bromo-6-cyano-2-(4-fluorophenyl)pyrazolo[1,5-a]pyridine (intermediate from Example 52) was obtained the title compound. $^1$H NMR (CDCl$_3$) δ 8.89 (s, 1H), 8.24 (d, 1H, J=5.3 Hz), 7.66 (d, 1H, J=9.3 Hz), 7.52 (m, 2H), 7.33 (d, 1H, J=9.3 Hz), 7.10 (m, 3H), 6.89 (s, 1H). MS (ES+ve): 334 (10, M+2), 333 (100, M+1).

Example 55

6-Cyano-4-[2-(4-fluorophenyl)-pyrazolo[1,5-a]pyridin-3-yl]-N-cyclopropyl-2-pyridinamine

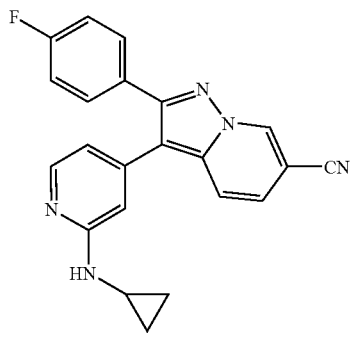

In a similar manner as described in Example 28, from 6-cyano-2-(4-fluorophenyl)-3-(2-fluoro-4-pyridinyl)pyrazolo[1,5-a]pyridine (Example 54) and cyclopropylamine was obtained the title compound. $^1$H NMR (CDCl$_3$) δ 8.88 (s, 1H), 8.11 (m, 1H), 7.55–7.70 (m, 4H), 7.10 (m, 2H), 7.64 (m, 2H), 5.09 (s, 1H), 2.36 (m, 1H), 0.63 (m, 2H), 0.46 (m, 2H). MS (ES−ve): 369 (15, M$^+$), 368 (70, M−1), 228 (100).

Example 56

2-(4-Fluorophenyl)-3-(4-pyrimidinyl)-pyrazolo[1,5-a]pyridine

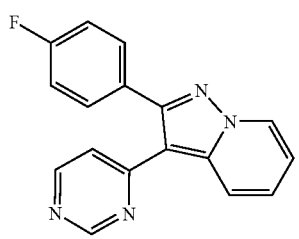

a) 1-(4-fluorophenyl)-2-(4-pyrimidinyl)-ethanone

To a stirred solution of 4-methylpyrimidine (20.64 g, 0.22 mol) and ethyl 4-fluorobenzoate (36.9 g, 0.22 mol) in dry THF (100 mL) at 0° C. under nitrogen was added lithium bis(trimethylsilyl)amide (1M in THF, 440 mL, 0.44 mol) over a 2 h period. A white precipitate deposited during the addition and this suspension was stirred at room temperature overnight. The reaction was diluted with 100 mL of water and filtered. The filtrate was washed with water (3×) and dried. The solution was diluted with ethyl acetate (100 mL) and the organic phase separated. The aqueous phase was further extracted with ethyl acetate (100 mL). Organic phases were dried (MgSO$_4$) and concentrated and combined with the filtrate to give a combined yield of 47 g (98%) of product. $^1$H NMR (CDCl$_3$) exists as a 2:1 mixture of enol:keto tautomers: 6 enol form: 5.95 (s, 1H), 6.92 (dd, J=1.2, 5.7 Hz, 1H), 7.06–7.14 (m, 2H), 7.83 (dd, J=5.4, 8.7 Hz, 2H), 8.40 (d, J=5.7 Hz, 1H), 8.8 (s, 1H); keto form: 4.42

(s, 2H), 7.12–7.18 (m, 2H), 7.34 (d, J=4.2 Hz, 1H), 8.06 (dd, J=5.3, 8.8 Hz, 2H), 8.67 (d, J=5.1 Hz, 1H), 9.16 (s, 1H); APESI-MS m/z 215 (M−1)⁻.

b) 2-(4-Fluorophenyl)-3-(4-pyrimidinyl)-pyrazolo[1,5-a]pyridine

A solution of 1-(4-fluorophenyl)-2-(4-pyrimidinyl)-ethanone (21.6 g, 0.1 mol), 1-aminopyridinium iodide (22.2 g, 0.1 mol) and potassium carbonate (41.4 g, 0.3 mol) in a mixture of water (300 mL) and isopropanol (300 mL) was heated and stirred at 100° C. for 16 h. The isopropanol was removed under vacuum and the resulting aqueous phase extracted with dichloromethane (5×200 mL). The dichloromethane extracts were combined and the solvent evaporated under reduced pressure to leave a red solid which was purified by silica gel chromatography eluting with a hexane/EtOAc to give the title compound as a yellow solid, 9.16 g (32%). $^1$H NMR (d$_6$-DMSO) δ 7.07 (d, J=5.4 Hz, 1H), 7.14 (t, J=6.8 Hz, 1H), 7.32 (t, J=8.7 Hz, 2H), 7.53 (t, J=7.8 Hz, 1H), 7.60 (dd, J=5.7, 8.7 Hz, 2H), 8.40 (d, J=8.9 Hz, 1H), 8.54 (d, J=5.3 Hz, 1H), 8.83 (d, J=7.1 Hz, 1H), 9.16 (s, 1H), APESI+MS m/z 291 (M+1).

Example 57

2-(4-Fluorophenyl)-3-(4-(2-methylthio)pyrimidinyl)pyrazolo[1,5-a]-pyridine

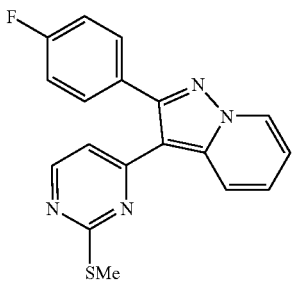

a) 1-(4-Fluorophenyl)-2-(4-(2-methylthio)pyrimidinyl)ethanone

To a stirred solution of 2-methylthio-4-methylpyrimidine (66 g, 0.47 mol) and ethyl 4-fluorobenzoate (79 g, 0.47 mol) in dry THF (400 mL) at 0° C. under nitrogen was added lithium bis(trimethylsilyl)amide (1N in THF, 940 mL, 0.94 mol) over a 2 h period. The solution was stirred at ice bath temperature for 18 h. The solution was poured into 2 L of ice cold 0.5 N HCl. A precipitate formed which was filtered off and air dried. Second and third crops of solids were obtained as the precipitate was washed with water. The combined precipitates were recrystalized from acetone and water to give product as a yellow solid: 117 g (95%0). $^1$H NMR (CDCl$_3$) δ (all in enol form): 3.0 (s, 3H), 6.29 (s, 1H), 7.01 (d, J=5.7 Hz, 1H), 7.48 (t, J=8.7 Hz, 2H), 8.20 (dd, J=5.4, 8.8 Hz, 2H), 8.68 (d, J=5.7 Hz, 1H); APESI-MS m/z 261 (M−1)⁻.

b) 2-(4-Fluorophenyl)-3-(4-(2-!methylthio)pyrimidinyl)-pyrazolo[1,5-a]pyridine

A solution of 1-(4-fluorophenyl)-2-(4-(2-methylthio)pyrimidinyl)ethanone (13.0 g, 50 mmol) in isopropanol (300 mL) was warmed to reflux. A solution of 1-aminopyridinium iodide (14 g, 63 mmol) in water (300 mL) was treated with 2N NaOH (31.5 mL). This solution was added to the ketone over a period of 2 h while the mixture was heated at reflux. After an additional 7 h, the isopropanol was partially evaporated under reduced pressure and the resulting solution was extracted with dichloromethane (2×300 mL). The dichloromethane extracts were combined, dried (MgSO$_4$), filtered and the solvent evaporated under reduced pressure to leave a red solid which was purified by silica gel chromatography with dichloromethane to give the title compound as a yellow solid, 4.5 g (26%). $^1$H NMR (d$_6$-DMSO) δ 2.5 (s, 3H), 6.80 (d, J=5.3 Hz, 1H), 7.18 (t, J=6.9 Hz, 1H), 7.36 (t, J=8.8 Hz, 2H), 7.59 (t, J=7.9 Hz, 1H), 7.60 (dd, J=5.7, 8.7 Hz, 2H), 8.38 (d, J=9.1 Hz, 1H), 8.40 (d, J=5.3 Hz, 1H), 8.88 (d, J=7.0 Hz, 1H), APESI+MS m/z 337 (M+1).

Example 58

2-(4-Fluorophenyl)-3-(4-(2-methylsulfinyl)pyrimidinyl)pyrazolo[1,5-a]-pyridine

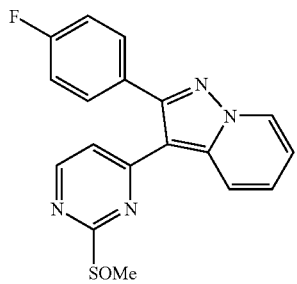

To a stirred solution of 2-(4-fluorophenyl)-3-(4-(2-methylthio)pyrimidinyl)pyrazolo[1,5-a]pyridine (Example 57. 0.285 g, 0.85 mmol) in dichloromethane (10 mL) was added, dropwise, a solution of (0.257 g, 0.85–1.23 mmol) of 57–86% m-chloroperoxybenzoic acid in dichloromethane (5 mL). After 10 min., the solution was quenched by the addition of aqueous potassium carbonate (20 mL), and the organic phase was separated. The aqueous phase was further extracted with dichloromethane (2×20 mL) and the dichloromethane phases dried (MgSO$_4$) and concentrated to give a crude white solid. Chromatography on silica gel eluting with a hexane/EtOAc gradient (0–100% EtOAc) gave the title compound as a white solid, 0.213 g (60: $^1$H NMR (CDCl$_3$) δ 3.05 (s, 3H), 7.07–7.11 (m, 2H), 7.25 (d, J=8.5 Hz, 2H), 7.55 (t, J=7.8 Hz, 1H), 7.64 (dd, J=5.5, 6.9 Hz, 2H), 8.52 (d, J=5.1 Hz, 1H), 8.59 (d, J=6.9 Hz, 1H), 8.84 (d, J=9.0 Hz, 1H); APESI+MS m/z 353 (M+1)⁻.

Example 59

2-(4-Fluorophenyl)-3-(4-(2-methylsulfonyl)pyrimidinyl)pyrazolo[1,5-a]-pyridine

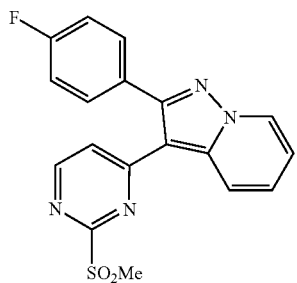

Obtained as a minor product in Example 58. $^1$H NMR (CDCl$_3$) δ 3.42 (s, 3H), 7.11 (t, J=7 Hz, 1H), 7.18 (d, J=5.5 Hz, 1H), 7.26 (t, J=8.6 Hz, 2H) overlapping with CHCl$_3$, 7.58 (t, J=8.0 Hz, 1H), 7.64 (dd, J=5.5, 8.5 Hz, 2H), 8.53 (d, J=5.5 Hz, 1H), 8.60 (d, J=6.8 Hz, 1H), 8.78 (d, J=8.8 Hz, 1H); APESI+MS m/z 369 (M+1)⁻.

Example 60

N-Butyl-4-[2-(4-fluorophenyl)pyrazolo[1,5-a]pyridin-3-yl]-2-pyrimidin-amine

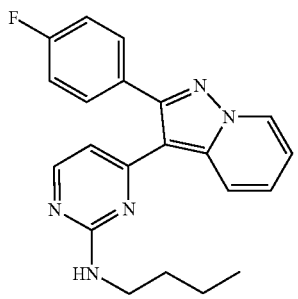

A solution of 2-(4-fluorophenyl)-3-(4-(2-methylsulfinyl)pyrimidinyl)pyrazolo[1,5-a]pyridine (Example 58. 0.03 g, 0.085 mmol) in n-butylamine (0.5 mL) was heated to reflux for 0.25 h. On cooling a white solid deposits which was collected by filtration, washed with hexane and dried under vacuum to give the title compound as a white solid, 0.029 g (94%). ¹H NMR (d₆-DMSO) δ 0.87 (t, J=7.4 Hz, 3H), 1.31 (sextet, J=7.4 Hz, 2H), 1.49(quintet, J=7.2 Hz, 2H), 3.25 (q, J=6.6 Hz, 2H), 6.4 (bs, 1H), 7.06 (t, J=6.8 HZ, 1H), 7.13 (bs, 1H), 7.29 (t, J=8.8 Hz, 2H), 7.43 (t, J=7.8 Hz, 1H), 7.59 (dd, J=5.7, 8.5 Hz, 2H), 8.01 (d, J=5.3 Hz, 1H), 8.40 (bs, 1H), 8.76 (d, J=6.9 Hz, 1H); APESI+MS m/z 362 (M+1)⁻.

Example 61

N-Cyclopropyl-4-[2-(4-fluorophenyl)pyrazolo[1,5-a]pyridin-3-yl]-2-pyrimidinamine

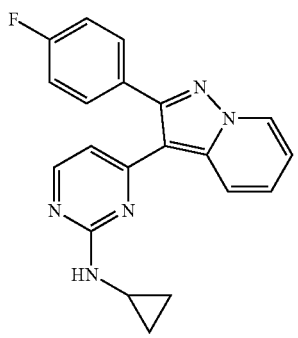

In a similar manner as described for Example 60, from 2-(4-fluorophenyl)-3-(4-2-methylsulfinyl)pyrimidinyl)pyrazolo[1,5-a]pyridine (Example 58. 0.05 g, 0.14 mmol) and cyclopropylamine was obtained the title compound as a white solid, 0.018 g. (60%). ¹H NMR (CDCl₃) δ 0.65–0.70 (m, 2H), δ 0.89–0.95 (m, 2H), δ 2.85–2.92 (m, 1H), 5.47 (bs, 1H), 6.42 (d, J=5.4 Hz, 1H), 6.96 (t, J=6.2 Hz, 1H), 7.19 (t, J=8.6 Hz, 2H), 7.36 (t, J=7.3 Hz, 1H), 7.66 (dd, J=5.4, 8.7 Hz, 2H), 8.12 (d, J=5.4 Hz, 1H), 8.54 (d, J=7.0 Hz, 1H), 8.62 (d, J=9.0 Hz, 1H); APESI+MS m/z 346 (M+1)⁻.

Example 62

N-Benzyl-4-[2-(4-fluorophenyl)pyrazolo[1,5-a]pyridin-3-yl]-2-pyrimidinamine

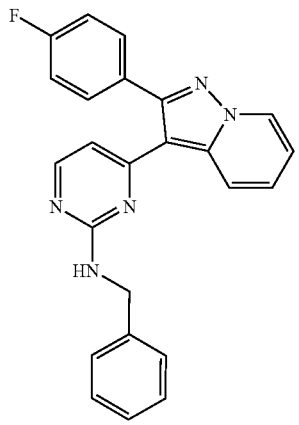

In a similar manner as described for Example 60, from 2-(4-fluorophenyl)-3-(4-(2-methylsulfinyl)pyrimidinyl)pyrazolo[1,5-a]pyridine (Example 58. 0.03 g, 0.085 mmol) and benzylamine was obtained the title compound as a white solid, 0.027 g. (60%). ¹H NMR (d₆-DMSO) δ 4.52 (d, J=6.3 Hz, 2H), 6.17 (d, J=5.2 Hz, 1H), 7.00 (bs, 1H), 7.18–7.34 (m, 9H), 7.54–7.62 (m, 2H), 7.74 (t, J=6.0 Hz, 1H), 8.04 (d, J=5.1 Hz, 1H), 8.72 (d, J=5.8 Hz, 1H); APESI+MS m/z 396 (M+1)⁻

Example 63

4-[2-(4-Fluorophenyl)pyrazolo[1,5-a]pyridin-3-yl-N-(2-propyl)-2-pyrimidinamine

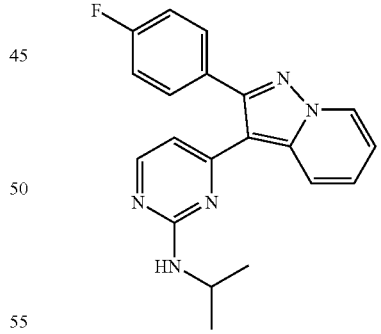

In a similar manner as described for Example 60, from 2-(4-fluorophenyl)-3-(4-(2-methylsulfinyl)pyrimidinyl)pyrazolo[1,5-a]pyridine (Example 58. 0.063 g, 0.18 mmol) and isopropylamine was obtained the title compound as a white solid, 0.022 g (66%). ¹H NMR (CDCl₃) δ 1.28 (d, J=6.6 Hz, 6H), δ 4.21 (septet, J=6.6 Hz, 1H), δ 5.02 (bs, 1H), 6.29 (d, J=5.3 Hz, 1H), 6.89 (t, J=6.4 Hz, 1H), 7.12 (t, J=8.6 Hz, 2H), 7.31 (t, J=7.9 Hz, 1H), 7.60 (dd, J=5.5, 8.6 Hz, 2H), 8.03 (d, J=5.3 Hz, 1H), 8.38 (d, J=8.9 Hz, 1H), 8.48 (d, J=7.0 Hz, 1H); APESI+MS m/z 348 (M+1)⁻.

Example 64

4-[2-(4-Fluorophenyl)pyrazolo[1,5-a]pyridin-3-yl]-2-pyrimidinamine

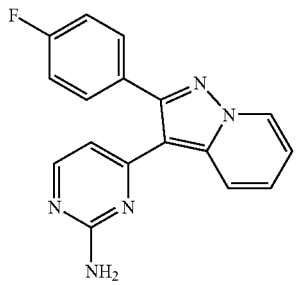

a) 2-(4-Fluorophenyl)-3-acetylpyrazolo[1,5-a]pyridine

A mixture of 2-(4-fluorophenyl)pyrazolo[1,5-a]pyridine (2.00 g, 9.42 mmol) in acetic anhydride (20 mL) and conc. $H_2SO_4$ (2 drops) was stirred and heated at reflux for 30 min. The mixture was cooled to room temperature, poured into ice water (300 mL), and basified (pH=10) using 1N NaOH (aq). The resulting orange precipitate was collected by filtration, washed with water, air-dried, then dried under high-vacuum to afford the title compound as an orange solid, 2.60 g (quant.). $^1$H NMR (CDCl$_3$) δ 8.56 (d, 1H, J=6.9 Hz), 8.45 (d, 1H, J=9.3 Hz), 7.62 (m, 2H), 7.54 (m, 1H), 7.24 (m, 2H), 7.08 (m, 1H), 2.20 (s, 3H): MS (+ve ion electrospray) 255 (100), (MH+).

b) 2-(4-Fluorophenyl)-3-(3-(dimethylamino)-2-propenoyl)pyrazolo[1,5-a]pyridine

A mixture of 2-(4-fluorophenyl)-3-acetylpyrazolo[1,5-a]pyridine (1.0 g, 3.93 mmol) in N,N-dimethylformamide dimethyl acetal (10 mL) was stirred and heated at reflux for 17 h. The mixture was cooled to room temperature and the volatiles evaporated under reduced pressure. The residue was purified by silica gel chromatography (eluded with 1% MeOH/CH$_2$Cl$_2$) to afford the title compound as an orange solid, 0.830 g (68%). $^1$H NMR (CDCl$_3$) 88.50 (d, 1H, J=6.9 Hz), 8.39 (d, 1H, J=9.0 Hz), 7.83 (d, 2H, J=12.6 Hz), 7.73 (m, 2H), 7.39 (m, 1H), 7.20 (m, 2H), 6.93 (m, 1H), 5.13 (d, 1H, J=12.5 Hz), 3.10 (s, 3H), 2.56 (s, 3H). MS (+ve ion electrospray) 310 (90), (MH+).

c) 4-[2-(4-Fluorophenyl)pyrazolo[1,5-a]pyridin-3-yl]-2-pyrimidinamine

A mixture of 2-(4-fluorophenyl)-3-(3-(dimethylamino)-2-propenoyl)pyrazolo[1,5-a]pyridine (60 mg, 0.19 mmol), guanidinium hydrochloride (36 mg, 0.38 mmol), and K$_2$CO$_3$ (105 mg, 0.76 mmol) in N,N-dimethylformamide (3 mL) was stirred in a 110° C. oil bath for 8 h. Additional guanidinium hydrochloride (36 mg, 0.38 mmol) was added, and the mixture stirred in a 110° C. oil bath for 16 h. The mixture was cooled to room temperature, and water (20 mL) added. The resulting tan precipitate was collected by filtration, washed with water, air-dried, the dried under high-vacuum to afford the title compound, 0.033 g (57%). $^1$H NMR (CDCl$_3$) δ 8.57 (d, 1H, J=6.0 Hz), 8.51 (d, 1H, J=8.9 Hz), 7.98 (d, 2H, J=5.7 Hz), 7.64 (m, 2H), 7.46 (m, 1H), 7.22 (m, 2H), 7.04 (m, 1H), 6.47 (d, 1H, J=5.8 Hz), 5.76 (s. 2H). MS (+ve ion electrospray) 306 (100), (MH+).

Example 65

4-[2-(4-Fluorophenyl)-6-trifluoromethylpyrazolo[1,5-a]pyridin-3-yl]-2-pyrimidinamine

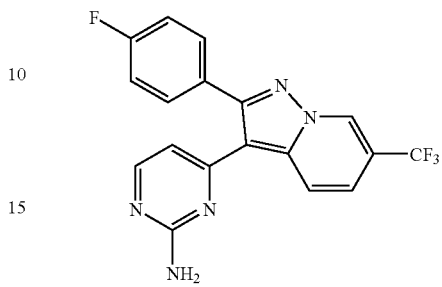

a) 1-(4-Fluorophenyl)-2-(2-(5-trifluoromethyl)pyridyl)ethanone

To a solution of 4-fluoroacetophenone (13.8 g, 0.100 mol) and 2-chloro-5-trifluoromethylpyridine (20.0 g, 0.110 mol) in tetrahydrofuran (400 mL) was added sodium hydride (95%, 5.56 g, 0.220 mol) in several portions. The reaction was stirred at room temperature for 72 h then carefully quenched by the addition of water (300 mL) and diethyl ether (200 mL). The organic layer was separated and extracted with 6N HCl (2×300 mL). The aqueous extracts were cooled to 0° C. and 6N NaOH was used to adjust the solution to pH 12. The mixture was then extracted with diethyl ether and the combined organic extracts were dried (MgSO$_4$). The drying agent was removed by filtration and the filtrate was evaporated to dryness to afford the title compound as a tautomeric mixture, 20.9 g (73%). $^1$H NMR (CDCl$_3$) δ 8.87(s), 8.63(s), 8.14(dd, J=5.1, 8.4 Hz), 8.00–7.83(m), 7.51(d, J=8.4 Hz), 7.22–7.12(m), 6.13(s), 4.60(s). MS (ES+ve): 284 (100, M$^+$+1).

b) 1-(4-Fluorophenyl)-2-(2-(5-trifluoromethyl)pyridyl)ethanone Oxime

To a solution of 1-(4-fluorophenyl)-2-(2-(5-trifluoromethyl)pyridyl)ethanone (80.0 g, 0.282 mol) in methanol (1 L) at room temperature was added 10% aqueous sodium hydroxide (436 mL, 1.09 mol). The resulting solution was stirred vigorously as solid hydroxylamine hydrochloride (98.0 g, 1.40 mol) was added. The mixture was heated to reflux for 2 h, treated with decolorizing charcoal while hot, then filtered through Celite while hot. The filtrate was concentrated to one-half its original volume and then cooled to 0° C. with stirring for 1 h. The resulting solids were collected by filtration, washed with water, and dried under vacuum at 50° C. overnight to provide the title compound as a light yellow powder, 73.9 g (88%). $^1$H NMR (d$_6$-DMSO) δ 11.60(s, 1H), 8.86(s, 1H), 8.14(dd, 1H, J=2.1, 8.1 Hz), 7.78(dd, 2H, J=5.7, 9.0 Hz), 7.53(d, 1H, J=8.4 Hz), 7.23(t, 2H, J=9.0 Hz), 4.40(s, 2H). MS (ES+ve): 299 (70, M$^+$+1).

c) 3-(4-Fluorophenyl)-2-(2-(5-trifluoromethyl)pyridyl)-2H-azirine

To a solution of 1-(4-fluorophenyl)-2-(2-(5-trifluoromethyl)pyridyl)ethanone oxime (25.0 g, 0.084 mol) in methylene chloride (400 mL) was added triethylamine (46.7 mL, 0.335 mol). The solution was cooled to 0° C. under a nitrogen atmosphere, and trifluoroacetic anhydride (140.1 mL, 0.100 mol) was added dropwise. The reaction was stirred for 0.5 h then quenched with water. The organic layer was separated and dried (MgSO$_4$). The drying agent was removed by filtration and the solvent was evaporated from the filtrate to leave an oil. The residue was loaded onto a silica gel column and eluted with 0.15% ethyl acetate in hexanes to give the title compound as an oil which solidified on standing, 19.4 g (82%). $^1$H NMR (CDCl$_3$) δ 8.76(s, 1H), 7.93(dd, 2H, J=5.4, 8.7 Hz), 7.83(dd, 1H, J=2.1, 8.4 Hz), 7.27(t, 2H, J=8.7 Hz), 7.21(d, 1H, J=8.1 Hz), 3.54 (s, 1H). MS (ES+ve): 281 (100, M$^+$+1).

d) 2-(4-Fluorophenyl)-6-trifluoromethylpyrazolo[1,5-a]pyridine 3-(4-Fluorophenyl)-2-(2-(5-trifluoromethyl)pyridyl)-2H-azirine (40.0 g, 0.143 mol) was dissolved in 1,2,4-trichlorobenzene (400 mL) and the mixture was heated to 200° C. for 10 h. The reaction mixture was then cooled to room temperature and poured onto a silica gel column. The column was eluted with hexanes to remove the 1,2,4-trichlorobenzene, and then with 20% diethyl ether in hexanes to elute the product. The desired fractions were combined and the solvent was evaporated under reduced pressure to leave the title compound, 28.7 g (71%). $^1$H NMR (CDCl$_3$) δ 8.84(s, 1H), 7.98(dd, 2H, J=5.4, 8.7 Hz), 7.65(d, 1H, J=9.3 Hz), 7.28(d, 1H, J=9.3 Hz), 7.20(t, 2H, J=8.7 Hz), 6.88(s, 1H). MS (ES+ve): 281 (100, M$^+$+1).

e) 2-(4-Fluorophenyl)-3-acetyl-6-trifluoromethylpyrazolo[1,5-a]pyridine

To a mixture of 2-(4-fluorophenyl)-6-trifluoromethylpyrazolo[1,5-a]pyridine (10.30 g, 36.76 mmol) and acetic anhydride (100 mL) was added conc. sulfuric acid (10 drops) and the mixture was stirred and heated at reflux for 1 h. The reaction mixture was cooled to room temperature and poured into ice water (300 mL). 2N Aqueous sodium hydroxide solution was added to raise the pH of the solution to about 10 and the resulting orange precipitate was collected by filtration. The solid was washed with water, air-dried, and then dried under vacuum to afford the title compound as an orange solid, 11.87 g (quant.). $^1$H NMR (d$_6$-DMSO) δ 9.58 (s, 1H), 8.41 (d, 1H, J=9.3 Hz), 7.89 (d, 1H, J=9.5 Hz), 7.74 (m, 2H), 7.39 (m, 2H), 2.22 (s, 3H). MS (+ve ion electrospray) 323 (70), (MH+).

f) 2-(4-fluorophenyl)-3-(3-(dimethylamino)-2-propenoyl)-6-trifluoromethylpyrazolo[1,5-a]pyridine A mixture of 2-(4-fluorophenyl)-3-acetyl-6-trifluoromethylpyrazolo[1,5-a]pyridine (11.85 g, 36.77 mmol) and N,N-dimethylformamide dimethyl acetal (100 mL) was stirred at reflux for 17 h. The mixture was cooled to room temperature and then to 0° C. The resulting orange precipitate was collected by filtration, washed with cold hexanes, and dried under vacuum to afford the title compound as an orange solid, 10.17 g (73%). $^1$H NMR (d$_6$-DMSO) δ 9.44 (s, 1H), 8.22 (d, 1H, J=9.4 Hz), 7.75 (m, 2H), 7.65 (d, 1H, J=9.5 Hz), 7.56 (d, 1H, J=12.4 Hz), 7.35 (m, 2H), 5.05 (d, 1H, J=12.3 Hz), 3.04 (s, 3H), 2.56 (s, 3H). MS (+ve ion electrospray) 377 (80), (M+).

g) 4-[2-(4-Fluorophenyl)-6-trifluoromethylpyrazolo[1,5-a]pyridin-3-yl]-2-pyrimidinamine A mixture of 2-(4-fluorophenyl)-3-(3-(dimethylamino)-2-propenoyl)-6-trifluoromethylpyrazolo[1,5-a]pyridine (100 mg, 0.27 mmol), guanidinium hydrochloride (52 mg, 0.54 mmol), and sodium ethoxide (73 mg, 1.08 mmol) in EtOH (4 mL) was stirred at reflux for 21 h. Additional guanidine was added in portions to the mixture until starting material was consumed as evidenced by TLC. The reaction mixture was cooled to 0° C. and the resulting precipitate was collected by filtration washed with cold EtOH and dried under vacuum to afford the title compound as a tan solid, 93 mg (92%). $^1$H NMR (acetone-d$_6$) δ 9.19 (s, 1H), 8.73 (d, 1H, J=9.4 Hz), 8.13 (d, 1H, J=5.2 Hz), 7.78 (m, 2H), 7.63 (d, 1H, J=9.5 Hz), 7.34 (m, 2H), 6.41 (d, 1H, J=5.2 Hz), 6.17 (s, 1H). MS (+ve ion electrospray) 374 (100), (MH+).

Example 66

N-Butyl-4-[2-(4-fluorophenyl)-6-trifluoromethylpyrazolo[1,5-a]pyridin-3-yl]-2-pyrimidinamine

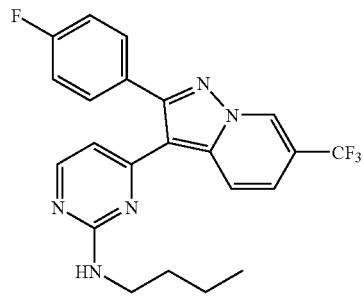

In a similar manner as described for Example 65g, using N-butylguanidine in place of guanidinium hydrochloride was obtained the title compound as a yellow solid, (37%). $^1$H NMR (acetone-d$_6$) δ 9.14 (s, 1H), 8.63 (d, 1H, J=9.3 Hz), 8.09 (d, 1H, J=5.1 Hz), 7.72 (m, 2H), 7.59 (d, 1H, 19.3 Hz), 7.27 (m, 2H), 6.40 (s, 1H), 6.33 (d, 1H, J=4.2 Hz), 3.44 (m, 2H), 1.62 (m, 2H), 1.42 (m, 2H), 0.93 (m, 3H). MS (+ve ion electrospray) 430 (95), (MH+).

Example 67

N-Benzyl-4-[2-(4-fluorophenyl)-6-trifluoromethylpyrazolo[1,5-a]pyridin-3-yl]-2-pyrimidinamine

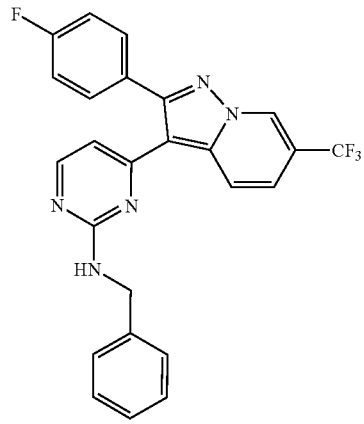

In a similar manner as described for Example 65g, using N-benzylguanidine in place of guanidinium hydrochloride was obtained the title compound as a tan solid, (quant.). $^1$H NMR (acetone-d$_6$) δ 9.09 (s, 1H), 8.12 (d, 1H, J=5.1 Hz), 7.69 (m, 2H), 7.24–7.42 (m, 7H), 7.01 (m, 1H), 6.34 (d, 1H, J=5.1 Hz), 4.70 (d, 2H, J=6.2 Hz). MS (+ve ion electrospray) 464 (95), (MH+).

Example 68

N-Cyclopropyl-4-[2-(4-fluorophenyl)-6-trifluoromethylpyrazolo[1,5-a]pyridin-3-yl]-2-pyrimidinamine

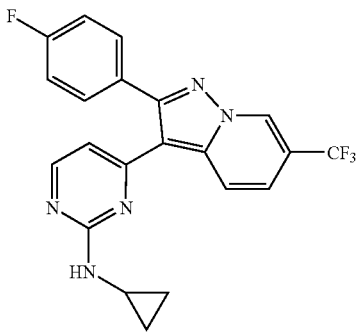

In a similar manner as described for Example 65g, using N-cyclopropylguanidine in place of guanidinium hydrochloride was obtained the title compound as an off-white solid, (77%). $^1$H NMR (acetone-$d_6$) δ 9.14 (s, 1H), 8.88 (s, 1H), 8.11 (d, 1H, J=5.0 Hz), 7.73 (m, 2H), 7.62 (d, 1H, J=9.4 Hz), 7.30 (m, 2H), 6.62 (s, 1H), 6.37 (s, 1H, J=5.1 Hz), 2.87 (m, 1H), 0.80 (m, 2H), 0.60 (m, 2H). MS (+ve ion electrospray) 414 (100), (MH+).

Example 69

4-[2-(4-Fluorophenyl)-6-trifluoromethylpyrazolo[1,5-a]pyridin-3-yl]-N-(2-propyl)-2-pyrimidinamine

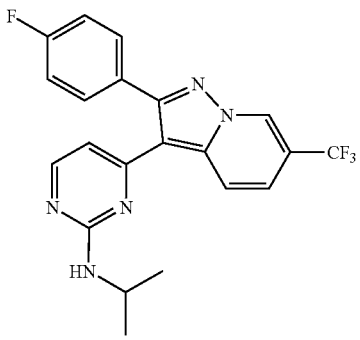

In a similar manner as described for Example 65g, using N-isopropylguanidine in place of guanidinium hydrochloride was obtained the title compound as a white solid, (40%). $^1$H NMR (acetone-$d_6$) δ 9.19 (s, 1H), 8.69 (d, 1H, J=9.5 Hz), 8.15 (d, 1H, J=5.2 Hz), 7.76 (m, 2H), 7.65 (d, 1H, J=9.5 Hz), 7.35 (m, 2H), 6.38 (d, 1H, J=5.2 Hz), 6.25 (s, 1H), 4.27 (m, 1H), 1.31 (d, 6H, J=6.6 Hz). MS (+ve ion electrospray) 416 (100), (M+).

Example 70

4-[2-(4-Fluorophenyl)-6-trifluoromethylpyrazolo[1,5-a]pyridin-3-yl]-N-(2-propenyl)-2-pyrimidinamine

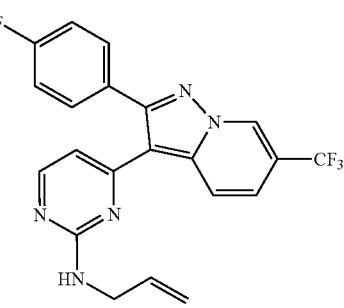

In a similar manner as described for Example 65g, using N-(2-propenyl)guanidine in place of guanidinium hydrochloride was obtained the title compound as a white solid, (49%). $^1$H NMR (acetone-$d_6$) δ 9.14 (s, 1H), 8.66 (d, 1H, J=9.1 Hz), 8.11 (d, 1H, J=5.2 Hz), 7.72 (m, 2H), 7.59 (d, 1H, J=9.3 Hz), 7.28 (m, 2H), 6.56 (s, 1H), 6.36 (d, 1H, J=5.1 Hz), 6.03 (m, 1H), 5.27 (dd, 1H, J=18.9 Hz), 5.09 (d, 1H, J=10.4 Hz), 4.09 (m, 1H). MS (+ve ion electrospray) 414 (100), (MH+).

Example 71

4-[2-(4-Fluorophenyl)-6-trifluoromethylpyrazolo[1,5-a]pyridin-3-yl]-N-(2,2,2-trifluoroethyl)-2-pyrimidinamine

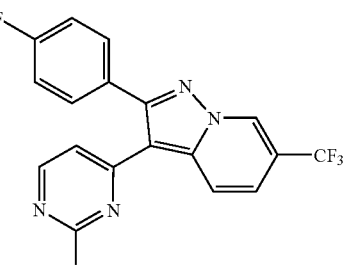

In a similar manner as described for Example 65g, using N-(2,2,2-trifluoroethyl)guanidine in place of guanidinium hydrochloride was obtained the title compound as a white solid, (24%). $^1$H NMR (acetone-$d_6$) δ 9.16 (s, 1H), 8.62 (s, 1H), 8.19 (d, 1H, J=5.0 Hz), 7.71 (m, 2H), 7.61 (d, 1H, J=9.3 Hz), 7.28 (m, 2H), 7.03 (s, 1H), 6.51 (d, 1H, J=4.0 Hz), 4.28 (m, 2H). MS (+ve ion electrospray) 456 (100), (MH+).

Example 72

3-(4-[2-(4-Fluorophenyl)-6-trifluoromethylpyrazolo[1,5-a]pyridin-3-yl]-2-pyrimidinylamino)-1-propanol

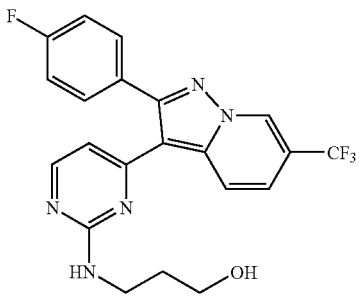

a) 4-[2-(4-Fluorophenyl)-6-trifluoromethylpyrazolo[1,5-a]pyridin-3-yl]-N-(3-(4-methoxybenzyloxy)propyl)-2-pyrimidinamine A mixture of 2-(4-fluorophenyl)-3-(3-(dimethylamino)-2-propenoyl)-6-trifluoromethyl-pyrazolo[1,5-a]pyridine (Example 65f. 2.0 g, 5.3 mmol), N-(3-(4-methoxybenzyloxy)propyl)-guanidine (2.7 g, 7.95 mmol), and potassium carbonate (2.2 g, 15.9 mmol) was stirred in N,N-dimethylformamide (20 mL) in a 100° C. oil bath for 18 h. The mixture was cooled to room temperature, water (200 mL) was added the mixture was extracted with chloroform. The chloroform extracts were dried over anhydrous MgSO$_4$, filtered, and the solvent was evaporated. The crude material was purified by chromatography on silica gel using 30% EtOAc/hexanes as eluent to afford the title compound as a white solid, 2.1 g (72%). $^1$H NMR (acetone-d$_6$) δ 9.18 (s, 1H), 8.67 (d, 1H, J=9.4 Hz), 8.15 (d, 1H, J=5.1 Hz), 7.77 (m, 2H), 7.56 (d, 1H, J=9.2 Hz), 7.34 (m, 4H), 6.90 (d, 2H, J=8.6 Hz), 6.50 (s, 1H), 6.38 (d, 1H, J=5.1 Hz), 4.49 (s, 2H), 3.80 (s, 3H), 3.63 (m, 4H), 1.98 (m, 2H). MS (+ve ion electrospray) 551 (30), (M+).

b) 3-(4-[2-(4-Fluorophenyl)-6-trifluoromethylpyrazolo[1,5-a]pyridin-3-yl]-2-pyrimidinylamino)-1-propanol A solution of 4-[2-(4-fluorophenyl)-6-trifluoromethylpyrazolo[1,5-a]pyridin-3-yl]-N-(3-(4-methoxybenzyloxy)propyl)-2-pyrimidinamine (2.1 g, 3.8 mmol) in 4N HCl/dioxane (5 mL) was stirred at room temperature for 4.5 h, then heated to reflux for 1 h. The mixture was cooled to room temperature, neutralized with saturated aqueous NaHCO$_3$, and extracted with EtOAc. The EtOAc extracts were dried (MgSO$_4$), filtered, and the solvent was evaporated. The residue was triturated with 2% EtOAc/hexanes to afford a solid which was collected by filtration and dried to give the title compound as a white solid, 1.31 g (80% yield). $^1$H NMR (acetone-d$_6$) δ 9.20 (s, 1H), 8.73 (d, 1H, J=9.3 Hz), 8.15 (d, 1H, J=5.1 Hz), 7.77 (m, 2H), 7.64 (d, 1H, J=9.9 Hz), 7.34 (m, 2H), 6.50 (s, 1H), 6.40 (d, 1H, J=5.1 Hz), 3.60–3.70 (m, 4H), 1.88 (m, 2H). MS (+ve ion electrospray) 432 (95), (MH+).

Example 73

N-Cyclopropyl-4-[6-cyano-2-(4-fluorophenyl)pyrazolo[1,5-a]pyridin-3-yl]-2-pyrimidinamine

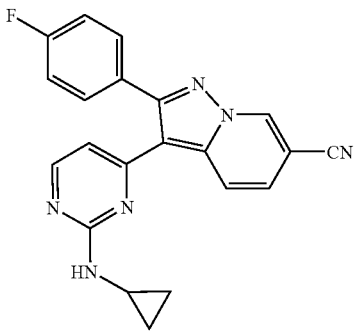

a) 2-(2-(5-Cyanopyridyl))-1-(4-fluorophenyl)ethanone

To a cooled solution (0° C.) of 6-methylnicotinonitrile (5.0 g, 42 mmol) and ethyl 4-fluorobenzoate (6.2 mL, 42 mmol) in anhydrous tetrahydrofuran (50 mL) under N$_2$ was added lithium bis(trimethylsilyl)amide (1.0M solution in tetrahydrofuran. 84 mL, 84 mmol). The reaction mixture was warmed to room temperature and was allowed to stir at room temperature for 18 h The solvents were evaporated under reduced pressure and the residue was triturated with ether and water. The resulting solid was collected by filtration and dried in vacuo to give the title compound as a yellow solid, 10.2 g (quant.). $^1$H NMR (d$_6$-DMSO) showed a mixture of tautomers.

b) 2-(4-Fluorophenyl)-6-cyanopyrazolo[1,5-a]pyridine

N-Boc-O-mesitylsulfonylhydroxylamine (26.7 g, 84.5 mmol) was added in portions to trifluoroacetic acid at 0° C. The mixture was stirred at 0° C. for 30 min and then poured into ice water. The resulting white precipitate was collected by filtration, washed with cold water, and dissolved in dichloromethane (300 mL). The organic solution was dried (MgSO$_4$). The drying agent was removed by filtration and the filtrate was transferred to a flask. To this solution was added 2-(2-(5-cyanopyridyl))-1-(4-fluorophenyl)ethanone (6.77 g, 28.2 mmol) and the reaction mixture was stirred at room temperature for about 24 h. The reaction mixture was washed with water, dried (MgSO$_4$), filtered through a short pad of silica gel and the solvent evaporated under reduce pressure. The residue was purified using chromatography to give the title compound as a brown solid, 2.6 g (39%). $^1$H NMR (CDCl$_3$) δ 6.90 (s, 1H), 7.15, (m, 3H), 7.57 (d, 1H, J=8.0 Hz), 7.93 (dd, 2H, J=5.2, 8.4 Hz), 8.82 (s, 1H).

c) 2-(4-Fluorophenyl)-3-acetyl-6-cyanopyrazolo[1,5-a]pyridine

A solution of 2-(4-fluorophenyl)-6-cyanopyrazolo[1,5-a]pyridine (6.7 g, 11 mmol) and concentrated sulfuric acid (2 drops) in acetic anhydride (25 mL) was heated, and stirred, at 120° C. under N$_2$ for 5 h. The solution was cooled to room temperature, diluted with ice water and basified to pH 11 using 2 N aqueous sodium hydroxide. The solution was extracted with chloroform (3×), and the combined organic extracts were dried and the solvent was evaporated in vacuo. Trituration with methanol afforded a light brown solid which was collected and dried to give the title compound, 1.6 g (84%). $^1$H NMR (d$_6$-DMSO) δ 2.19 (s, 3H), 7.35 (t, 2H, J=8.0 Hz), 7.69 (dd, 2H, J=4.0, 8.0 Hz), 7.86 (dd, 1H, J=4.0, 16 Hz), 8.30 (d, 1H, J=12 Hz), 9.75 (s, 1H). MS (ES+) m/z 280 (M⁺+H).

d) 2-(4-Fluorophenyl)-3-(3-(dimethylamino)-2-propenoyl)-6-cyanopyrazolo[1,5-a]pyridine A mixture of 2-(4-fluorophenyl)-3-acetyl-6-cyanopyrazolo[1,5-a]pyridine (1.6 g, 5.6 mmol) and dimethylformamide-dimethylacetal (15 mL) was stirred and heated at 130° C., under N₂, overnight. The solution was cooled and the resulting solid was collected by filtration and rinsed with acetone. The filtrate was evaporated and the resulting solid was purified using chromatography. The product solids were combined to afford the title compound as a brown solid, 1.3 g (68%). ¹H NMR (d₆-DMSO) showed a mixture of isomers. MS (ES+) m/z 335 (M⁺+H), 264 (M⁺−70).

e) N-Cyclopropyl-4-[6-cyano-2-(4-fluorophenyl)pyrazolo[1,5-a]pyridin-3-yl]-2-pyrimidinamine To a solution of 2-(4-fluorophenyl)-3-(3-(dimethylamino)-2-propenoyl)-6-cyanopyrazolo[1,5-a]pyridine (1.3 g, 3.9 mmol) in dimethylformamide (20 mL), under N₂, was added N-cyclopropylguanidine (0.78 g, 7.8 mmol) and potassium carbonate (1.1 g, 7.8 mmol). The mixture was stirred and heated at 100° C. for 17 h and then additional N-cyclopropyl-guanidine (0.39 g, 3.9 mmol) and potassium carbonate (0.55 g, 3.9 mmol) were added. The mixture was heated at 100° C. for an additional 4 h and then the reaction mixture was cooled and water added. The resulting solid was collected by filtration. This solid was dissolved in diethyl ether and purified using chromatography to give the title compound as a yellow solid, 0.39 g (28%). ¹H NMR (d₆-DMSO) δ 0.50 (m, 2H), 0.69 (d, 2H, J=4.0 Hz), 2.69 (m, 1H), 6.29 (d, 1H, J=8.0 Hz), 7.34 (t, 2H, J=8.0 Hz), 7.47 (d, 1H, J=4.0 Hz), 7.69 (m, 3H), 8.11 (d, 1H, J=4.0 Hz), 8.56 (br 5,1H) MS (ES+) m/z 370 (M⁺+H).

Example 74

N-Cyclopropyl-4-[6-chloro-2-(4-fluorophenyl)pyrazolo[1,5-a]pyridin-3-yl]-2-pyrimidinamine

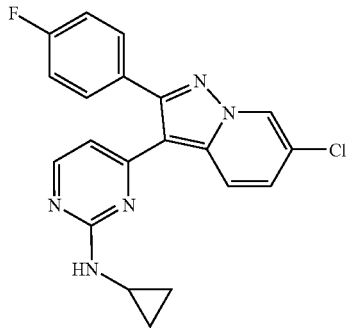

a) 2-(2-(5-chloropyridyl))-1-(4-fluorophenyl)ethanone

In a similar manner as described in Example 65a. From 4-fluoroacetophenone and 2,5-dichloropyridine was obtained the title compound. ¹H NMR (d₆-DMSO) showed a mixture of tautomers. MS (ES+) m/z 250 (M⁺+H), 216 (M⁺−33).

b) 2-(2-(5-Chloropyridyl))-1-(4-fluorophenyl)ethanone Oxime

In a similar manner as described in Example 65b. From 2-(2-(5-chloropyridyl))-1-(4-fluorophenyl)ethanone and hydroxylamine hydrochloride was obtained the title compound. ¹H NMR (d₆-DMSO) δ 4.28 (s, 2H), 7.21 (t, 2H, J=9.0 Hz), 7.33 (d, 1H, 8.4 Hz), 7.76 (dd, 2H, J=5.7, 9.0 Hz), 7.84 (dd, 1H, J=2.7, 8.4 Hz), 8.50 (d, 1H, J=2.4 Hz), 11.55 (s, 1H). MS (ES+) m/z 265 (M⁺+H), 247 (M⁺−17).

c) 3-(2-(5-Chloropyridyl))-2-(4-fluorophenyl)azirine

In a similar manner as described in Example 65c. From 2-(2-(5-chloropyridyl))-1-(4-fluorophenyl)ethanone oxime was obtained the title compound. ¹H NMR (d₆-DMSO) δ 3.49 (s, 1H), 7.36, (d, 1H, J=8.4 Hz), 7.47 (t, 2H, J=8.8 Hz), 7.83 (dd, 1H, J=2.4, 8.4 Hz), 7.96 (dd, 2H, J=5.6, 8.8 Hz), 8.43 (d, 1H, J=2.4 Hz).

d) 2-(4-Fluorophenyl)-6-chloropyrazolo[1,5-a]pyridine

In a similar manner as described in Example 65d. From 3-(2-(5-chloropyridyl))-2-(4-fluorophenyl)azirine was obtained the title compound. ¹H NMR (CDCl₃) δ 6.80 (s, 1H), 7.15, (m, 3H), 7.50 (d, 1H, J=9.3 Hz), 7.95 (dd, 2H, J=5.4, 8.7 Hz), 8.54 (s, 1H). MS (ES+) m/z 247 (M⁺+H), 248 (M⁺+2).

e) N-Cyclopropyl-4-[6-chloro-2-(4-fluorophenyl)pyrazolo[1,5-a]pyridin-3-yl]-2-pyrimidinamine In a similar manner as described in Example 65e and f and 73e. From 2-(4-fluorophenyl)-6-chloropyrazolo[1,5-a]pyridine was obtained the title compound.

Example 75

2-(4-Fluorophenyl)-3-(4-(2-cyclopropylamino)pyrimidinyl)-6-pyrazolo-[1,5-a]pyridinylcarboxamide

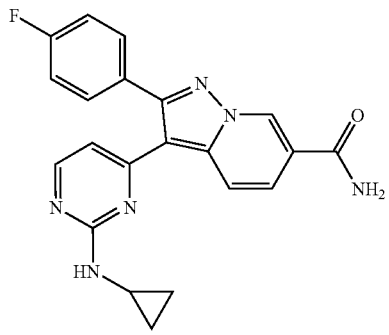

To a solution of sodium methoxide (11.7 g, 0.217 mol) in methanol (100 mL) was added N-cyclopropyl-4-[2-(4-fluorophenyl)-6-trifluoromethylpyrazolo[1,5-a]pyridin-3-yl]-2-pyrimidinamine (Example 68. 3.0 g, 7.26 mmol) and the mixture was heated to reflux and stirred for 24 h. The reaction was cooled to room temperature and sat. aq. NH₄Cl sol was added. The resulting orange solid was collected by filtration and dried in air to give a trimethylorthoformate product, 3.25 g (99%). This orthoformate was added to a mixture of acetone (100 mL) and water (10 mL) and p-toluenesulfonic acid was added. This mixture was heated to about 40° C. for 2 h. The solution was cooled to room temperature and the solvent was evaporated under reduced pressure and the residue was partitioned between water (150 mL) and ethyl acetate (150 mL). The organic phase was separated and dried (MgSO₄). The drying agent was removed and the solvent was evaporated to leave an ester as an orange powder, 2.5 g (86%). A suspension of this ester (1.3 g, 3.23 mmol) in a saturated solution of ammonia in methanol (40 mL) was place in a sealed tube and the tube was heated at about 100° C. for 24 h. The reaction mixture was cooled to room temperature and the resulting precipitate was collected by filtration and dried to give the title compound as an off white solid, 1.17 g (95%). $^1$H NMR (d$_6$-DMSO) δ 9.33 (s, 1H), 8.63 (d, 1H, J=8.3 Hz), 8.22 (s, 1H), 8.12 (d, 1H, J=4.8 Hz), 7.90 (d, 1H, J=9.2 Hz), 7.69 (m, 3H), 7.4 (m, 3H), 6.27 (d, 1H, J=4.9 Hz), 2.76 (m, 1H), 0.73 (d, 2H, J=4.4 Hz), 0.54 (d, 2H, J=3.3 Hz). MS (ES+ve): 389 (95%, MH$^{3o}$).

Example 76

2-(4-Fluorophenyl)-3-(4-(2-(3-hydroxypropyl)amino)pyrimidinyl)-6-pyrazolo-[1,5-a]pyridinylcarboxamide

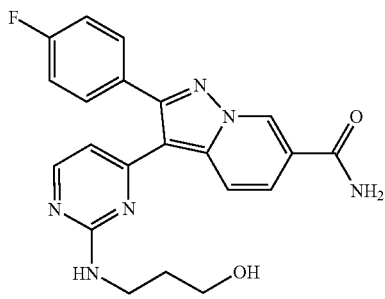

A solution of N-(3-hydroxypropyl)guanidine (5.4 mmol) (prepared from O-methylisourea-hydrochloride (0.597 g, 5.4 mmol) and propanolamine (0.405 g, 5.4 mmol)) in ethanol (15 mL) was added to a solution of sodium ethoxide (20 mmol) in ethanol (40 mL). To this mixture was added the enamine described in Example 65f (1.88 g, 5.0 mmol) and the reaction mixture was heated at reflux for 24 h. The solvent was evaporated under reduced pressure and the residue was partitioned between saturated ammonium chloride solution and 2:1 ethyl acetate:diethyl ether. The organic phase was dried (MgSO$_4$), filtered to remove the drying agent and the solvents were evaporated. The resulting oil was purified by silica gel chromatography using 90% ethyl acetate in hexanes as eluent to give a pyrimidine orthoester compound 1.70 g (3.3 mmol). The orthoester described above (1.73 g, 3.40 mmol) was dissolved in acetone (200 mL) containing water (5 mL). To this solution was added p-TSA monohydrate (0.645 g, 3.40 mmol) and the reaction was stirred at room temperature for 30 min. The acetone was removed under reduced pressure and the residue was dissolved in a tetrahydrofuran:ethyl ether mixture (3:1). The organic phase was washed with saturated sodium bicarbonate solution. The organic layer was dried (MgSO$_4$), filtered and concentrated to dryness. The residue was triturated with diethyl ether and the solids were collected by filtration to afford an ethyl ester, 0.965 g (2.20 mmol) as a white solid. A mixture of the ester described above (1.46 g, 2.98 mmol), sodium cyanide (15 mg, 0.30 mmol) and ammonia in methanol (30 mL, 7M solution) was stirred at room temperature for 5 days. Water (20 mL) was added and the mixture was stirred in an ice-water bath for 30 min. The resulting solid was collected by filtration and dried under vacuum. The solids were then triturated with tetrahydrofuran at 50° C. for 10 min, collected by filtration and dried under vacuum to afford the title compound, 0.935 g (2.30 mmol, 77% yield) as a white powder. $^1$H NMR (d$_6$-DMSO, 80° C.): δ 9.30 (s, 1H), 8.44 (d, 1H, J=9.3 Hz), 8.11 (d, 1H, J=5.1 Hz), 7.87 (d, 1H, J=9.3 Hz), 7.6–7.75 (m, 3H), 7.32 (t, 2H, J=9 Hz), 6.85 (br t, 1H), 6.30 (d, 1H, J=5.1 Hz), 4.25 (br t, 1H), 3.56 (br q, 2H), 3.43 (q, 2H, J=6.3 Hz), 1.77(pent, 2H, J=6.3 Hz). Mass (ES+)=407 (100%).

Example 77

2-(4-Fluorophenyl)-3-(4-(2-methylthio)pyrimidinyl)-6-trifluoromethylpyrazolo-[1,5-a]pyridine

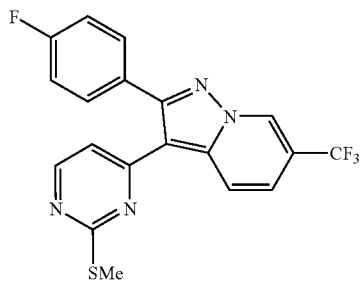

A solution of 2-(4-fluorophenyl)-3-bromo-6-trifluoromethylpyrazolo[1,5-a]pyridine (0.5 g, 1.4 mmoles) in dry dioxane (5 mL) was treated with 2-methylthio-4-tri(n-butyl)stannylpyrimidine (0.58 g, 1.54 mmoles), silver (II) oxide (0.3 g, 1.54 mmoles) and palladium bis acetonitrile dichloride (0.098 mg, 0.14 mmoles). The mixture was heated at 100° C. for 18 h before being allowed to cool to room temperature and filtered through celite. Solvent was evaporated under reduced pressure and the residue purified using silica gel chromatography with 4% ethyl acetate in hexanes to give 2-(4-fluorophenyl)-3-(4-(2-methylthio)-pyrimidinyl)-6-trifluoromethylpyrazolo[1,5-a]pyridine (0.23 g, 0.57 mmoles). $^1$H NMR (CDCl$_3$) δ 8.85 (bd, 1H), 8.55 (d, 1H, J=9.5 Hz), 8.30 (d, 1H, J=5.5 Hz), 7.60 (dd, 2H, J=9,5.3 Hz), 7.50(dd, 1H, J=10,1.5 Hz), 7.18 (dd, 2H, J=9,9 Hz), 6.72 (d, 1H, J=5.3 Hz), 2.75 (s, 3H). MS (+ve electrospray) 405 (100), (MH$^+$).

Example 78

2-(4-Fluorophenyl)-3-(4-(2-methylsulfonyl)pyrimidinyl)-6-trifluoromethylpyrazolo-[1,5-a]pyridine

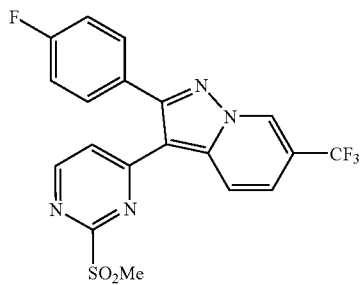

2-(4-Fluorophenyl)-3-(4-(2-methylthio)-pyrimidinyl)-6-trifluoromethylpyrazolo[1,5-a]pyridine (Example 77. 0.23 g, 0.57 mmoles) was dissolved in methanol (80 mL). Oxone (2.53 g) in water (40 mL) was added. The resulting mixture was stirred at room temperature for 2 h. Water (400 mL) was added and the resulting fine suspension filtered and washed with water to afford the title compound as a white solid (0.246 g, 0.56 mmoles). $^1$H NMR (CDCl$_3$) δ 8.88 (bd, 1H), 8.85 (d, 1H. J=9.5 Hz), 8.55 (d, 1H, J=5.5 Hz), 7.65 (dd, 1H, J=9,1.5 Hz), 7.58(dd, 2H, J=5, 9 Hz), 7.24 (dd, 2H, J=9, 9 Hz), 7.19 (d, 1H, J=5.3 Hz), 3.40 (s, 3H).

Example 79

2-(4-Fluorophenyl)-3-(4-(2-(3-(4-methylpiperazino)propyl)amino)pyrimidinyl)-6-pyrazolo-[1,5-a]pyridinylcarboxamide

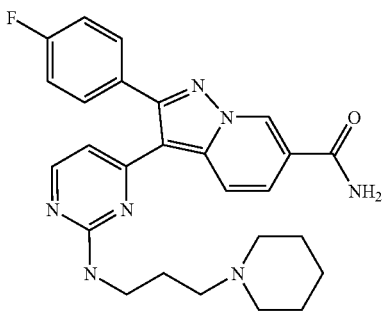

a) N-(3-(4-Methylpiperazino)propyl)-4-[2-(4-fluorophenyl)-6-trifluoromthylpyrazolo[1,5-a]pyridin-3-yl]-2-pyrimidinamine To a mixture of the enamine described in Example 65f (5.45 g, 14.45 mmol) and N-(3-(4-methylpiprazino)propyl) guanidine hydrogen sulfate (12.88 g, 3.0 equiv, 43.4 mmol) in anhydrous DMF (50 mL) under nitrogen was added powdered $K_2CO_3$ (2.75 g, 5.0 equiv, 20.0 mmol). The mixture was stirred and heated at 130° C. for 37 h and then filtered through a glass fritted funnel while warm. The solvent was evaporated under reduced pressure and the residue was triturated with EtOAc/Hexanes (1:10) to afford a solid that was collected by filtration and dried under vacuum to give the desired product as an off-white solid, 5.0 g (67%). $^1$H NMR (CDCl$_3$) δ 1.85 (m, 2H), 2.30 (s, 3H), 2.53 (m, 10H), 3.54 (m, 2H), 6.00 (br s, 1H), 6.30 (d, 1H), 7.14 (m, 2H), 7.40 (d, 1H), 7.60 (m, 2H), 8.08 (d, 1H), 8.49 (d, 1H), 8.81 (s, 1H). MS (ESI$^+$) m/z 514.19 (M$^+$+H).

b) 2-(4-Fluorophenyl)-3-(4-(2-(3-(4-methylpiperazino)propyl)amino)pyrimidinyl)-6-pyrazolo-[1,5-a]pyridinylcarboxamide N-(3-(4-Methylpiperazino)propyl)-4-[2-(4-fluorophenyl)-6-trifluoromethylpyrazolo[1,5-a]pyridin-3-yl]-2-pyrimidinamine (3.08 g, 1.0 equiv, 5.85 mmol) was added to a solution of sodium methoxide in methanol, prepared by dissolving sodium metal (2.69 g, 20 equiv, 117 mmol) in anhydrous methanol (80 mL). The mixture was stirred and heated at reflux for 8 h and then the reaction was allowed to cool to room temperature. The mixture was concentrated in vacuo to half-volume and then water (50 mL) and EtOAc (100 mL) were added. The organic phase was separated and the solvent was evaporated to give an orthoester. This orthoester was dissolved in acetone (40 mL) and water (5 mL). p-Toluenesulfonic acid monohydrate (1.64 g, 1.5 equiv, 8.64 mmol) was added and the mixture was stirred at 80° C. for about 18 h. The reaction was allowed to cool to room temperature and diluted with EtOAc (300 mL). The resulting solution was washed with brine (100 mL) and saturated sodium bicarbonate (2×100 mL) and then dried over (MgSO$_4$). The drying agent was removed and the solvent was evaporated to leave an oil that was triturated with EtOAc/Hexanes (1:10) to give a methyl ester, 3.0 g (99%) as a brown solid. The methyl ester (2.0 g, 1.0 equiv, 4.0 mmol) was suspended in methanolic ammonia (10 mL, 2.0 M). Ammonia gas was bubbled through the suspension until the solution was saturated. The flask was sealed and then heated at 105° C. for 17 h (Caution, pressure). The tube was cooled before being opened. The solvents were evaporated and the solids were triturated with diethyl ether to give the title compound as an off-white solid, 1.2 g (60%). $^1$H NMR (CD$_3$OD) δ 1.87 (m, 2H), 2.37 (s, 3H), 3.35 (m, 8H), 3.50 (m, 4H), 6.38 (d, 1H), 7.29 (m, 2H), 7.67 (m, 2H), 7.88 (d, 1H), 8.08 (d, 1H), 8.47 (d, 1H), 9.22 (s, 1H). MS (ESI$^+$) m/z 489.23 (M$^+$+H).

Example 80

4-[2-(4-Fluorophenyl)pyrazolo[1,5-a]pyridin-3-yl]-N-[2-(1H-imidazol-5-yl)ethyl]-2-pyrimidinamine

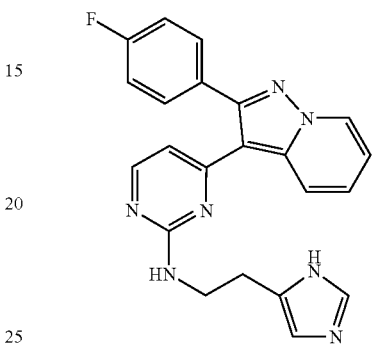

A solution of 2-(4-fluorophenyl)-3-(4-(2-methylsulfinyl)pyrimidinyl)pyrazolo[1,5-a]pyridine (Example 58. 0.105 g, 0.31 mmol) and histamine (0.037 g, 0.33 mmol) in xylene (3 mL) was heated at 135° C. for 3 h. The solvent was evaporated and the residue was purified on silica using methanol/ethyl acetate as eluent to give the title compound as a white solid, 0.044 g (33%).2. $^1$H NMR (d$_6$-DMSO) δ 2.76 (t, J=7.1 Hz, 2H), 3.49 (d, J=6.9 Hz, 2H), 6.17 (d, J=4.4 Hz, 1H), 6.8 (bs, 1H), 7.06 (t, J=6.8 Hz, 1H), 7.17 (bs, 1H), 7.29 (t, J=8.8 Hz, 2H), 7.41 (t, J=7.9 Hz, 1H), 7.51 (s, 1H), 7.60 (dd, J=5.6, 8.6 Hz, 2H), 8.03 (d, J=5.1 Hz, 1H), 8.45 (bs, 1H), 8.76 (d, J=6.9 Hz, $_1$H), 11.8 (bs, 1H); APESI+MS m/z 400 (M+1)$^-$.

Example 81

4-[2-(4-Fluorophenyl)pyrazolo[1,5-a]pyridin-3-yl]-N-(3-pyridinyl-methyl)-2-pyrimidinamine

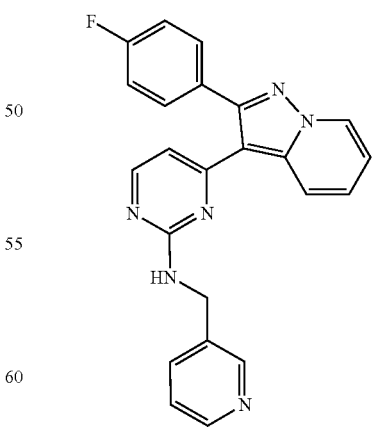

In a similar manner as described for Example 60, from 2-(4-fluorophenyl)-3-(4-(2-methylsulfinyl)pyrimidinyl) pyrazolo[1,5-a]pyridine (Example 58, 0.083 g, 0.25 mmol) and 3-aminomethylpyridine was obtained the title compound as a white solid, 0.071 g (72%). ¹H NMR (CDCl₃) δ 4.72 (d, J=6.1 Hz, 2H), 5.59 (bs, 1H), 6.38 (d, J=5.4 Hz, 1H), 6.86 (t, J=6.8 Hz, 1H), 7.12 (t, J=8.7 Hz, 2H), 7.18 (t, J=7.6 Hz, 1H), 7.27 (dd, J=4.9, 7.7 Hz, 1H), 7.58 (dd, J=5.5, 8.4 Hz, 2H), 7.72 (d, J=7.6 Hz, 1H), 8.02 (bs, 1H), 8.06 (d, J=5.3 Hz, 1H), 8.45 (d, J=6.8 Hz, 1H), 8.53 (d, J=4.6 Hz, 1H), 8.66 (s, 1H); APESI+MS m/z 397 (M+1)⁻.

Example 82

4-[2-(4-Fluorophenyl)pyrazolo[1,5-a]pyridin-3-yl]-N-(2-pyridinylmethyl)-2-pyrimidinamine

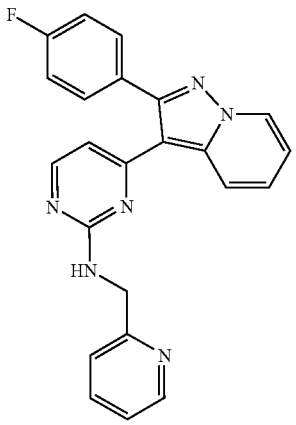

In a similar manner as described for Example 60, from 2-(4-fluorophenyl)-3-(4-(2-methylsulfinyl)pyrimidinyl) pyrazolo[1,5-a]pyridine (Example 58, 0.085 g, 0.25 mmol) and 2-aminomethylpyridine was obtained the title compound as a white solid, 0.047 g (47%). ¹H NMR (CDCl₃) δ 4.82 (d, J=5.7 Hz, 2H), 6.13 (bs, 1H), 6.35 (d, J=5.3 Hz, 1H), 6.87 (t, J=6.7 Hz, 1H), 7.12 (t, J=8.6 Hz, 2H), 7.18–7.23 (m, 2H), 7.36 (d, J=7.8 Hz, 1H), 7.59 (dd, J=5.5, 8.6 Hz, 2H), 7.65 (dt, J=1.6, 7.7 Hz, 1H), 8.07 (d, J=5.3 Hz, 1H), 8.18 (bs, 1H), 8.46 (d, J=7.0 Hz, 1H), 8.60 (d, J=4.9 Hz, 1H); APESI+MS m/z 397 (M+1)⁻.

Example 83

4-[2-(4-Fluorophenyl)pyrazolo[1,5-a]pyridin-3-yl]-N-(4-pyridinyl-methyl)-2-pyrimidinamine

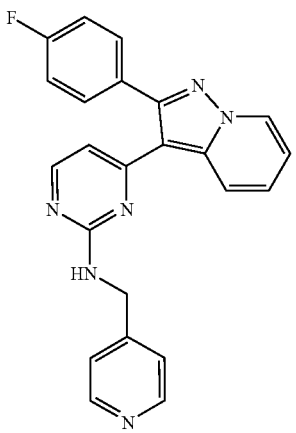

In a similar manner as described for Example 60, from 2-(4-fluorophenyl)-3-(4-(2-methylsulfinyl)pyrimidinyl) pyrazolo[1,5-a]pyridine (Example 58) and 4-aminomethylpyridine was obtained the title compound as a white solid, (80%). ¹H NMR (CDCl₃) δ 4.71 (d, J=6.2 Hz, 2H), 5.69 (bs, 1H), 6.38 (d, J=5.3 Hz, 1H), 6.85 (t, J=6.8 Hz, 1H), 7.11 (t, J=8.6 Hz, 3H), 7.33 (d, J=5.5 Hz, 2H), 7.58 (dd, J=5.5, 8.6 Hz, 2H), 7.8 (bs, 1H), 8.06 (d, J=5.3 Hz, 1H), 8.45 (d, J=6.9 Hz, 1H), 8.58 (d, J=5.9 Hz, 2H); APESI+MS m/z 397 (M+1)⁻.

Example 84

2-(4-Fluorophenyl)-3-(2-phenoxypyrimidin-4-yl)-6-(trifluoromethyl)pyrazolo[1,5-a]pyridine

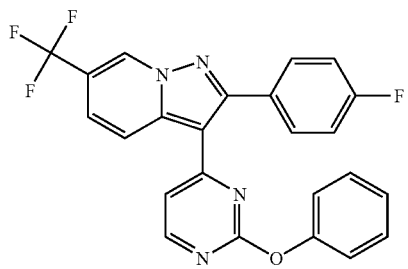

A mixture of 2-(4-fluorophenyl)-3-(4-(2-methylsulfonyl)pyrimidinyl)-6-trifluoromethylpyrazolo-[1,5-a]pyridine (Example 78, 0.10 g, 0.23 mmol) phenol (0.10 g, 1.06 mmol) and sodium carbonate (0.10 g, 0.94 mmol) in DMF (1 ml) was stirred at 10° C. for 4 h. Water was added and the resultant precipitate was collected by filtration then dried under vacuum to give the title compound as a white solid (0.09 g) ¹H NMR (d₆-DMSO) δ 6.78 (d, 1H), 7.29 (m, 2H), 7.35–7.42 (m, 3H), 7.48–7.57 (m, 3H), 7.67 (m, 2H), 7.96 (d, 1H), 8.48 (d, 1H), 9.50 (brs, 1H), MS (+ve electrospray) 519 (MH+).

Example 85

3-({4-[2-(4-Fluorophenyl)-6-(trifluoromethyl)pyrazolo[1,5-a]pyridin-3-yl]pyrimidin-2-yl}oxy)-N,N-dimethylaniline

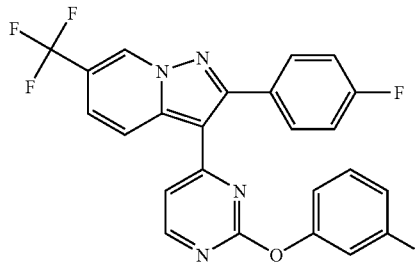

In a similar manner as described for Example 84 using 3-(dimethylamino)phenol, the title compound was obtained as a pale purple solid. ¹H NMR (d₆-DMSO) δ 2.93 (s, 6H), 6.54 (dd, 1H), 6.61 (t, 1H), 6.71 (dd, 1H), 6.74 (d, 1H), 7.32 (t, 1H), 7.35–7.45 (m, 3H), 7.67 (m, 2H), 8.09 (d, 1H), 8.45 (d, 1H), 9.50 (brs, 1H). MS (+ve electrospray) 494 (MH+).

Example 86

3-[2-(2,5-Dimethylphenoxy)pyrimidin-4-yl]-2-(4-fluorophenyl)-6-(trifluoromethyl)pyrazolo[1,5-a]pyridine

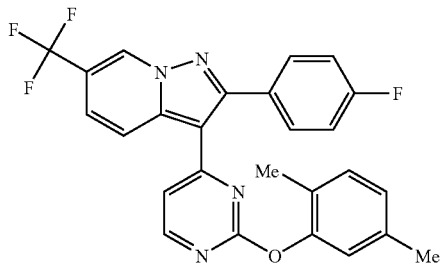

In a similar manner as described for Example 84 using 2,5-dimethylphenol, the title compound was obtained as an off-white solid. $^1$H NMR (d$_6$-DMSO) δ 2.08 (s, 3H), 2.34 (s, 3H), 6.75 (d, 1H), 7.05 (d, 1H), 7.12 (dd, 1H), 7.30 (d, 1H), 7.35–7.48 (m, 3H), 7.66 (m, 2H), 7.86 (d, 1H), 8.45 (d, 1H), 9.50 (brs, 1H). MS (+ve electrospray) 479 (MH+).

Example 87

N-[3-(dimethylamino)propyl]-N-[4-(2-(4-fluorophenyl)-6-(trifluoromethyl)pyrazolo[1,5-a]pyridin-3-yl pyrimidin-2-yl]amine

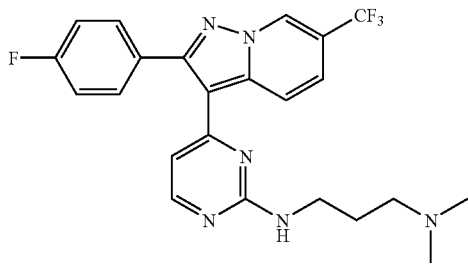

a) 1-(4-Fluorophenyl)-2-(2-(5-trifluoromethyl)pyridyl) ethanone.

To a solution of 4-fluoroacetophenone (13.8 g, 0.100 mol) and 2-chloro-5-trifluoromethylpyridine (20.0 g, 0.110 mol) in tetrahydrofuran (400 mL) was added sodium hydride (95%, 5.56 g, 0.220 mol) in several portions. The reaction was stirred at room temperature for 72 h then carefully quenched by the addition of water (300 mL) and diethyl ether (200 mL). The organic layer was separated and extracted with 6N HCl (2×300 mL). The aqueous extracts were cooled to 0° C. and 6N NaOH was used to adjust the solution to pH 12. The mixture was then extracted with diethyl ether and the combined organic extracts were dried (MgSO$_4$). The drying agent was removed by filtration and the filtrate was evaporated to dryness to afford the title compound as a tautomeric mixture, 20.9 g (73%). $^1$H NMR (CDCl$_3$) δ 8.87(s), 8.63(s), 8.14(dd, J=5.1, 8.4 Hz), 8.00–7.83(m), 7.51(d, J=8.4 Hz), 7.22–7.12(m), 6,13(s), 4.60(s). MS (ES+ve): 284 (100, M$^+$+1).

b) 1-(4-Fluorophenyl)-2-(2-(5-trifluoromethyl)pyridyl) ethanone Oxime.

To a solution of 1-(4-fluorophenyl)-2-(2-(5-trifluoromethyl)pyridyl)ethanone (80.0 g, 0.282 mol) in methanol (1 L) at room temperature was added 10% aqueous sodium hydroxide (436 mL, 1.09 mol). The resulting solution was stirred vigorously as solid hydroxylamine hydrochloride (98.0 g, 1.40 mol) was added. The mixture was heated to reflux for 2 h, treated with decolorizing charcoal while hot, then filtered through Celite while hot. The filtrate was concentrated to one-half its original volume and then cooled to 0° C. with stirring for one hour. The resulting solids were collected by filtration, washed with water, and dried under vacuum at 50° C. overnight to provide the title compound as a light yellow powder, 73.9 g (88%). $^1$H NMR (d$_6$-DMSO) δ 11.60(s, 1H), 8.86(s, 1H), 8.14(dd, 1H, J=2.1, 8.1 Hz), 7.78(dd, 2H, J=5.7, 9.0 Hz), 7.53(d, 1H, J=8.4 Hz), 7.23(t, 2H, J=9.0 Hz), 4.40(s, 2H). MS (ES+ve): 299 (70, M$^+$+1).

c) 3-(4-Fluorophenyl)-2-(2-(5-trifluoromethyl)pyridyl)-2H-azirine.

To a solution of 1-(4-fluorophenyl)-2-(2-(5-trifluoromethyl)pyridyl)ethanone oxime (25.0 g, 0.084 mol) in methylene chloride (400 mL) was added triethylamine (46.7 mL, 0.335 mol). The solution was cooled to 0° C. under a nitrogen atmosphere, and trifluoroacetic anhydride (140.1 mL, 0.100 mol) was added dropwise. The reaction was stirred for 0.5 h then quenched with water. The organic layer was separated and dried (MgSO$_4$). The drying agent was removed by filtration and the solvent was evaporated from the filtrate to leave an oil. The residue was loaded onto a silica gel column and eluted with 15% ethyl acetate in hexanes to give the title compound as an oil which solidified on standing, 19.4 g (82%). $^1$H NMR (CDCl$_3$) δ 8.76(s, 1H), 7.93(dd, 2H, J=5.4, 8.7 Hz), 7.83(dd, 1H, J=2.1, 8.4 Hz), 7.27(t, 2H, J=8.7 Hz), 7.21(d, 1H, J=8.1 Hz), 3.54 (s, 1H). MS (ES+ve): 281 (100, M$^+$+1).

d) 2-(4-Fluorophenyl)-6-trifluoromethylpyrazolo[1,5-a]pyridine.

3-(4-Fluorophenyl)-2-(2-(5-trifluoromethyl)pyridyl)-2H-azirine (40.0 g, 0.143 mol) was dissolved in 1,2,4-trichlorobenzene (400 mL) and the mixture was heated to 200° C. for 10 h. The reaction mixture was then cooled to room temperature and poured onto a silica gel column. The column was eluted with hexanes to remove the 1,2,4-trichlorobenzene, and then with 20% diethyl ether in hexanes to elute the product. The desired fractions were combined and the solvent was evaporated under reduced pressure to leave the title compound, 28.7 g (71%). $^1$H NMR (CDCl$_3$) δ 8.84(s, 1H), 7.98(dd, 2H, J=5.4, 8.7 Hz), 7.65(d, 1H, J=9.3 Hz), 7.28(d, 1H, J=9.3 Hz), 7.20(t, 2H, J=8.7 Hz), 6.88(s, 1H). MS (ES+ve): 281 (100, M$^+$+1).

e) 2-(4-Fluorophenyl)-3-acetyl-6-trifluoromethylpyrazolo[1,5-a]pyridine.

To a mixture of 2-(4-fluorophenyl)-6-trifluoromethylpyrazolo[1,5-a]pyridine (10.30 g, 36.76 mmol) and acetic anhydride (100 mL) was added conc. sulfuric acid (10 drops) and the mixture was stirred and heated at reflux for 1 h. The reaction mixture was cooled to room temperature and poured into ice water (300 mL). 2N Aqueous sodium hydroxide solution was added to raise the pH of the solution to about 10 and the resulting orange precipitate was collected by filtration. The solid was washed with water, air-dried, and then dried under vacuum to afford the title compound as an orange solid, 11.87 g (quant.). $^1$H NMR (d$_6$-DMSO) δ 9.58 (s, 1H), 8.41 (d, 1H, J=9.3 Hz), 7.89 (d, 1H, J=9.5 Hz), 7.74 (m, 2H), 7.39 (m, 2H), 2.22 (s, 3H). MS (+ve ion electrospray) 323 (70), (MH+).

f) 2-(4-fluorophenyl)-3-(3-(dimethylamino)-2-propenoyl)-6-trifluoromethylpyrazolo[1,5-a]pyridine.

A mixture of 2-(4-fluorophenyl)-3-acetyl-6-trifluoromethylpyrazolo[1,5-a]pyridine (11.85 g), 36.77 mmol) and N,N-dimethylformamide dimethyl acetal (100 mL) was stirred at reflux for 17 h. The mixture was cooled to room temperature and then to 0° C. The resulting orange precipitate was collected by filtration, washed with cold hexanes, and dried under vacuum to afford the title compound as an orange solid, 10.17 g (73%). $^1$H NMR ($d_6$-DMSO) δ 9.44 (s, 1H), 8.22 (d, 1H, J=9.4 Hz), 7.75 (m, 2H), 7.65 (d, 1H, J=9.5 Hz), 7.56 (d, 1H, J=12.4 Hz), 7.35 (m, 2H), 5.05 (d, 1H, J=12.3 Hz), 3.04 (s, 3H), 2.56 (s, 3H). MS (+ve ion electrospray) 377 (80), (M+).

g) N-[3-(dimethylamino)propyl]-N-[4-{2-(4-fluorophenyl)-6-(trifluoromethyl)pyrazolo[1,5-a]pyridin-3-yl}pyrimidin-2-yl]amine.

To a mixture of 2-(4-fluorophenyl)-3-(3-(dimethylamino)-2-propenoyl)-6-trifluoromethylpyrazolo[1,5-a]pyridine (2.52 g, 6.68 mmol) and N-(3-dimethylaminopropyl)guanidine (3.23 g, 2.0 equiv, 13.4 mmol) in anhydrous tetrahydrofuran (50 mL) under nitrogen was added a solution of potassium t-butoxide in t-butanol (26.7 mL, 4.0 equiv, 26.7 mmol). The mixture was stirred and heated at reflux for about 17 h and then was allowed to cool to room temperature. Water (50 mL) and diethyl ether (100 mL) were added and the organic phase was seperated. The aqueous phase was extracted with 25% tetrahydrofuran/ether. The combined organic phases were dried over anhydrous sodium sulfate and activated carbon. The drying agents were removed by filtration and the filtrate was concentrated to give the title compound as a light yellow solid 2.9 g, (95%). $^1$H NMR (CDCl$_3$) δ 1.89 (m, 2H), 2.37, (s, 6H), 2.58 (br, 2H), 3.55 (dd, 2H, J=6.4, 12.4 Hz), 5.87 (br, 1H), 6.30 (d, 1H, J=5.2 Hz), 7.12 (t, 2H, J=8.4 Hz), 7.40 (d, 1H, J=9.2 Hz), 7.58 (dd, 2H, J=5.6, 8.8 Hz), 8.06 (d, 1H, J=5.2 Hz), 8.46 (d, 1H, J=9.6 Hz), 8.79 (s, 1H). MS (ES+) m/z 459.50 (M$^+$+H), 414.50 (M$^+$−44).

Example 88

N-[3-(dimethylamino)propyl-N-[4-{6-(trifluoromethyl)-2-[4-(trifluoromethyl)phenyl]pyrazolo[1,5-a]pyridin-3-yl}pyrimidin-2-yl]amine

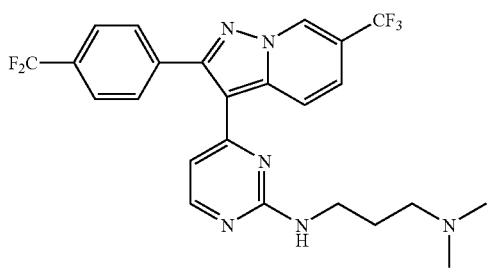

a) 3-Bromo-6-(trifluoromethyl)-2-[4-(trifluoromethyl)phenyl]pyrazolo[1,5-a]pyridine.

In an analogous procedure to Example 91 (a), 2-(4-trifluoromethylphenyl)-6-(trifluoromethyl)pyrazolo[1,5-a]pyridine was converted to the title compound;

$^1$H NMR ($d_6$-DMSO) δ 9.47(1H, s), 8.21(2H, d), 7.94(2H, d), 7.83(1H, d) 7.62(1H, d).

b) Methyl 4-{6-(trifluoromethyl)-2-[4-(trifluoromethyl)phenyl]pyrazolo[1,5-a]pyridin-3-yl}pyrimidin-2-yl sulfide A mixture of 3-bromo-6-(trifluoromethyl)-2-[4-(trifluoromethyl)phenyl]pyrazolo[1,5-a]pyridine (0.82 g), 2-(methylthio)-4-(tributylstannyl)pyrimidine (0.83 g), dichlorobis(triphenylphosphine)palladium (0.14 g) and silver (I) oxide (0.43 g) in 1,4-dioxane (10 mL) was heated to reflux for 18 h. The mixture was cooled, filtered and the filtrate concentrated to dryness. The residue was purified by chromatography eluting with an increasing gradient from cyclohexane to cyclohexane-diethylether (94:6) to give, after concentration to dryness of the appropriate fractions, the title compound as a cream solid (0.46 g); $^1$H NMR ($d_6$-DMSO) δ 9.58(1H, s), 8.50(1H, d), 8.46(1H, d), 7.90(2H, d), 7.84 (2H, d), 7.82(1H, dd), 6.94(1H, d), 2.43(3H, s); m/z 455 (M+1)$^+$.

c) Methyl 4-{6-(trifluoromethyl)-2-[4-(trifluoromethyl)phenyl]pyrazolo[1,5-a]pyridin-3-yl}pyrimidin-2-yl sulfone.

Oxone (6.93 g) in water (115 mL) was mixed with methyl 4-{6-(trifluoromethyl)-2-[4-(trifluoromethyl)phenyl]pyrazolo[1,5-a]pyridin-3-yl}pyrimidin-2-yl sulfide (0.66 g) in methanol (230 mL) and stirred for 2 h. It was diluted with water (1 L) and the resultant suspension removed by filtration and dried at reduced pressure to give the title compound as a beige solid (0.63 g); $^1$H NMR (CDCl$_3$) δ 8.90(1 HS), 8.86(1H, d), 8.59(1H, d), 7.82(2H, d), 7.76(2H, d), 7.67(1H, dd), 7.16(1H, d), 3.39(3H, s); m/z 487 (M+1)$^+$.

d) N-[3-(dimethylamino)propyl]-N-[4-{6-(trifluoromethyl)-2-[4-(trifluoromethyl)phenyl]pyrazolo[1,5-a]pyridin-3-yl}pyrimidin-2-yl]amine.

3-(Dimethylamino)propylamine (0.04 mL) and methyl 4-{6-(trifluoromethyl)-2-[4-(trifluoromethyl)phenyl]pyrazolo[1,5-a]pyridin-3-yl}pyrimidin-2-yl sulfone (0.02 g) were mixed at room temperature and heated with an airgun until a homogenous melt was obtained (2 min). Upon cooling, water was added. The precipitated solid was filtered and dried to give the title compound as a white solid (0.012 g); $^1$H NMR ($d_6$-DMSO) δ 9.52(1H, s), 8.50(1H, bs), 8.16(1H, d), 7.87(4H, dd), 7.69(1H, d), 7.26(1H, bs), 6.34 (1H, bs), 3.25(2H, bs), 2.24(2H, bs), 2.11(6H, s), 1.63(2H, bs); m/z 509 (M+1)+.

Example 89

N-[4-{2-[3-chloro-4-fluorophenyl]-6-(trifluoromethyl)pyrazolo-[1,5-a]pyridin-3-yl}pyrimidin-2-yl]-N-[3-(dimethylamino)propyl]amine

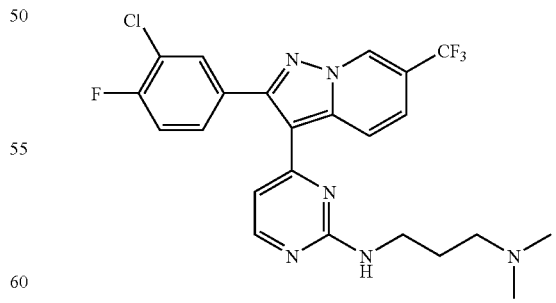

a) 3-Bromo-2-(3-chloro-4-fluorophenyl)-6-(trifluoromethyl)pyrazolo[1,5-a]pyridine.

In an analogous procedure to Example 91(a), 2-(3-chloro-4-fluorophenyl)-6-(trifluoromethyl)pyrazolo[1,5-a]pyridine was converted to the title compound;

¹H NMR (CDCl₃) δ 8.77(1H, s), 8.14(1H, dd), 7.97(1H, m), 7.65(1H, d), 7.37 (1H, dd), 7.27(1H, dd).

b) 4-[2-(3-Chloro-4-fluorophenyl)-6-(trifluoromethyl) pyrazolo[1,5-a]pyridin-3-yl]pyrimidin-2-yl methyl Sulfide.

A mixture of 3-bromo-6-(trifluoromethyl)-2-(3-chloro-4-fluorophenyl)pyrazolo[1,5-a]pyridine (0.79 g), 2-(methylthio)-4-(tributylstannyl)pyrimidine (0.83 g), dichlorobis(triphenylphosphine)palladium (0.14 g) and silver (I) oxide (0.43 g) in 1,4-dioxane (10 mL) was heated to reflux for 18 h. The mixture was cooled, filtered and the filtrate concentrated to dryness. The residue was purified by chromatography eluting with an increasing gradient from cyclohexane to cyclohexane-diethylether (94:6) to give, after concentration to dryness of the appropriate fractions, the title compound as a cream solid (0.54 g); ¹H NMR (CDCl₃) δ 8.84(1H, s), 8.52(1H, d), 8.34(1H, d), 7.72(1H, dd), 7.51 (1H, dd), 7.47(1H, m), 7.25(1H, dd), 6.74(1H, d), 2.61(3H, s).

c) 4-[2-(3-Chloro-4-fluorophenyl)-6-(trifluoromethyl) pyrazolo[1,5-a]pyridin-3-yl]pyrimidin-2-yl methyl Sulfone.

Oxone (5.90 g) in water (100 mL) was mixed with 4-[2-(3-chloro-4-fluorophenyl)-6-(trifluoromethyl)pyrazolo[1,5-a]pyridin-3-yl]pyrimidin-2-yl methyl sulfide (0.54 g) in methanol (200 mL) and stirred for 2 h. The methanol was removed at reduced pressure and the mixture diluted with water (100 mL). The resultant suspension was removed by filtration and dried at reduced pressure to give the title compound as a yellow solid (0.52 g); ¹H NMR (CDCl₃) δ 8.87 (1H, s), 8.83(1H, d), 8.61(1H, d), 7.71(1H, dd), 7.66 (1H, dd), 7.48(1H, m), 7.32(1H, dd), 7.21(1H, dd), 3.40(3H, s).

d) N-[4-{2-[3-chloro-4-fluorophenyl]-6-(trifluoromethyl) pyrazolo[1,5-a]pyridin-3-ylpyrimidin-2-yl]-N-[3-(dimethylaminolpropyl]amine.

In an analogous procedure to Example 88d), 4-[2-(3-chloro-4-fluorophenyl)-6-(trifluoromethyl)pyrazolo[1,5-a]pyridin-3-yl]pyrimidin-2-yl methyl sulfone (0.02 g) and 3-(dimethylamino)propylamine (0.04 mL) gave the title compound; ¹H NMR (d₆-DMSO) δ 9.50(1H, s), 8.53(1H, bs), 8.18(1H, d), 7.84(1H, dd), 7.70 (1H, d), 7.63(1H, m), 7.57(1H, dd), 7.28(1H, bs), 6.40(1H, bs), 3.29(2H, bs), 2.25(2H, bm), 1.65(6H, bs); m/z 493 (M+1)⁺.

Example 90

N-{4-[2-(3-chlorophenyl)-6-(trifluoromethyl)pyrazolo[1,5-a]pyridin-3-yl]pyrimidin-2-yl}-N-[3-(dimethylamino)propyl]amine

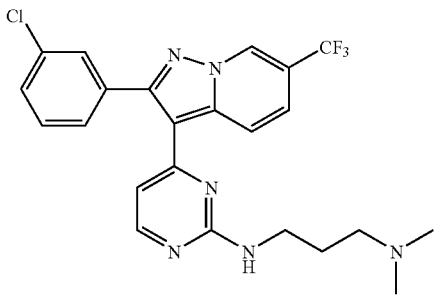

a) 3-Bromo-2-(3-chlorophenyl)-6-(trifluoromethyl)pyrazolo[1,5-a]pyridine.

In an analogous procedure to Example 91(a), 2-(3-chlorophenyl)-6-(trifluoromethyl)pyrazolo[1,5-a]pyridine was converted to the title compound;

¹H NMR (CDCl₃) δ 8.79(1H, s), 8.06(1H, s), 7.97(1H, m), 7.66(1H, d), 7.45(2H, d), 7.36(1H, d).

b) Methyl 4-{6-(trifluoromethyl)-2-[3-chlorophenyl]pyrazolo[1,5-a]pyridin-3-yl}pyrimidin-2-yl sulfide.

A mixture of 3-bromo-6-(trifluoromethyl)-2-[3-chlorophenyl]pyrazolo[1,5-a]pyridine (2.0 g), 2-(methylthio)-4-(tributylstannyl)pyrimidine (2.32 g), dichlorobis(triphenylphosphine)palladium (0.37 g) and silver (I) oxide (1.23 g) in 1,4-dioxane (20 mL) was heated to reflux for 20 h. The mixture was cooled, filtered and the filtrate concentrated to dryness. The residue was purified by chromatography eluting with cyclohexane-ethylacetate (90:10) to give, after concentration to dryness of the appropriate fractions, the title compound as a cream solid (0.95 g); ¹H NMR (d₆-DMSO) δ 9.58(1H, s), 8.53–8.47(2H, m), 7.84(1H, d), 7.70(1H, s), 7.63(1H, m), 7.57(2H, m), 6.94(1H, d) 2.43(3H, s); m/z 421(M+1)⁺.

c) Methyl 4-{6-(trifluoromethyl)-2-[3-chlorophenyl]pyrazolo[1,5-a]pyridin-3-yl}pyrimidin-2-yl sulfone.

Oxone (9.5 g) in water (75 mL) was mixed with methyl 4-{6-(trifluoromethyl)-2-[3-chlorophenyl]pyrazolo[1,5-a]pyridin-3-yl}pyrimidin-2-yl sulfide (0.95 g) in methanol (200 mL) and stirred for 2 h. The methanol was removed under reduced pressure and then water added (200 ml). The resultant suspension was removed by filtration and dried at reduced pressure to give the title compound as a pink solid (0.80 g); ¹H NMR (d₆-DMSO) δ 9.67(1H, s), 8.90(1H, d), 8.64(1H, d) 7.98(1H, dd), 7.77(1H, s), 7.71–7.56(3H, m), 7.44(1H, d), 3.42(3H, s); m/z 453(M+1)⁺.

d) N-{4-[2-(3-chlorophenyl)-6-(trifluoromethyl)pyrazolo[1,5-a]pyridin-3-yl]pyrimidin-2-yl}-N-[3-(dimethylamino)propyl]amine.

In an analogous procedure to Example 88(d), 4-[2-(3-chlorophenyl)-6-(trifluoromethyl)pyrazolo[1,5-a]pyridin-3-yl]pyrimidin-2-yl methyl sulfone (0.02 g) and 3-(dimethylamino)propylamine (0.04 mL) gave the title compound; ¹H NMR (d₆-DMSO) δ 9.51(1H, s), 8.49(1H, bs), 8.16(1H, d), 7.72–7.65(2H, m), 7.61–7.51(3H, m), 7.28(1H, bs), 6.32 (1H, bs), 3.30(2H, bs), 2.25(2H, t), 2.12(6H, s), 1.66(2H, m); m/z 475(M+1)⁺.

Example 91

N-(4-[2-(4-fluorophenyl)-6-(trifluoromethyl)pyrazolo[1,5-a]pyridin-3-yl]pyrimidin-2-yl}-N-[2-(dimethylamino)ethyl]amine

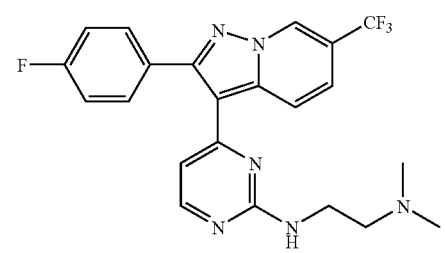

a) 3-Bromo-2-(4-fluorophenyl)-6-(trifluoromethyl)pyrazolo[1,5-a]pyridine.

2-(4-Fluorophenyl)-6-(trifluoromethyl)pyrazolo[1,5-a]pyridine (5 g, Example 1(d)) in tetrahydrofuran (50 mL) was treated with N-bromosuccinimide (3.5 g). After 1 h, the mixture was concentrated in vacuo and partitioned between dichloromethane and 2N NaOH. The organic extract was dried and concentrated. The residue was purified by chromatography on silica to give the title compound (5.2 g); ¹H NMR (CDCl₃) δ 8.78(1H, s), 8.05(2H, dd), 7.65(1H, d) 7.35(1H, dd), 7.20 (2H, dd); m/z 359(M+1)+.

b) 4-[2-(4-Fluorophenyl)-6-(trifluoromethyl)pyrazolo[1,5-a]pyridin-3-yl]pyrimidin-2-yl Methyl Sulfide.

A mixture of 3-bromo-6-(trifluoromethyl)-2-(4-fluorophenyl)pyrazolo[1,5-a]pyridine (0.50 g), 2-(methylthio)-4-(tributylstannyl)pyrimidine (0.58 g), dichlorobis(triphenylphosphine)palladium (0.098 g) and silver (I) oxide (0.30 g) in 1,4-dioxane.(5 mL) was heated to reflux for 18 h. The mixture was cooled, filtered and the filtrate concentrated to dryness. The residue was purified by chromatography eluting with cyclohexane-ethylacetate (96:4) to give, after concentration to dryness of the appropriate fractions, the title compound as a cream solid (0.23 g); ¹H NMR (CDCl₃) δ 8.85(1H, bd), 8.55(1H, d), 8.30(1H, d), 7.60(2H, dd), 7.50 (1H, dd), 7.18(2H, dd), 6.72(1H, d), 2.75(3H, s); m/z 405 (M+1)+.

c) 4-[2-(4-Fluorophenyl)-6-(trifluoromethyl)pyrazolo[1,5-a]pyridin-3-yl]pyrimidin-2-yl Methyl Sulfone.

Oxone (2.53 g) in water (40 mL) was mixed with 4-[2-(4-fluorophenyl)-6-(trifluoromethyl)pyrazolo[1,5-a]pyridin-3-yl]pyrimidin-2-yl methyl sulfide (0.23 g) in methanol (80 mL) and stirred for 2 h. The methanol was removed at reduced pressure and the mixture diluted with water (400 mL). The resultant suspension was removed by filtration and dried at reduced pressure to give the title compound as a yellow solid (0.25 g); ¹H NMR (CDCl₃) δ 8.88(1H, s), 8.85(1H, d), 8.55(1H, d), 7.65(1H, dd), 7.58(2H, dd), 7.24 (2H, dd), 7.19(1H, d), 3.40(3H, s).

d) N-{4-[2-(4-fluorophenyl)-6-(trifluoromethyl)pyrazolo[1,5-a]pyridin-3-yl]pyrimidin-2-yl}-N-[2-(dimethylamino)ethyl]amine.

In an analogous procedure to Example 88(d), 4-[2-(4-fluorophenyl)-6-(trifluoromethyl)pyrazolo[1,5-a]pyridin-3-yl]pyrimidin-2-yl methyl sulfone (0.02 g) and 2-(dimethylamino)ethylamine (0.04 mL) gave the title compound; ¹H NMR (CDCl₃) δ 8.83(1H, s), 8.51(1H, d), 8.11(1H, d), 7.63(2H, dd), 7.43 (1H, dd), 7.15(2H, dd), 6.33(1H, d), 5.75(1H, bs), 3.60(2H, dt), 2.65(2H, bt), 2.35(6H, s); m/z 445 (M+1)+.

Example 92

N-[4-(diethylamino)butyl]-N-(4-{6-(trifluoromethyl)-2-[4-(trifluoromethyl)phenyl]pyrazolo[1,5-a]pyridin-3-yl}pyrimidin-2-yl)amine

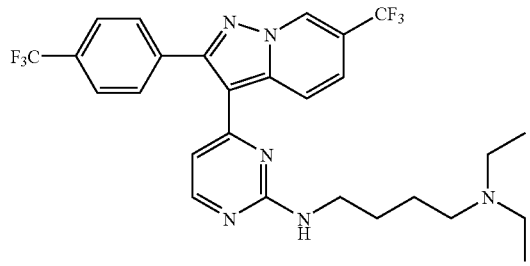

In an analogous procedure to Example 88(d), methyl 4-{6-(trifluoromethyl)-2-[4-(trifluoromethyl)phenyl]pyrazolo[1,5-a]pyridin-3-yl}pyrimidin-2-yl sulfone (0.02 g) and 4-(diethylamino)butylamine (0.04 mL) gave the title compound; ¹H NMR (d₆-DMSO) δ 9.48(1H, s), 8.44(1H, bs), 8.14(1H, d), 7.83(4H, dd), 7.65(1H, d), 6.96(1H, bs), 6.36 (1H, bs), 2.36(2H, bs), 2.28(4H, bs), 1.44(4H, bt), 1.33(2H, bd); m/z 450, 535.

Example 93

N-{4-[2-(3-chloro-4-fluorophenyl)-6-(trifluoromethyl)pyrazolo-[1,5-a]pyridin-3-yl]pyrimidin-2-yl}-N-[4-(diethylamino)butyl]amine

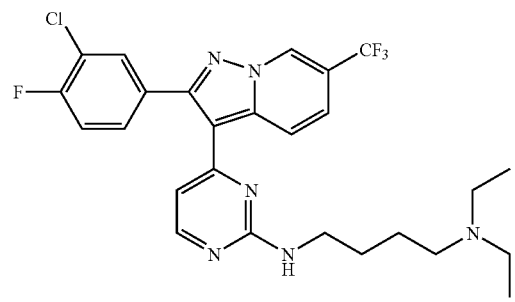

In an analogous procedure to Example 88(d), 4-[2-(3-chloro-4-fluorophenyl)-6-(trifluoromethyl)pyrazolo[1,5-a]pyridin-3-yl]pyrimidin-2-yl methyl sulfone (0.02 g) and 4-(diethylamino)butylamine (0.04 mL) gave the title compound; ¹H NMR (d₆-DMSO) δ 9.51(1H, s), 8.49(1H, bs), 8.19(1H, d), 7.85(1H, dd), 7.71 (1H, d), 7.64(1H, m), 7.58 (1H, dd), 7.31 (1H, bs), 6.40 (1H, bs), 3.26(2H, bs), 2.43 (4H, q), 2.36(2H, bm), 1.53(2H, bs), 1.43(2H, bs), 0.93(6H, t); m/z 535 (M+1)+.

Example 94

N-{4-[2-(3-chlorophenyl)-6-(trifluoromethyl)pyrazolo[1,5-a]pyridin-3-yl]pyrimidin-2-yl}-N-[4-(diethylamino)butyl]amine

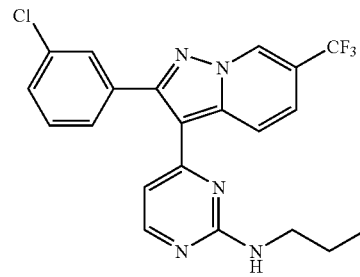

In an analogous procedure to Example 88(d), 4-[2-(3-chlorophenyl)-6-(trifluoromethyl)pyrazolo[1,5-a]pyridin-3-yl]pyrimidin-2-yl methyl sulfone (0.02 g) and 4-(diethylamino)butylamine (0.04 mL) gave the title compound; ¹H NMR (d₆DMSO) δ 9.51(1H, s), 8.47(1H, bs), 8.14(1H, d), 7.73–7.66(2H, m), 7.6–17.51(3H, m), 7.31(1H, bs), 6.32 (1H, bs), 3.27(2H, bs), 2.41(4H, q), 2.35(2H, t), 1.53(2H, m), 1.43(2H, m), 0.91(6H, t); m/z 517(M+1)+.

Example 95

N-[2-(diethylamino)ethyl]-N-(4-{6-(trifluoromethyl)-2-[4-(trifluoromethyl)phenyl]pyrazolo[1,5-a]pyridin-3-yl}pyrimidin-2-yl)amine

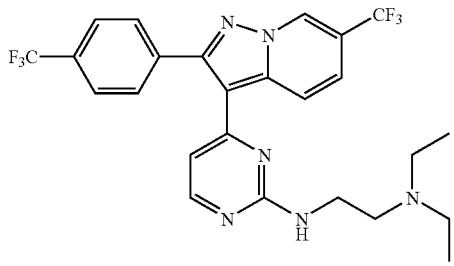

In an analogous procedure to Example 88(d), methyl 4-{6-(trifluoromethyl)-2-[4-(trifluoromethyl)phenyl]pyrazolo[1,5-a]pyridin-3-yl}pyrimidin-2-yl sulfone (0.02 g) and 2-(diethylamino)ethylamine (0.04 mL) gave the title compound; $^1$H NMR (d$_6$-DMSO) δ 9.53(1H, s), 8.48(1H, bs), 8.19(1H, d), 7.87(4H, dd), 7.70(1H, d), 6.99(1H, bs), 6.38 (1H, bs), 0.93(6H, bt); m/z 450, 523 (M+1)$^+$.

Example 96

N-{4-[2-(3-chlorophenyl)-6-(trifluoromethyl)pyrazolo[1,5-a]pyridin-3-yl]pyrimidin-2-yl}-N-[2-(diethylamino)ethyl]amine

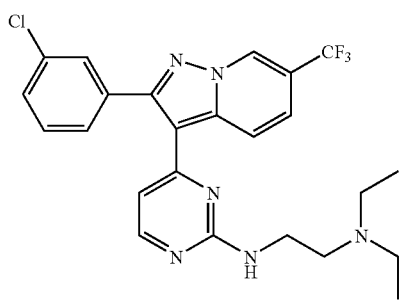

In an analogous procedure to Example 88(d), 4-[2-(3-chlorophenyl)-6-(trifluoromethyl)pyrazolo[1,5-a]pyridin-3-yl]pyrimidin-2-yl methyl sulfone (0.02 g) and 2-(diethylamino)ethylamine (0.04 mL) gave the title compound; $^1$H NMR (d$_6$-DMSO) δ 9.51 (1H, s), 8.47(1H, bs), 8.16(1H, d), 7.72–7.65(2H, m), 7.61–7.51(3H, m), 7.00(1H, bs), 6.34 (1H, bs), 0.93(6H, bs); m/z 489(M+1)$^+$.

Example 97

N-[2-(dipropylamino)ethyl]-N-(4-{6-(trifluoromethyl)-2-[4-(trifluoromethyl)phenyl]pyrazolo[1,5-a]pyridin-3-yl}pyrimidin-2-yl)amine

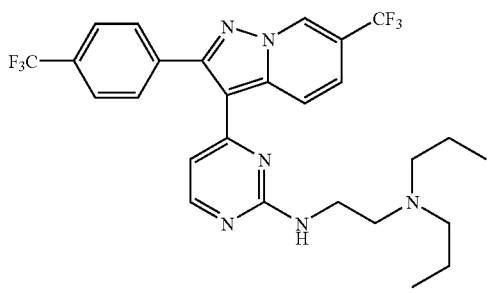

In an analogous procedure to Example 88(d), methyl 4-{6-(trifluoromethyl)-2-[4-(trifluoromethyl)phenyl]pyrazolo[1,5-a]pyridin-3-yl}pyrimidin-2-yl sulfone (0.02 g) and 2-(dipropylamino)ethylamine (0.04 mL) gave the title compound; $^1$H NMR (d$_6$-DMSO) δ 9.52(1H, s), 8.46(1H, bs), 8.18(1H, d), 7.87(4H, dd), 7.68(1H, d), 6.96(1H, bs), 6.37 (1H, bs), 2.33(4H, bs), 1.37(4H, bs), 1.48(4H, bs), 0.79 (6H, bs); m/z 450, 551 (M+1)$^+$.

Example 98

N-{4-[2-(3-chloro-4-fluorophenyl)-6-(trifluoromethyl)pyrazolo-[1,5-a]pyridin-3-yl]pyrimidin-2-yl}-N-[2-(dipropylamino)ethyl]amine

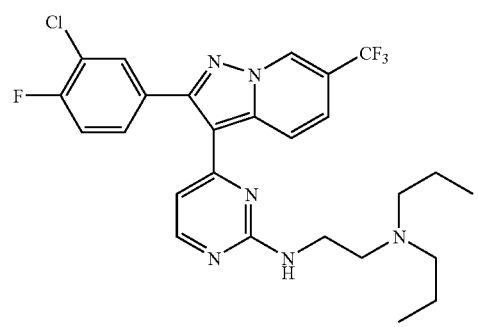

In an analogous procedure to Example 88(d), 4-[2-(3-chloro-4-fluorophenyl)-6-(trifluoromethyl)pyrazolo[1,5-a]pyridin-3-yl]pyrimidin-2-yl methyl sulfone (0.02 g) and 2-(dipropylamino)ethylamine (0.04 mL) gave the title compound; $^1$H NMR (d$_6$-DMSO) δ 9.50(1H, s), 8.45(1H, bs), 8.19(1H, d), 7.84(1H, dd), 7.68(1H, d), 7.63(1H, m), 7.56 (1H, dd), 6.97(1H, bs), 6.41(1H, bs), 2.34(4H, bs), 1.37(4H, bs), 0.80(6H, bs); m/z 535 (M+1)$^+$.

Example 99

N-{4-[2-(3-chlorophenyl)-6-(trifluororbethyl)pyrazolo[1,5-a]pyridin-3-yl]pyrimidin-2-yl}-N-[2-(dipropylamino)ethyl]amine

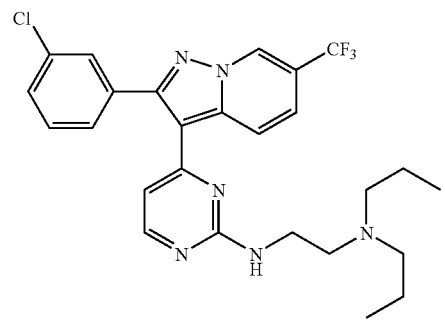

In an analogous procedure to Example 88(d), 4-[2-(3-chlorophenyl)-6-(trifluoromethyl)pyrazolo[1,5-a]pyridin-3-yl]pyrimidin-2-yl methyl sulfone (0.02 g) and 2-(dipropylamino)ethylamine (0.04 mL) gave the title compound; $^1$H NMR (d$_6$-DMSO) δ 9.51(1H, s) 8.47(1H, bs), 8.16(1H, d), 7.66(2H, m), 7.61–7.51(3H, m), 6.97(1H, bs), 6.34(1H, bs), 2.35(4H, bs), 1.37(4H, m), 0.80(6H, s); m/z 517(M+1)$^+$.

Example 100

N-{4-[2-(3-chloro-4-fluorophenyl)-6-(trifluoromethyl)pyrazolo-[1,5-a]pyridin-3-yl]pyrimidin-2-yl}-N-[2-(diisopropylamino)ethyl]amine

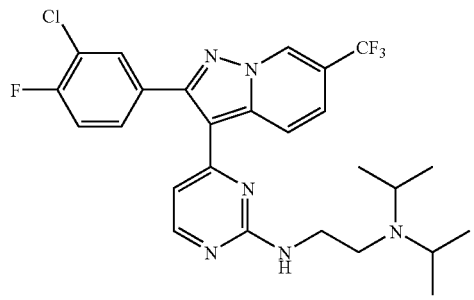

In an analogous procedure to Example 88(d), 4-[2-(3-chloro-4-fluorophenyl)-6-(trifluoromethyl)pyrazolo[1,5-a]pyridin-3-yl]pyrimidin-2-yl methyl sulfone (0.02 g) and 2-(diisopropylamino)ethylamine (0.04 mL) gave the title compound; $^1$H NMR (d$_6$-DMSO) δ 9.51(1H, s), 8.40(1H, bs), 8.21(1H, d), 7.84(1H, dd), 7.68(1H, d), 7.64(1H, m), 7.57(1H, dd), 7.03(1H, bs), 6.47(1H, bs), 3.23(2H, bs), 2.94(2H, bs), 0.95(12H, bs); m/z 535 (M+1)$^+$.

Example 101

N-{4-[2-(3-chlorophenyl)-6-(trifluoromethyl)pyrazolo[1,5-a]pyridin-3-yl]pyrimidin-2-yl)-N-[2-(diisopropylamino)ethyl]amine

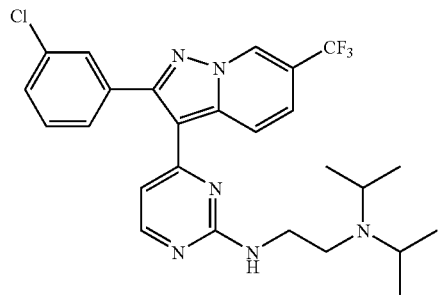

In an analogous procedure to Example 88(d), 4-[2-(3-chlorophenyl)-6-(trifluoromethyl)pyrazolo[1,5-a]pyridin-3-yl]pyrimidin-2-yl methyl sulfone (0.02 g) and 2-(diisopropylamino)ethylamine (0.04 mL) gave the title compound; $^1$H NMR (d$_6$-DMSO) δ 9.50(1H, s), 8.40(1H, bs), 8.16(1H, d), 7.71–7.63(2H, m), 7.61–7.51(3H, m), 7.00(1H, bs), 6.34(1H, bs), 3.24(2H, bs), 2.93(2H, m), 0.95(12H, d); m/z 517(M+1)$^+$.

Example 102

N-{4-[2-(4-fluorophenyl)-6-(trifluoromethyl)pyrazolo[1,5-a]pyridin-3-yl]pyrimidin-2-yl}-N-(2-pyrrolidin-1-ylethyl)amine

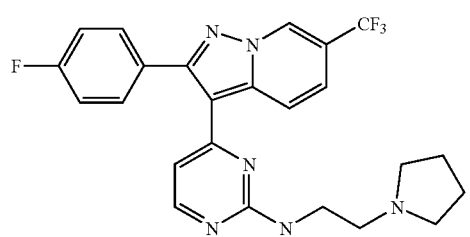

2-Pyrrolidin-1-ylethylamine (0.04 mL) and 4-[2-(4-fluorophenyl)-6-(trifluoromethyl)pyrazolo[1,5-a]pyridin-3-yl]pyrimidin-2-yl methyl sulfone (0.02 g) were mixed at room temperature and heated with an airgun until a homogenous melt was obtained (2 min). Upon cooling, water was added. The precipitated solid was filtered and dried to give the title compound as a beige solid (0.012 g); $^1$H NMR (CDCl$_3$) δ 8.83(1H, s), 8.51(1H, d), 8.11(1H, d), 7.63(2H, dd), 7.43(1H, dd), 7.15(2H, dd), 6.33(1H, d), 5.75(1H, bs), 3.58(2H, dt), 2.76(2H, t), 2.58(2H, bt), 1.81(2H, bm); m/z 471 (M+1)$^+$.

Example 103

N-(2-pyrrolidin-1-ylethyl)-N-(4-{6-(trifluoromethyl)-2-[4-(trifluoromethyl)phenyl]pyrazolo[1,5-a]pyridin-3-yl}pyrimidin-2-yl)amine

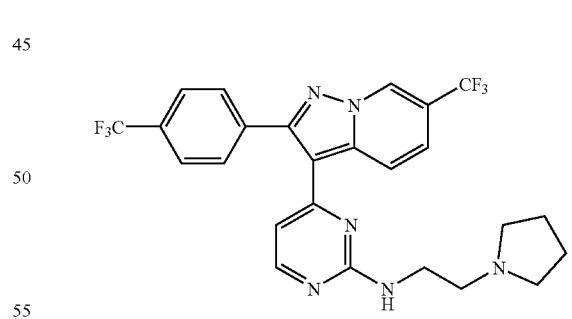

In an analogous procedure to Example 102, methyl 4-{6-(trifluoromethyl)-2-[4-(trifluoromethyl)phenyl]pyrazolo[1,5-a]pyridin-3-yl}pyrimidin-2-yl sulfone (0.02 g), 2-pyrrolidin-1-ylethylamine (0.04 mL) gave the title compound; $^1$H NMR (d$_6$-DMSO) δ 9.53(1H, s), 8.50(1H, bs), 8.19(1H, d), 7.88(4H, dd), 7.70(1H, d), 7.10(1H, bs), 6.39(1H, bs), 2.44(4H, bs), 1.68(4H, bs); m/z 521 (M+1)$^+$.

Example 104

N-{4-[2-(3-chloro-4-fluorophenyl)-6-(trifluoromethyl)pyrazolo-[1,5-a]pyridin-3-yl]pyrimidin-2-yl}-N-(2-pyrrolidin-1-ylethyl)amine

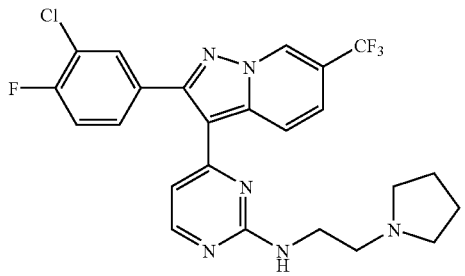

2-Pyrrolidin-1-ylethylamine (0.04 mL) and 4-[2-(3-chloro-4-fluorophenyl)-6-(trifluoromethyl)pyrazolo[1,5-a]pyridin-3-yl]pyrimidin-2-yl methyl sulfone (0.02 g) were mixed at room temperature and heated with an airgun until a homogenous melt was obtained (2 min). Upon cooling, water was added. The precipitated solid was filtered and dried to give the title compound as a beige solid (0.012 g); $^1$H NMR (d$_6$-DMSO) δ 9.50(1H, s), 8.48(1H, bs), 8.18(1H, d), 7.83(1H, d), 7.68(1H, dd), 7.62(1H, m), 7.56(1H, dd), 7.12(1H, bs), 6.42(1H, bs), 2.44(2H, bs), 1.67(4H, bs); m/z 505 (M+1)$^+$.

Example 105

N-{4-[2-(3-chlorophenyl)-6-(trifluoromethyl)pyrazolo[1,5-a]pyridin-3-yl]pyrimidin-2-yl}-N-(2-pyrrolidin-1-ylethyl)amine

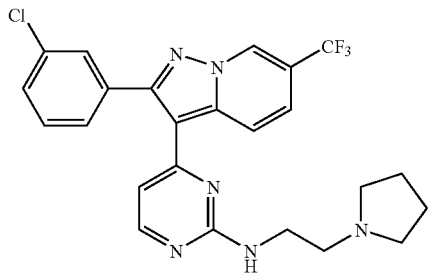

In an analogous procedure to Example 104, 4-[2-(3-chlorophenyl)-6-(trifluoromethyl)pyrazolo[1,5-a]pyridin-3-yl]pyrimidin-2-yl methyl sulfone (0.02 g) and 2-pyrrolidin-1-ylethylamine (0.04 mL) gave the title compound; $^1$H NMR (d$_6$-DMSO) δ 9.51 (1H, s), 8.49(1H, bs), 8.17(1H, d), 7.72–7.65(2H, m), 7.61–7.51 (3H, m), 7.13(1H, bs), 6.37 (1H, bs), 2.57(2H, bs), 2.45(4H, bs), 1.68(4H, s); m/z 487(M+1)$^+$.

Example 106

N-{4-[2-(3-chlorophenyl)-6-(trifluoromethyl)pyrazolo[1,5-a]pyridin-3-yl]pyrimidin-2-yl}-N-(4-pyrrolidin-1-ylbutyl)amine

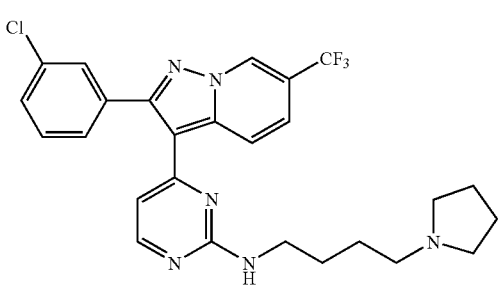

In an analogous procedure to Example 104, 4-[2-(3-chlorophenyl)-6-(trifluoromethyl)pyrazolo[1,5-a]pyridin-3-yl]pyrimidin-2-yl methyl sulfone (0.02 g) and 4-pyrrolidin-1-ylbutylamine (0.04 mL) gave the title compound; $^1$H NMR (d$_6$-DMSO) δ 9.51(1H, s), 8.47(1H, bs), 8.16(1H, d), 7.72–7.65(2H, m), 7.61–7.51(3H, m), 7.31(1H, bs), 6.32 (1H, bs), 3.27(2H, bs), 2.37(6H, bs), 1.64(4H, bs), 1.55(2H, m), 1.48(2H, m); m/z. 515(M+1)$^+$.

Example 107

N-(4-[2-(4-fluorophenyl)-6-(trifluoromethyl)pyrazolo[1,5-a]pyridin-3-yl]pyrimidin-2-yl}-N-(2-piperidin-1-ylethyl)amine

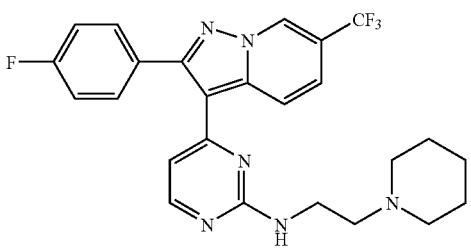

In an analogous procedure to Example 104, 4-[2-(4-fluorophenyl)-6-(trifluoromethyl)pyrazolo[1,5-a]pyridin-3-yl]pyrimidin-2-yl methyl sulfone (0.02 g), 2-piperidin-1-ylethylamine (0.04 mL) gave the title compound; $^1$H NMR (CDCl$_3$) δ 8.83(1H, s), 8.51(1H, d), 8.11(1H, d), 7.63(2H, dd), 7.43 (1H, dd), 7.15(2H, dd), 6.33(1H, d), 5.75(1H, bs), 3.60(2H, dt), 2.55(2H, t), 2.50(4H, bm), 1.60–1.50 (6H, m); m/z 485 (M+1)+.

Example 108

N-(2-piperidin-1-ylethyl)-N-(4-{6-(trifluoromethyl)-2-[4-(trifluoromethyl)phenyl]pyrazolo[1,5-a]pyridin-3-yl}pyrimidin-2-yl)amine

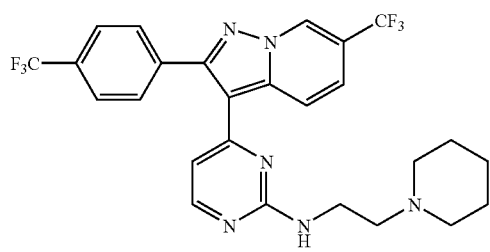

In an analogous procedure to Example 104, methyl 4-{6-(trifluoromethyl)-2-[4-(trifluoromethyl)phenyl]pyrazolo[1,5-a]pyridin-3-yl}pyrimidin-2-yl sulfone (0.02 g), 2-piperidin-1-ylethylamine (0.04 mL) gave the title compound; $^1$H NMR (d$_6$-DMSO) δ 9.52(1H, s), 8.47(1H, bs), 8.19(1H, d), 7.87(4H, dd), 7.69(1H, d), 7.02(1H, bs), 6.41(1H, bs), 2.46–2.24(4H, bm), 1.48(4H, bt), 1.37(2H, bs); m/z 450, 535 (M+1)+.

Example 109

N-{4-[2-(3-chloro-4-fluorophenyl)-6-(trifluoromethyl)pyrazolo[1,5-a]pyridin-3-yl]pyrimidin-2-yl}-N-(2-pipridin-1-ylethyl)amin

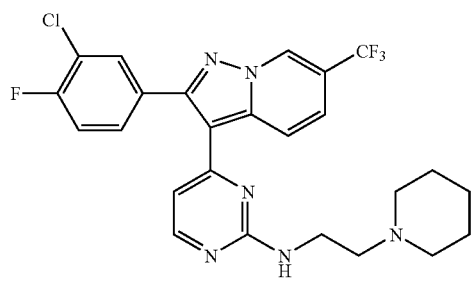

In an analogous procedure to Example 104, 4-[2-(3-chloro-4-fluorophenyl)-6-(trifluoromethyl)pyrazolo[1,5-a]pyridin-3-yl]pyrimidin-2-yl methyl sulfone (0.029), 2-piperidin-1-ylethylamine (0.04 mL) gave the title compound; $^1$H NMR (d$_6$-DMSO) δ 9.52(1H, s), 8.47(1H, bs), 8.20(1H, d), 7.84(1H, dd), 7.69 (1H, d), 7.63(1H, m), 7.57(1H, dd), 7.04(1H, bs), 6.45(1H, bs), 2.41(2H, bs), 2.33(4H, bm), 1.49(4H, bm), 1.38(2H, bm); m/z 519 (M+1)+.

Example 110

N-{4-[2-(3-chlorophenyl)-6-(trifluoromethyl)pyrazolo[1,5-a]pyridin-3-yl]pyrimidin-2-yl}-N-(2-piperidin-1-ylethyl)amine

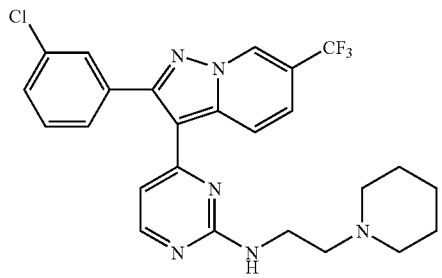

In an analogous procedure to Example 104, 4-[2-(3-chlorophenyl)-6-(trifluoromethyl)pyrazolo[1,5-a]pyridin-3-yl]pyrimidin-2-yl methyl sulfone (0.02 g) and 2-piperidin-1-ylethylamine (0.04 mL) gave the title compound; $^1$H NMR (d$_6$-DMSO) δ 9.51(1H, s), 8.49(1H, bs), 8.16(1H, d), 7.70–7.65(2H, m), 7.61–7.51(3H, m), 7.03(1H, bs), 6.37 (1H, bs), 2.42(2H, m), 2.33(4H, m), 1.49(4H, m), 1.38(2H, m); m/z 501(M+1)+.

Example 111

N-{4-[2-(4-fluorophenyl)-6-(trifluoromethyl)pyrazolo[1,5-a]pyridin-3-yl]pyrimidin-2-yl}-N-(2-piperidin-1-ylpropyl)amine

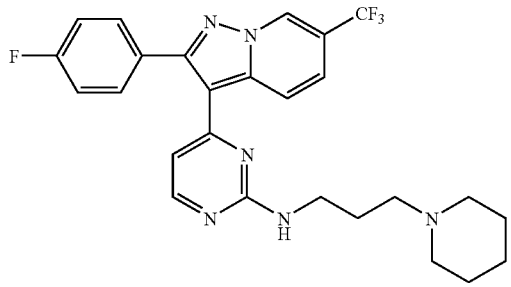

In an analogous procedure to Example 104, 4-[2-(4-fluorophenyl)-6-(trifluoromethyl)pyrazolo[1,5-a]pyridin-3-yl]pyrimidin-2-yl methyl sulfone (0.02 g), 2-piperidin-1-ylpropylamine (0.04 mL) gave the title compound; $^1$H NMR (CDCl$_3$) δ 8.83(1H, s), 8.51(1H, d), 8.11(1H, d), 7.63(2H, dd), 7.43 (1H, dd), 7.15(2H, dd), 6.33(1H, d), 5.75(1H, bs), 3.55(2H, dt), 2.50(2H, t), 2.45(4H, m), 1.85(2H, m), 1.57 (4H, m), 1.50(2H, m); m/z 499 (M+1)+.

Example 112

N-(3-piperidin-1-ylpropyl)-N-(4-{6-(trifluoromethyl)-2-[4-(trifluoromethyl)phenyl]pyrazolo[1,5-a]pyridin-3-yl}pyrimidin-2-yl)amine

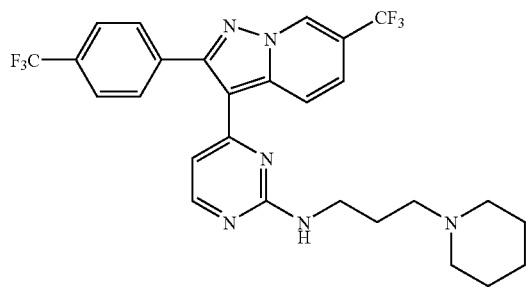

In an analogous procedure to Example 104, methyl 4–{6-(trifluoromethyl)-2-[4-(trifluoromethyl)phenyl]pyrazolo[1,5-a]pyridin-3-yl}pyrimidin-2-yl sulfone (0.02 g), 3-piperidin-1-ylpropylamine (0.04 mL) gave the title compound; $^1$H NMR (d$_6$-DMSO) δ 9.53(1H, s), 8.49(1H, bs), 8.18(1H, d), 7.88(4H, dd), 7.70(1H, d), 7.32(1H, bs), 6.35(1H, bs), 2.30(6H, bs), 1.66(2H, bs), 1.48(4H, bs), 1.37 (2H, bs); m/z 549 (M+1)$^+$.

Example 113

N-{4-[2-(3-chloro-4-fluorophenyl)-6-(trifluoromethyl)pyrazolo[1,5-a]pyridin-3-yl]pyrimidin-2-yl}-N-(3-piperidin-1-ylpropyl)amine

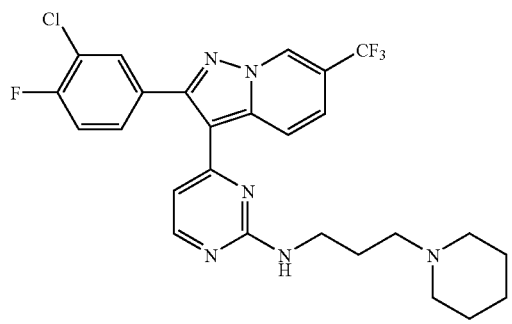

In an analogous procedure to Example 104, 4-[2-(3-chloro-4-fluorophenyl)-6-(trifluoromethyl)pyrazolo[1,5-a]pyridin-3-yl]pyrimidin-2-yl methyl sulfone (0.02 g), 3-piperidin-1-ylpropylamine (0.04 mL) gave the title compound; $^1$H NMR (d$_6$-DMSO) δ 9.51(1H, s), 8.49(1H, bs), 8.20(1H, d), 7.86(1H, dd), 7.71(1H, d), 7.65(1H, m), 7.58(1H, dd), 7.34(1H, bs), 6.41(1H, bs), 3.29(2H, bm), 2.31(4H, bs), 1.69(2H, bs), 1.49(4H, bm), 1.39(2H, bm); m/z 533 (M+1)$^+$.

Example 114

N-{4-[2-(3-chlorophenyl)-6-(trifluoromethyl)pyrazolo[1,5-a]pyridin-3-yl]pyrimidin-2-yl}-N-(3-piperidin-1-ylpropyl)amine

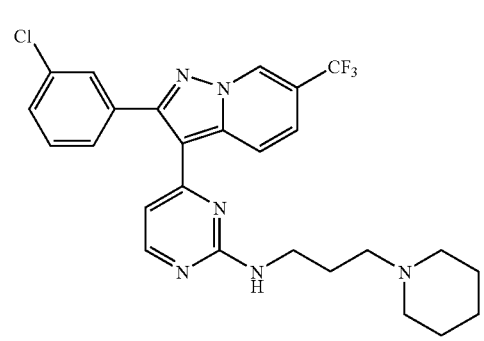

In an analogous procedure to Example 104, 4-[2-(3-chlorophenyl)-6-(trifluoromethyl)pyrazolo[1,5-a]pyridin-3-yl]pyrimidin-2-yl methyl sulfone (0.02 g) and 3-piperidin-1-ylpropylamine (0.04 mL) gave the title compound; $^1$H NMR (d$_6$-DMSO) δ 9.51(1H, s), 8.49(1H, bs), 8.16(1H, d), 7.72–7.65(2H, m), 7.61-7.51(3H, m), 7.33(1H, bs), 6.31(1H, bs), 3.29(2H, bs), 2.3(6H, bs), 1.69(2H, m), 1.47(4H, bs), 1.36(2H, m); m/z 515(M+1)+.

Example 115

N-(2-azepan-1-ylethyl)-N-(4-{6-(trifluoromethyl)-2-[4-(trifluoromethyl)phenyl]pyrazolo[1,5-a]pyridin-3-yl}pyrimidin-2-yl)amine

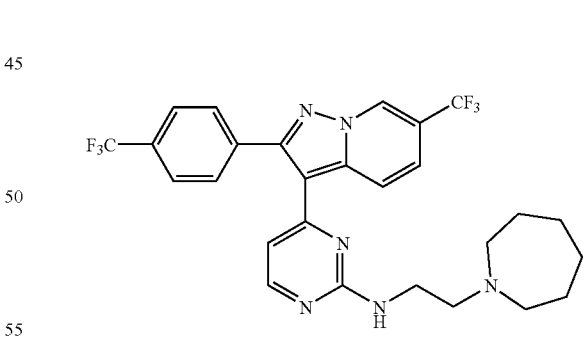

In an analogous procedure to Example 104, methyl 4–{6-(trifluoromethyl)-2-(4-(trifluoromethyl)phenyl]pyrazolo[1,5-a]pyridin-3-yl}pyrimidin-2-yl sulfone (0.02 g) and 2-azepan-1-ylethylamine (0.04 mL) gave the title compound $^1$H NMR (d$_6$-DMSO) δ 9.54(1H, s), 8.49(1H, bs), 8.20(1H, d), 7.89(4H, dd), 7.70(1H, d), 6.99(1H, bs), 6.40(1H, bs), 2.60(4H, bs), 1.54(8H, bs); m/z 450, 549 (M+1)$^+$.

Example 116

N-(2-azepan-1-ylethyl)-N-{4-[2-(3-chloro-4-fluorophenyl)-6-(trifluoromethyl)pyrazolo[1,5-a]pyridin-3-yl]pyrimidin-2-yl}amine

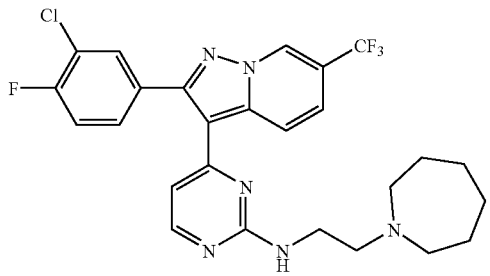

In an analogous procedure to Example 104, 4-[2-(3-chloro-4-fluorophenyl)-6-(trifluoromethyl)pyrazolo[1,5-a]pyridin-3-yl]pyrimidin-2-yl methyl sulfone (0.02 g) and 2-azepan-1-ylethylamine (0.04 mL) gave the title compound; $^1$H NMR (d$_6$-DMSO) δ 9.50(1H, s), 8.46(1H, bs), 8.20(1H, d), 7.84(1H, dd), 7.68(1H, dd), 7.62(1H, m), 7.56(1H, dd), 7.00(1H, bs), 6.44(1H, bs), 2.58(4H, bs), 1.54(8H, bs); m/z 533 (M+1)+.

Example 117

N-(2-azepan-1-ylethyl)-N-{4-[2-(3-chlorophenyl)-6-(trifluoromethyl)pyrazolo[1,5-a]pyridin-3-yl]pyrimidin-2-yl}amine

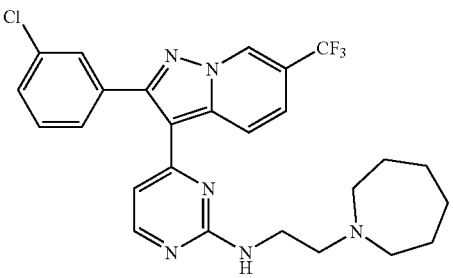

2-Azepan-1-ylethylamine (0.04 mL) and 4-[2-(3-chlorophenyl)-6-(trifluoromethyl)pyrazolo[1,5-a]pyridin-3-yl]pyrimidin-2-yl methyl sulfone (0.02 g) were mixed at room temperature and heated with an airgun until a homogenous melt was obtained (2 min). Upon cooling, water was added. The precipitated solid was filtered and dried to give the title compound as a beige solid (0.014 g); $^1$H NMR (d$_6$-DMSO) δ 9.51(1H, s), 8.49(1H, bs), 8.16(1H, d), 7.70–7.65(2H, m), 7.60–7.50(3H, m), 7.00(1H, bs), 6.36(1H, bs), 2.6(6H, bs), 1.6(8H, bs); m/z 515(M+1)$^+$.

Example 118

N-{4-[2-(4-fluorophenyl)-6-(trifluoromethyl)pyrazolo[1,5-a]pyridin-3-yl]pyrimidin-2-yl}-N-(2-morpholin-4-ylethyl)amine

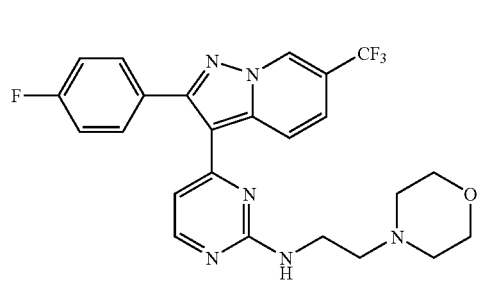

In an analogous procedure to Example 117, 4-[2-(4-fluorophenyl)-6-(trifluoromethyl)pyrazolo[1,5-a]pyridin-3-yl]pyrimidin-2-yl methyl sulfone (0.02 g) and 2-morpholin-4-ylethylamine (0.04 mL) gave the title compound; $^1$H NMR (CDCl$_3$) δ 8.83(1H, s), 8.50(1H, d), 8.14(1H, d), 7.61(2H, dd), 7.43 (1H, dd), 7.16(2H, dd), 6.37(1H, d), 5.72(1H, bs), 3.76(4H, t), 3.58(2H, ddd), 2.67(2H, t), 2.53 (4H, m); m/z 487 (M+1)$^+$.

Example 119

N-(2-morpholin-4-ylethyl)-N-(4-{6-(trifluoromethyl)-2-[4-(trifluoromethyl)phenyl]pyrazolo[1,5-a]pyridin-3-yl}pyrimidin-2-yl)amine In an analogous procedure to Example 117, methyl 4-{6-(trifluoromethyl)-2-[4-(trifluoromethyl)phenyl]pyrazolo[1,5-a]pyridin-3-yl}pyrimidin-2-yl sulfone (0.02 g) and 2-morpholin-4-ylethylamine (0.04 mL) gave the title compound; $^1$H NMR (d$_6$-DMSO) δ 9.52(1H, s), 8.48(1H, bs), 8.19(1H, d), 7.86(4H, dd), 7.70(1H, d), 7.07(1H, bs), 6.39(1H, bs), 3.56(4H, bt), 2.44(2H, bs), 2.36(4H, bs); m/z 537 (M+1)$^+$.

Example 120

N-{4-[2-(3-chloro-4-fluorophenyl)-6-(trifluoromethyl)pyrazolo[1,5-a]pyridin-3-yl]pyrimidin-2-yl}-N-(2-morpholin-4-ylethyl)amine

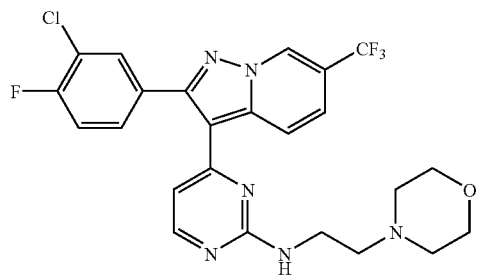

In an analogous procedure to Example 0.117, 4-[2-(3-chloro-4-fluorophenyl)-6-(trifluoromethyl)pyrazolo[1,5-a]pyridin-3-yl]pyrimidin-2-yl methyl sulfone (0.02 g) and 2-morpholin-4-ylethylamine (0.04 mL) gave the title compound; $^1$H NMR (d$_6$-DMSO) δ 9.50(1H, s), 8.47(1H, bs), 8.18(1H, d), 7.83(1H, dd), 7.69 (1H, d), 7.62(1H, m), 7.57(1H, dd), 7.09(1H, bs), 6.42(1H, bs), 3.57(4H, bt), 2.45(2H, bs), 2.37(4H, bs); m/z 521 (M+1)$^+$.

Example 121

N-(3-morpholin-4-ylpropyl)-N-(4-{6-(trifluoromethyl)-2-[4-(trifluoromethyl)phenyl]pyrazolo[1,5-a]pyridin-3-yl}pyrimidin-2-yl)amine

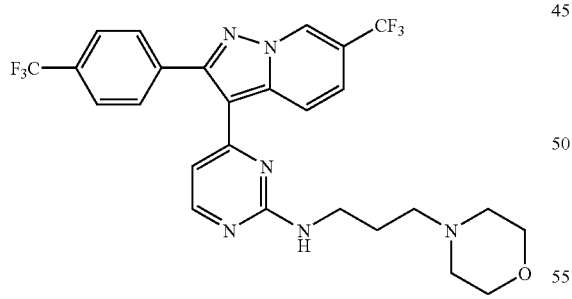

In an analogous procedure to Example 117, methyl 4-{6-(trifluoromethyl)-2-[4-(trifluoromethyl)phenyl]pyrazolo[1,5-a]pyridin-3-yl}pyrimidin-2-yl sulfone (0.02 g) and 3-morpholin-4-ylpropylamine (0.04 mL) gave the title compound; $^1$H NMR (d$_6$-DMSO) δ 9.54(1H, s), 8.49(1H, bs), 8.19(1H, d), 7.87(4H, dd), 7.72(1H, d), 7.29(1H, bs), 6.38(1H, bs), 3.56(4H, bs), 2.34(6H, bs), 1.68(2H, bs); m/z 551 (M+1)$^+$.

Example 122

N-{4-[2-(3-chloro-4-fluorophenyl)-6-(trifluoromethyl)pyrazolo[1,5-a]pyridin-3-yl]pyrimidin-2-yl}-N-(3-morpholin-4-ylpropyl)amine

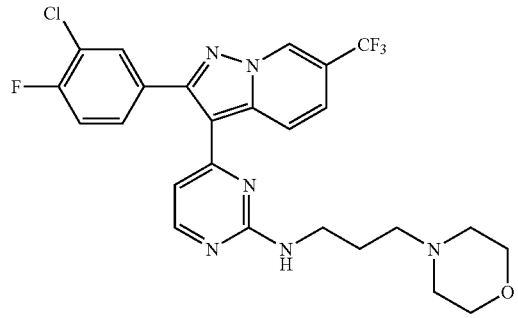

In an analogous procedure to Example 117, 4-[2-(3-chloro-4-fluorophenyl)-6-(trifluoromethyl)pyrazolo[1,5-a]pyridin-3-yl]pyrimidin-2-yl methyl sulfone (0.02 g) and 3-morpholin-4-ylpropylamine (0.04 mL) gave the title compound; $^1$H NMR (d$_6$-DMSO) δ 9.51(1H, s), 8.47(1H, bs), 8.19(1H, d), 7.85(1H, dd), 7.71(1H, d), 7.64(1H, m), 7.58 (1H, dd), 7.30(1H, bs), 6.41(1H, bs), 3.57(4H, bs), 2.35(6H, bs), 1.69(2H, bs); m/z 535 (M+1)$^+$.

Example 123

N-{4-[2-(3-chlorophenyl)-6-(trifluoromethyl)pyrazolo[1,5-a]pyridin-3-yl]pyrimidin-2-yl}-N-(3-morpholin-4-ylpropyl)amine

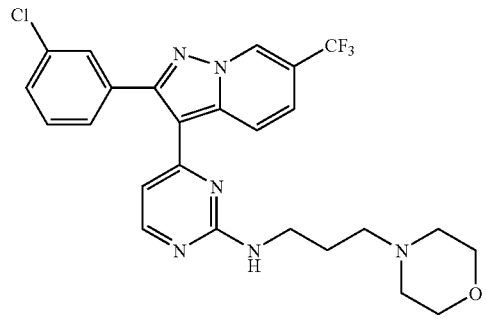

In an analogous procedure to Example 117, 4-[2-(3-chlorophenyl)-6-(trifluoromethyl)pyrazolo[1,5-a]pyridin-3-yl]pyrimidin-2-yl methyl sulfone (0.02 g) and 3-morpholin-4-ylpropylamine (0.04 mL) gave the title compound; $^1$H NMR (d$_6$-DMSO) δ 9.51(1H, s), 8.49(1H, bs), 8.16(1H, d), 7.72–7.65(2H, m), 7.617.51(3H, m), 7.30(1H, bs), 6.35(1H, bs), 3.55(4H, bs), 2.33(6H, bs), 1.69(2H, m); m/z 517(M+1)$^+$.

Example 124

N-{4-[2-(4-fluorophenyl)-6-(trifluoromethyl)pyrazolo[1,5-a]pyridin-3-yl]pyrimidin-2-yl}-N-[3-(4-methylpiperazin-1-yl)propyl]amine

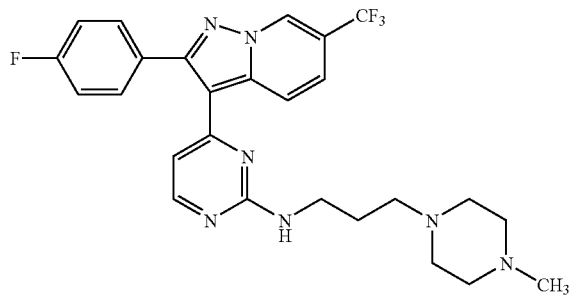

To a mixture of the enamine described in Example 87f (5.45 g, 14.45 mmol) and N-(3-(4-methylpiprazino)propyl) guanidine hydrogen sulfate (12.88 g, 3.0 equiv, 43.4 mmol) in anhydrous DMF (50 mL) under nitrogen was added powdered K$_2$CO$_3$ (2.75 g, 5.0 equiv, 20.0 mmol). The mixture was stirred and heated at 130° C. for 37 h and then filtered through a glass fritted funnel while warm. The solvent was evaporated under reduced pressure and the residue was triturated with EtOAc/Hexanes (1:10) to afford a solid that was collected by filtration and dried under vacuum to give the desired product as an off-white solid, 5.0 g (67%). $^1$H NMR (CDCl$_3$) δ 1.85 (m, 2H), 2.30 (s, 3H), 2.53 (m, 10H), 3.54 (m, 2H), 6.00 (br s, 1H), 6.30 (d, 1H), 7.14 (m, 2H), 7.40 (d, 1H), 7.60 (m, 2H), 8.08 (d, 1H), 8.49 (d, 1H), 8.81 (s, 1H). MS (ESI+) m/z 514.19 (M$^+$+H).

Example 125

N-{4-[2-(3-chloro-4-fluorophenyl)-6-(trifluoromethyl)pyrazolo-[1,5-a]pyridin-3-yl]pyrimidin-2-yl}-N-[3-(4-methylpiperazin-1-yl)propyl]amine

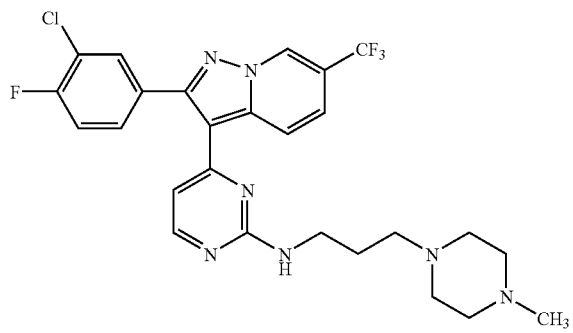

In an analogous procedure to Example 117, 4-[2-(3-chloro-4-fluorophenyl)-6-(trifluoromethyl)pyrazolo[1,5-a]pyridin-3-yl]pyrimidin-2-yl methyl sulfone (0.02 g) and 3-(4-methylpiperazin-1-yl)propylamine (0.04 mL) gave the title compound; $^1$H NMR (d$_6$-DMSO) δ 9.52(1H, s), 8.48 (1H, bs), 8.19(1H, d), 7.86(1H, dd), 7.71(1H, d), 7.64(1H, m), 7.58(1H, dd), 7.30(1H, bs), 6.40(1H, bs), 3.31(2H, bs), 2.33(8H, bm), 2.14(3H, bs), 1.68(2H, bs); m/z 548 (M+1)$^+$.

Example 126

N-{4-[2-(4-fluorophenyl)-6-(trifluoromethyl)pyrazolo[1,5-a]pyridin-3-yl]pyrimidin-2-yl}-N-[2-(4-methylpiperazin-1-yl)ethyl]amine

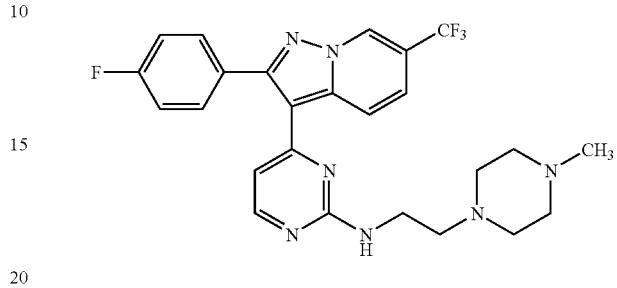

2-(4-Methylpiperazin-1-yl)ethyl]amine hydrochloride (0.058 g) and 4-[2-(4-fluorophenyl)-6-(trifluoromethyl)pyrazolo[1,5-a]pyridin-3-yl]pyrimidin-2-yl methyl sulfone (0.02 g) in dimethylformamide (0.5 mL) were treated with potassium carbonate (0.064 g) and heated at 50° C. for 16 h. Upon cooling, water was added. The precipitated solid was filtered and dried to give the title compound as a white solid (0.01 g); $^1$H NMR (CDCl$_3$) δ 8.82(1H, s), 8.50(1H, d), 8.12(1H, d), 7.65(2H, m), 7.45(1H, d), 7.15(2H, m), 6.36 (1H, d), 5.70(1H, bs), 3.58(2H, ddd), 2.66(2H, t), 2.55(8H, m), 2.30(3H, s); m/z 500 (M+1)$^+$.

Example 127

N-[2-(4-propylpiperazin-1-yl)ethyl]-N-(4-{6-(trifluoromethyl)-2-[4-(trifluoromethyl)phenyl]pyrazolo[1,5-a]pyridin-3-yl}pyrimidin-2-yl)amine

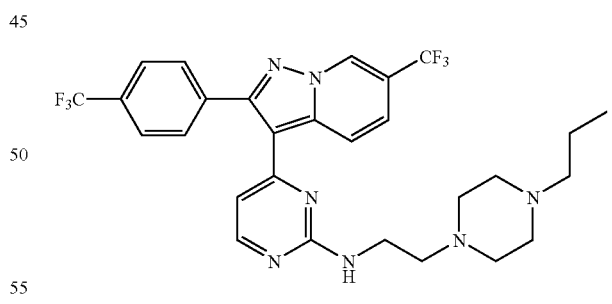

In an analogous procedure to Example 117, methyl{6-(trifluoromethyl)-2-[4-(trifluoromethyl)phenyl]pyrazolo[1,5-a]pyridin-3-yl}pyrimidin-2-yl sulfone (0.02 g) and 2-(4-propylpiperazin-1-yl)ethylamine (0.04 mL) gave the title compound; $^1$H NMR (d$_6$-DMSO) δ 9.53(1H, s), 8.46(1H, bs), 8.18(1H, d), 7.87(4H, dd), 7.69(1H, d), 7.03(1H, bs), 6.39(1H, bs), 2.46–2.27(8H, bm) 2.20(2H, t), 1.42(2H, m), 0.83 (3H, t); m/z 450, 578 (M+1)$^+$.

Example 128

N-{4-[2-(3-chloro-4-fluorophenyl)-6-(trifluoromethyl)pyrazolo-[1,5-a]pyridin-3-yl]pyrimidin-2-yl}-N-[2-(4-propylpiperazin-1-yl)ethyl]amine

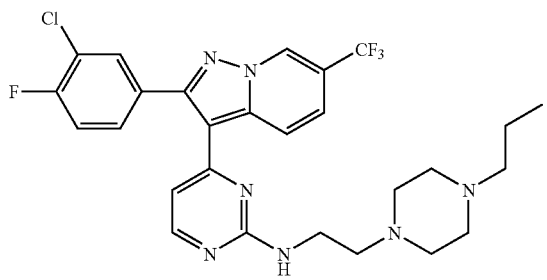

In an analogous procedure to Example 117, 4-[2-(3-chloro-4-fluorophenyl)-6-(trifluoromethyl)pyrazolo[1,5-a]pyridin-3-yl]pyrimidin-2-yl methyl sulfone (0.02 g) and 2-(4-propylpiperazin-1-yl)ethylamine (0.04 mL) gave the title compound; $^1$H NMR (d$_6$-DMSO) δ 9.51(1H, s), 8.50 (1H, bs), 8.20(1H, d), 7.84(1H, d), 7.72(1H, d), 7.63(1H, m), 7.57(1H, dd), 7.04(1H, bs), 6.43(1H, bs), 2.52–2.25(8H, bm), 2.20(2H, t), 1.42(2H, m), 0.85(3H, t); m/z 562 (M+1)$^+$.

Example 129

N-{4-[2-(3-chlorophenyl)-6-(trifluoromethyl)pyrazolo[1,5-a]pyridin-3-yl]pyrimidin-2-yl}-N-[2-(4-propylpiperazin-1-yl)ethyl]amine

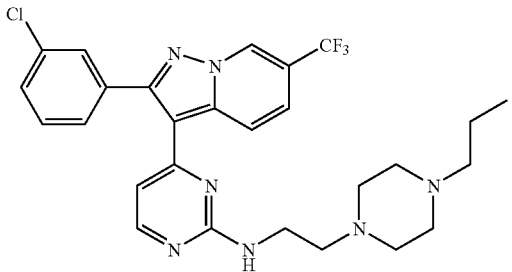

In an analogous procedure to Example 117, 4-[2-(3-chlorophenyl)-6-(trifluoromethyl)pyrazolo[1,5-a]pyridin-3-yl]pyrimidin-2-yl methyl sulfone (0.02 g) and 2-(4-propylpiperazin-1-yl)ethylamine (0.04 mL) gave the title compound; $^1$H NMR (d$_6$-DMSO) δ 9.51(1H, s), 8.51(1H, bs), 8.16(1H, d), 7.72–7.64(2H, m), 7.627.50(3H, m), 7.04 (1H, bs), 6.36(1H, bs), 2.35(8H, m), 2.19(2H, t), 1.4(2H, q), 0.83(3H, t); m/z 544(M+1)$^+$.

p38 Kinase Assay

The peptide substrate used in the p38 assay was biotin-IPTSPITTTYFFFRRR-amide. The p38 and MEK6 proteins were purified to homogeneity from *E. coli* expression systems. The fusion proteins were tagged at the N-terminus with Glutathione-S-Transferase (GST). The maximum activation was achieved by incubating 20 uL of a reaction mixture of 30 nM MEK6 protein and 120 nM p38 protein in the presence of 1.5 uM peptide and 10 mM Mg (CH$_3$CO$_2$)$_2$ in 100 mM HEPES$_7$ pH 7.5, added to 15 uL of a mixture of 1.5 uM ATP with 0.08 uCi [g-$^{33}$P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150 uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. IC$_{50}$ values were obtained by fitting raw data to % I=100*(1-(I-C2)/(C1-C2)), where I was CPM of background, C1 was positive control, and C2 was negative control.

JNK3 Kinase Assay Jnk-3alpha-2 (as a truncated construct, residues 39 to 224) was expressed in *E. coli* as a GST fusion protein. Following purification the GST portion was removed by thrombin cleavage. The enzyme was stored at –80° C. Substrate c-Jun was expressed as a GST fusion protein including a signal peptide (biotinylation site) in *E. coli*. Following purification the substrate was biotinylated on a specific lysine in the signal peptide using biotin ligase. Prior to assay Jnk-3 was pre-activated by incubation with MgATP. The enzyme (10 nM) was screened in 40 mM HEPES (pH 7.4), 150 mM NaCl, 20 mM glycerophosphate, 1 mM DTT, 0.2 mM vanadate, 200 nM biotin-c-Jun, 5 mM MgCl$_2$ and 10 uM ATP. Inhibitors were added over a conc range of from 0 to 10 uM in DMSO (fc 3%). The reaction was stopped by the addition of 25 mM EDTA. Phospho-c-Jun was detected using homogeneous time resolved fluorescence (HTRF) with a Eu-labelled antiphosphoserine (Serine 73) and streptavidin APC.

Cell Based Assay for Cytokines Production in PBMNC

Human peripheral blood mononuclear cells were isolated from heparinized blood by LSM (Organon Teknika) from volunteer donors. Purified human peripheral blood mononuclear cells were then suspended at a concentration of 2×10$^6$ cells/ml in RPMI 1640 medium supplemented with 10% heat-inactivated FBS and 1% antibiotics. Aliquots of 100 µl (2×10$^5$ cells) were added to 96-well microliter plates. Test compounds at 0.1 nM-10 mM dose ranges (final-DMSO concentration in culture medium was 0.1%) were then added to the cells for 10–15 minutes before the addition of lipopolysaccharide (1 ng/ml). After incubation at 37° C. in a 5% CO$_2$ incubator for 18–20 h, cell free supernatants were collected by centrifugation at 800 g. The supernatant was then assayed for the amount of TNFα and IL-1β by using Quantikine immunoassay kits developed by R&D Systems (Minneapolis, Minn.).

Murine LPS—Stimulated Serum TNF Inhibition Protocol

The potency of compounds of the invention as inhibitors of serum TNFα elevation in mice treated with lipopolysaccharide (LPS) was determined as follows; a) for subcutaneous (s.c.) administration, test compound was dissolved in DMSO and added to a mixture of 0.9% sodium chloride solution and 30% Trappsol HPB-20 (Cyclodextrin Technology Development Inc., Gainesville, Fla. USA) for a final DMSO concentration of 1%. The dosing solution was sonicated briefly and 0.2 mL was injected subcutaneously 10 min prior to LPS injection; b) for per oral (p.o.) administration, test compounds were formulated in 0.2 mL of PBS and 0.1% Tween 80 and given orally via gavage 10 min prior to LPS administration.

C3/hen female mice were injected intraperitoneally with 200 µg/kg LPS (*Escherichia coil*, Serotype 0111:B4, Sigma Chemical Co, St. Louis, Mo.) in PBS and sacrificed 90 min later by CO$_2$ asphyxiation. Blood was immediately taken from the caudal vena cava and plasma prepared and frozen at −80° C. Plasma concentrations of TNF were measured by ELISA (Genzyme Co., Cambridge Mass.).

Cell Based Efficacy (MTT Assay)

The potency of compounds of the invention are tested for their ability to inhibit cell proliferation and cell viability. The metabolic conversion of 3-(4,5-dimethylthiazol-2-yl)-2,5-diphenyltetrazolium bromide (MTT, Sigma #M2128) to a reduced form was a commonly used measure of cellular viability. Following was the procedure:

Cells are maintained in 75 cm² tissue culture flasks until ready for use. The cells are grown and plated for the assay in Dulbecco's modified Eagle's media containing 10% fetal bovine serum. For example, the following cell lines can be used: a) human foreskin fibroblasts (HFF), b) HT29 (human colon carcinoma cell line), c) MDA-MB468 (human breast carcinoma cell line), d) RKO (human colon adenocarcinoma cell line), e) SW620 (human colon carcinoma cell line), f) A549 (human lung carcinoma cell line), and g) MIA PACA (human pancreatic carcinoma cell line). Cells are maintained at 37° C. in 10% $CO_2$, 90% humidified air. Cells are plated in 96-well tissue culture plates at the densities listed below (Table 6). 100 µL of cell suspension was added to each well of the 96-well plate except the top row of the plate which contains no cells and serves as a reference for the spectrophotometer.

TABLE 6

| Cell line | Density |
|---|---|
| HFF | 2500 cells/well |
| HT29 cell lines | 2500 cells/well |
| MDA-MB-468 cell line | 5000 cells/well |
| SW620 | 4000 cells/well |
| MIA PACA | 3000 cells/well |
| PC-3 | 4500 cells/well |

Cells are incubated overnight in Dulbecco's modified Eagle's media containing 10% fetal bovine serum at 37° C. in 10% $CO_2$, 90% humidified air prior to dosing. Cells are dosed in 10 sequential 3-fold dilutions starting at 30 µM depending upon the solubility of the compound. Compounds with solubilities of less than 30 µM are dosed at the highest soluble concentration. Stock solutions of compounds are made in 100% dimethyl sulfoxide (DMSO). Stock solutions are diluted in Dulbecco's modified Eagle's media containing 100 ug/mL gentamicin and 0.3 to 0.6% DMSO at the twice the highest concentration to be placed on the cells. If compounds have been dissolved in DMSO the final concentration of DMSO on the cells was kept below 0.3%. 3-fold serial dilutions are performed on each compound to prepare 10 concentrations of the compound for dosing. 100 µL of diluted compound was added to the 100 µL of media currently on the dish. For each concentration of compound, 2–4 replicate wells are prepared.

Cells are returned to incubator and allowed to proliferate in the presence of compound for 72 h before addition of MTT. MTT was prepared in phosphate buffered saline (Irvine Scientific #9240) at a concentration of 2 mg/mL. 50 µL per well of MTT solution was added to the 200 µL of media to yield a final concentration of 0.4 mg/mL and plates are returned to the incubator for 4 h. After 4 h incubation the media, compound and MTT mixture was aspirated from the plates and 100 µL of 100% DMSO was added to each well in addition to 25 uL of Sorenson's Buffer (0.1M glycine, 0.1M NaCl, pH 10.5). Quantitation of metabolic reduction of MTT in each plate was performed by reading optical density at 570 nm wavelength on a Molecular Devices UV max microplate reader. Growth inhibition curves and 50% inhibitory concentrations are determined using Microsoft Excel.

Representative data for compounds of the current invention wherein Z is CH are given in Table 7. The columns in Table 7 refer to the compound by Example #, inhibition of p38 kinase ($IC_{50}$), inhibition of TNF release from human peripheral blood mononuclear cells (PBMNC) following stimulation with LPS ($IC_{50}$), % inhibition of murine TNF production in mice following an LPS challenge and cytotoxicity toward the HFF cell line ($IC_{50}$).

TABLE 7

| Example # | P38 kinase | TNF/PBMNC | % inh. (dose) | HFF |
|---|---|---|---|---|
| 1 | + | + | 65 (30 mpk) | ++++ |
| 5 | ++ | ++ | 11 (30 mpk) | NT |
| 6 | + | NT | NT | NT |
| 16 | + | + | NT | ++++ |
| 23 | + | + | NT | NT |
| 30 | + | + | 45 (30 mpk) | ++++ |
| 31 | + | + | 42 (30 mpk) | NT |
| 37 | + | + | NT | +++ |

Representative data for compounds of the current invention wherein Z is N are given in Table 8. The columns in Table 8 refer to the compound by Example #, Inhibition of p38 kinase ($IC_{50}$), inhibition of JNK3 kinase ($IC_{50}$), inhibition of TNF release from human peripheral blood mononuclear cells (PBMNC) following stimulation with LPS ($IC_{50}$), % inhibition of murine TNF production in mice following an LPS challenge and cytotoxicity toward the HFF cell line ($IC_{50}$).

TABLE 8

| Example # | p38 kinase | JNK3 kinase | TNF/PBMNC | % inh. (dose) | HFF |
|---|---|---|---|---|---|
| 56 | ++ | NT | ++ | 67% (30 mpk) | ++++ |
| 57 | + | NT | + | 56% (30 mpk) | NT |
| 60 | + | NT | + | 88% (30 mpk) | NT |
| 61 | + | + | NT | NT | NT |
| 64 | + | NT | + | 62% (30 mpk) | NT |
| 65 | + | NT | NT | NT | NT |
| 68 | + | + | + | 24% (30 mpk) | NT |
| 69 | + | NT | + | 45% (30 mpk) | NT |
| 72 | + | NT | NT | NT | NT |
| 73 | + | + | + | 52% (30 mpk) | NT |
| 75 | + | + | + | 90% (30 mpk) | NT |
| 76 | + | NT | NT | NT | NT |
| 79 | + | NT | NT | NT | NT |
| 80 | + | NT | + | NT | NT |
| 82 | + | NT | + | 87% (30 mpk) | NT |
| 84 | + | + | NT | NT | NT |
| 86 | + | + | NT | NT | NT |

| Key (Tables 7 and 8) | |
|---|---|
| Symbol | Range |
| + | <0.5 µM |
| ++ | 0.5–5 µM |
| +++ | 5–50 µM |
| ++++ | >50 µM |
| NT | Not Tested |

Results for p38 assays (using Assay II above) and JNK 3 assays are given for further examples in Table 9 below:

TABLE 9

| Example # | JNK3 IC50 | p38 IC50 |
|---|---|---|
| 87 | + | ++ |
| 88 | + | + |
| 89 | + | +++ |
| 90 | + | +++ |
| 93 | ++ | +++ |
| 94 | ++ | +++ |
| 95 |  | + |
| 96 |  | ++ |
| 97 |  | + |
| 98 | + | ++ |
| 99 | + | ++ |
| 100 | + | ++ |
| 103 |  | + |
| 104 | + | ++ |
| 105 | + | ++ |
| 106 | ++ | +++ |
| 108 |  | + |
| 109 | + | ++ |
| 110 | + | ++ |
| 112 | + | + |
| 113 | ++ | ++ |
| 116 | + | ++ |
| 117 | + | ++ |
| 119 |  | + |
| 120 | ++ | +++ |
| 121 |  | + |
| 122 | ++ | ++ |
| 123 | ++ | +++ |
| 124 | ++ | +++ |
| 125 | ++ | +++ |
| 127 | + | + |
| 128 | ++ | +++ |
| 129 | ++ | +++ |

Key:
+ = 10 μM–1 μM
++ = 1 μM–0.1 μM
+++ = 0.1 μM–0.01 μM

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

What is claimed is:
1. A compound of Formula (I):

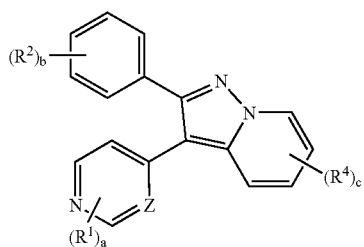

(I)

or a salt or solvate thereof:
wherein
Z is N;
a is 1 or 2;
b is 1, 2 or 3;
c is 1, 2 or 3;

each $R^1$ is independently selected from groups of the formula $$-(X)_d-(CH_2)_e-R^5$$

wherein
d is 0 or 1;
e is 0 to 6;
X is O, $NR^6$ or $S(O)_f$ where f is 0, 1 or 2;
$R^5$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, $NR^7R^8$, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$, $C(=NR^7)NR^7R^8$, $NR^7(C=NR^7)NR^7R^8$, $NHC(O)R^7$ or $N(C_{1-3}alkyl)C(O)R^7$;
each $R^2$ is independently selected from hydrogen, cyano, halogen, trihalomethyl, $OC_{1-6}$alkyl, $C_{1-6}$alkyl, $C_{2-6}$alkenyl, $C_{2-6}$alkynyl, $S(O)_g C_{1-6}$alkyl where g is 0, 1 or 2, $NC_{1-6}$alkyl$(C_{1-6}$alkyl), hydroxyl or nitro;
each $R^4$ is independently selected from groups of the formula $$-(Y)_d-(CH_2)_e-R^3$$

wherein
d is 0 or 1;
e is 0 to 6;
Y is O or $S(O)_f$ where f is 0, 1 or 2;
$R^3$ is hydrogen, halogen, $C_{1-6}$alkyl, $C_{2-6}$alkenyl, $C_{2-6}$alkynyl, $C_{3-12}$cycloalkyl, heterocyclyl, aryl, heteroaryl, hydroxyl, cyano, nitro, trihalomethyl, phthalamido, $C_6H_4NR^7R^8$, $C_6H_4(CH_2)NR^7R^8$, $C(O)R^7$, $C(O)NR^7R^8$, $OC(O)R^7$, $OC(O)NR^7R^8$, $CO_2R^7$, $OCO_2R^7$, $SO_2R^7$, $SO_2NR^7R^8$ or $C(=NR^7)NR^7R^8$;
$R^6$ is H, $C_{1-6}$alkyl, $C_{2-6}$alkenyl, aryl, heteroaryl, $C_{3-12}$cycloalkyl, or heterocyclyl;
$R^7$ and $R^8$ are each independently H, $C_{1-8}$alkyl, $C_{2-6}$alkenyl, $SO_2C_{1-6}$alkyl, $(CH_2)_m-C_{3-12}$cycloalkyl, $(CH_2)_m$-aryl, $(CH_2)_m$-heterocyclyl, $(CH_2)_m$-heteroaryl, wherein m=0, 1 or 2, or may, together with the nitrogen atom to which they are bound, form a heterocyclyl group; and
wherein any of said alkyl, alkenyl and alkynyl groups may be optionally substituted with up to three members selected from halogen, hydroxyl, oxo, cyano, $NR^7R^8$, $C_{1-6}$alkyl, $OC_{1-6}$alkyl, $S(O)C_{1-6}$alkyl, $S(O)_2C_{1-6}$alkyl and $SO_2NR^7R^8$; and
wherein any of said cycloalkyl, heterocyclyl, aryl, and heteroaryl groups may be optionally substituted with substituents selected from a group consisting of $C_{1-6}$alkyl, $C_{1-6}$alkoxy, $C_{1-6}$alkylsulfenyl, $C_{1-6}$alkylsulfinyl, $C_{1-6}$alkylsulfonyl, hydroxy, oxo, mercapto, nitro, cyano, halogen, $C_{1-6}$perfluoroalkyl, amino optionally substituted by $C_{1-6}$alkyl, carbamoyl optionally substituted by $C_{1-6}$alkyl, $NR^7R^8$, carboxy and aminosulfonyl optionally substituted by $C_{1-6}$alkyl;
with the proviso that $(R^2)_b$, $(R^1)_a$ and $(R^4)_c$ cannot all represent solely hydrogen substitution;
and with the proviso that when $(R^2)_b$ represents solely hydrogen or methyl substitution, $(R^4)_c$ cannot represent solely hydrogen substitution;
and with the proviso that $R^4$ may not be located on the 7-position of the pyrazolopyridine ring system as numbered below:

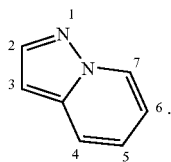

2. A compound according to claim 1 wherein a is 1.

3. A compound according to claim 1 wherein $R^1$ is in the 2-position of the pyrimidinyl ring.

4. A compound according to claim 1 wherein $R^1$ is —$NR^6$—$(CH_2)_e$—$R^5$.

5. A compound according to claim 1 wherein b is 1.

6. A compound according to claim 1 wherein $R^2$ is selected from hydrogen, cyano, halogen, trihalomethyl and $OC_{1-6}$alkyl.

7. A compound according to claim 1 wherein $R^2$ is fluoro.

8. A compound according to claim 1 wherein $R^2$ is in the 4-position of the phenyl ring.

9. A compound according to claim 1 wherein c is 1.

10. A compound according to claim 1 wherein $R^4$ is in the 6-position of the pyrazolopyridine ring.

11. A compound according to claim 1 wherein $R^4$ is selected from $C_{1-6}$alkyl, halogen, cyano and trihalomethyl.

12. 3-(4-[2-(4-Fluorophenyl)-6-trifluoromethylpyrazolo[1,5-a]pyridin-3-yl]-2-pyrimidinylamino)-1-propanol or a salt or solvate thereof.

13. A pharmaceutical composition comprising a compound according to claim 1, in admixture with one or more pharmaceutically acceptable carriers, diluents or excipients.

* * * * *